US008216586B2

(12) United States Patent
Albang et al.

(10) Patent No.: US 8,216,586 B2
(45) Date of Patent: Jul. 10, 2012

(54) LIPASES AND USES THEREOF

(75) Inventors: Richard Albang, Martinsried (DE);
Andreas Fritz, Martinsried (DE); Oliver Heinrich, Martinsried (DE); Hilmar Ilgenfritz, Martinsried (DE); Dieter Maier, Martinsried (DE); Christian Wagner, Martinsried (DE); Ulrike Folkers, München (DE); Beatrix Gerhard, Unterhaching (DE); Fabio Spreafico, Martinsried (DE); Lex De Boer, Wateringen (NL); Roelf Bernhard Meima, Kamerik (NL)

(73) Assignee: DSM IP Assets B.V., Heerlen (NL)

( * ) Notice: Subject to any disclaimer, the term of this patent is extended or adjusted under 35 U.S.C. 154(b) by 479 days.

(21) Appl. No.: 12/453,292

(22) Filed: May 6, 2009

(65) Prior Publication Data

US 2009/0232936 A1 Sep. 17, 2009

Related U.S. Application Data

(62) Division of application No. 10/524,983, filed as application No. PCT/EP03/09145 on Aug. 15, 2003, now Pat. No. 7,550,280.

(30) Foreign Application Priority Data

| Aug. 19, 2002 | (EP) | 02102168 |
| Aug. 19, 2002 | (EP) | 02102169 |
| Aug. 19, 2002 | (EP) | 02102170 |
| Aug. 19, 2002 | (EP) | 02102171 |
| Aug. 19, 2002 | (EP) | 02102172 |
| Aug. 19, 2002 | (EP) | 02102173 |
| Aug. 19, 2002 | (EP) | 02102174 |
| Aug. 19, 2002 | (EP) | 02102176 |
| Aug. 19, 2002 | (EP) | 02102178 |
| Aug. 19, 2002 | (EP) | 02102179 |
| Aug. 19, 2002 | (EP) | 02102181 |
| Aug. 19, 2002 | (EP) | 02102183 |

(51) Int. Cl.
*A61K 39/00* (2006.01)
*C12N 9/20* (2006.01)

(52) U.S. Cl. ............ 424/192.1; 435/198; 435/252.3; 435/320.1; 536/23.2

(58) Field of Classification Search .............. 435/198, 435/252.3, 320.1; 424/192.1; 536/23.2
See application file for complete search history.

(56) References Cited

U.S. PATENT DOCUMENTS

| 4,433,092 A | 2/1984 | Nemeth |
| 4,567,046 A | 1/1986 | Inoue et al. |
| 4,631,211 A | 12/1986 | Houghten |
| 4,704,692 A | 11/1987 | Ladner |
| 4,708,781 A | 11/1987 | Poorten |
| 4,946,778 A | 8/1990 | Ladner et al. |
| 5,194,392 A | 3/1993 | Geysen |
| 5,223,409 A | 6/1993 | Ladner |
| 5,480,971 A | 1/1996 | Houghten et al. |
| 2006/0281080 A1 | 12/2006 | Albang et al. |

FOREIGN PATENT DOCUMENTS

| EP | 0426211 | 11/1993 |
| EP | 0619947 | 10/1994 |
| EP | 0659344 | 6/1995 |
| EP | 0687734 | 12/1995 |
| JP | 60-078529 | 5/1985 |
| JP | 62-111629 | 5/1987 |
| JP | 63-258528 | 10/1988 |
| WO | 90/02809 | 3/1990 |
| WO | 91/17271 | 11/1991 |
| WO | 92/01047 | 1/1992 |
| WO | 92/09690 | 6/1992 |
| WO | 92/15679 | 9/1992 |
| WO | 92/18619 | 10/1992 |
| WO | 92/20791 | 11/1992 |
| WO | 93/01288 | 1/1993 |
| WO | 00/56762 | 9/2000 |
| WO | 01/11974 | 2/2001 |
| WO | 01/27251 | 4/2001 |
| WO | 02/26044 | 4/2002 |
| WO | 02/49441 | 6/2002 |

OTHER PUBLICATIONS

EMBL database Accession No. AF315651 (Nov. 2000) from Brito et al. "*Aspergillus nidulans* lipase (lipA) gene, where mutation confers resistance to undecanoic acid" (Oct. 2000).
EMBL database Accession No. BE760259 (Oct. 2000) from Tsang "*Aspergillus niger* expressed sequence tags" (2000).
GENESEQ database Accession No. AAF11551 (Dec. 2005) of White et al. "Genome sequence of the radioresistant bacterium *Deinococcus radiodurans* R1" Science 286:1571-1577 (1999).
UniProt database Accession No. P32946 (Oct. 1993) from Longhi et al. "Cloning and nucleotide sequences of two lipase genes from *Candida cylindracea*" Biochim. Biophys. Acta 1131:227-232 (1993).
UniProt database Accession No. P32949 (Oct. 1993) from Lotti et al. "Cloning and analysis of *Candida cylindracea* lipase sequences" Gene 124:45-55 (1993).

(Continued)

*Primary Examiner* — Tekchand Saidha
(74) *Attorney, Agent, or Firm* — Nixon & Vanderhye P.C.

(57) ABSTRACT

The invention relates to a newly identified polynucleotide sequence comprising a gene that encodes a novel lipolytic enzyme from *Aspergillus niger* The invention features the full length nucleotide sequence of the novel gene, the cDNA sequence comprising the full length coding sequence of the novel lipolytic enzyme as well as the amino acid sequence of the full-length functional protein and functional equivalents thereof. The invention also relates to methods of using these enzymes in industrial processes and methods of diagnosing fungal infections. Also included in the invention are cells transformed with a polynucleotide according to the invention and cells wherein a lipolytic enzyme according to the invention is genetically modified to enhance its activity and/or level of expression.

18 Claims, No Drawings

OTHER PUBLICATIONS

UniProt database Accession No. Q876R3 (Jun. 2003) from Brito et al. "*Aspergillus nidulans* triacylglycerol lipase (lipA) gene, wild type allele" (Sep. 2001).

Namboodiri et al. "Purification and biochemical characterization of a novel thermostable lipase from *Aspergillus niger*" Lipids 35:495-502 (2000).

Sugihara et al. "Purification and characterization of *Aspergillus niger* lipase" Agric. Biol. Chem. 52:1591-1592 (1988).

Torossian et al. "Purification and characterization of an acid-resistant triacylglycerol lipase from *Aspergillus niger*" Biotechnol. Appl. Biochem. 13:205-211 (1991).

International Search Report for PCT/EP2003/09145, nine pages dated Aug. 19, 2004.

Int'l Preliminary Examination Report for PCT/EP2003/09145, eight pages dated Dec. 1, 2004.

SEQUENCE LISTING

<160> NUMBER OF SEQ ID NOS: 39

<210> SEQ ID NO 1
<211> LENGTH: 3728
<212> TYPE: DNA
<213> ORGANISM: Aspergillus niger

<400> SEQUENCE: 1

```
cgggcaatta cgatccgagc gcgctatcta cgtgcaccgg aagcttgctc cttgatttgt      60
tgtttcataa tacttatttg tgctctttag cccgactgca gtggtggctg catgttgggc     120
aggtatttaa ctttgggcga taccaactac gcgtgcactt tgaagcatag cacggcgcgc     180
cggggatgcg tgtcgtctta tgactataat tgatgtggcc gactgactgc ttggtgttag     240
ggatcttgtg tttatcttgg ttttctgtac ttagaagaga gtgccggtgg catggtggtc     300
gatataacta gagcaatgcg tgtctccatc ctcatcctca tcggccatcc cttatacccct    360
gatggcgccg aagggtgaga atggcgatgg gcagaaataa tatactgtgt atagtctgtc     420
ctatcctcct tgtgcactgc aaagtcagtt gatcatcatc cccactcaat cgtccactca     480
tgctctatat ccgagacaaa ccacaactta ttcaatttaa gcccgagtcc ataatcatcc     540
acaaccaccc cacagccagg gtacatccag ggtctctttc ccgccggaga aactaagccc     600
ttagctcctc actaggacct cccgccgcgt cttggctcct catcaccaac tttccaccta     660
taaactgcat caaacatgct gcaaagccac gactgctgct gcatgcaccc caacatcatc     720
cccgcataat acatccatcc ctgaagcaat caagcttgac tctgttgttt cttcggagat     780
gttaaccatt cgtactttcc aaatgacatc aatccaactg atagacatcg ccatcctcct     840
caataccatg gacgccccac gtccatgtca aaagtaagac tagctcagct cggcgttaat     900
caattatgat tgcgagtctc aatccctgag tcatgtgttc tctgtgtcgg agaattagac     960
tgaattcagc tgctcgttgc cactcctagc tccctgataa aggtcctcac ttcgtctcgt    1020
agctggctgg ctgcatattc tccggtgact aagttaacag aaccagcaac ttagtagcca    1080
tggcgagcgc actcctctgg ctctccctgc tgggtggcag caccctagcc tcaactctag    1140
acaccagtaa taccccctacc atcaagagag cagacgcagg aaacaacacc tcctcaatcc    1200
caacagccac cctcaacaac accgtcttca tcggccgttc cctgcccgag ttcgagcagg    1260
agttgttcct gggtatcaag tttgctgatg agcccgtgcg attcaccccg tcgacgttga    1320
aaaccgtcta tcgcgccaat gacagcgaca acggggtgta tcatgcttcc acagcatccg    1380
gactgcagac ttcctcgggg accgtgctct acaacgccac agagtatggg tatgattgcc    1440
ccgggtatgg atccgatgag acggagctgg cggaggaagg atatgcgcgg ttcgatgaga    1500
actgtatgaa cctgaatata attcggccca agagagagaa agaggatgag ttgttgcctg    1560
tgatgatttg gatctttggt ggtggttggg tgcagggtgc gactgctgat ccgaggtagg    1620
atactatagt tttgtgctgt gctgtgtggg gttgatgctg acgatgtgca aggtacaata    1680
tgagctatat tgttcgccag ggtgcgttga atgataagcc tgtcttgggt gtctcgatca    1740
attaccgtgt ggctgcgttt ggattccttg actctgtcga ggttatggtg cgtttcttcc    1800
ttcaccgtca agtatatggg tttcagctga catgacatct gtaggaatcc ggcaacacga    1860
acctaggact tcgtgatcag cgcgtcgcca tgcattgggt caaacaaaac atcaaggcgt    1920
ttggtggtga cccggacaag atcaccatct ggggagaatc agcgtgagat tataccctaa    1980
tagcattcga tatacagcgc ctgacatggc acagtggtgc ctacagcgtc ggagcccacc    2040
```

```
tggtcaccaa cgacggtgac aacgagggtc tattcagagc cggtatgcac accactcccc    2100
aattctcgtc tcctcatctg ctaaccagca tagccatcat ggaatccggc aacgcagtcg    2160
gaccccccta caacggcacg gactggtacc agccgatgta cgaccagatc gtgaacgcaa    2220
ccaagtatgt cctcaccttc cccaaaagac aatactcaaa tgactagtat atatactaac    2280
tacatgaaag ctgcaccacc tcaagcaaca cccttcaatg cctccgcgaa gtccccttct    2340
caacgatcta caccgccgca gacatcgccc tggaatggtt cgccaccatc gacggcacct    2400
tcatcaaaga atatccccaa atcagcatta cggagggccg cttcgccaag gtccccatcc    2460
tccatggcac aacaccgac gagggcgtga gtttcggtac gacgggcgtg aacactgatg    2520
ccgaagcgat ccagcagttg atgggtgagc ccccccccc cccccttccc accaatcccc    2580
aagatatata tatagtacga gatactaagg tgaaatgaaa atgatagcat ccaaacgctg    2640
ggtcctaaac gaaacccaag ccacgaccct cctatcgcac tatcccaaca tctccgccct    2700
aggctgtccc tacggatggg gcaacacgac ctggccgaag ctggggtatg aatataagcg    2760
ctacgagtcg atggcgggcg atctgtgcat ggttgctccg aggaggttgc tcagtcagaa    2820
gatgaaggag tatgaggagc aagtgtttgc gtatcggtgg gatgtcgctg cgttgaatga    2880
ttcgagtacg attggggtgg cgcatttgc tgaggtaatg ccatccatcc atccctatt    2940 attggttttc cctgcggtat gatatttggt atgctaatga tgtgttactg cgtgcatgca    3000
tagatcccgt ttgttttcgc caaccctgtg cagaacatca ctccgttggg aagtgatccc    3060
gcaagactgg agttgggtaa tctggccgcg aggatgtgga cggcttttgt gacggatttg    3120
gatccgaatg ggcatggtgg tacgttcctc ttctccatct tattagaatt gtgaaatgaa    3180
gcgtgtggtt ctaatgaggg tgacagtctc tggtatcccc cactggccga atacaaacct    3240
cactgatccg agggactttg tgttccggct accgagggat ggaagttatg tggagaagga    3300
tacttttagg acgggggga ttgattatat taatacaatt gtgcggtaag ttgctgctaa    3360
gtagtactac tatatgtata taggagggtg tgggtgaaaa gtagatagta gtactatatc    3420
aaggatggtt agatactata tactatttac tactactgta atgttactat aatcaagact    3480
agaagaaagt ctactgattg attacttcga ctgatcgatt gtattgatct agttagtata    3540
tcaaatcgac aaagagccgc cgttttatt cattcatatt tcccgccact aagccagtat    3600
actataccat agtagtatag ctggtttagt tgatgccgag cagctcaacc tcgctaattg    3660
atatcagcat tccaatccat tttttcactg gcaaagaata ttagaagagg aaggaggagg    3720
aggataac                                                            3728
```

<210> SEQ ID NO 2
<211> LENGTH: 1749
<212> TYPE: DNA
<213> ORGANISM: Aspergillus niger
<220> FEATURE:
<221> NAME/KEY: CDS
<222> LOCATION: (1)..(1749)

<400> SEQUENCE: 2

```
atg gcg agc gca ctc ctc tgg ctc tcc ctg ctg ggt ggc agc acc cta    48
Met Ala Ser Ala Leu Leu Trp Leu Ser Leu Leu Gly Gly Ser Thr Leu
1               5                   10                  15 gcc tca act cta gac acc agt aat acc cct acc atc aag aga gca gac    96
Ala Ser Thr Leu Asp Thr Ser Asn Thr Pro Thr Ile Lys Arg Ala Asp
            20                  25                  30 gca gga aac aac acc tcc tca atc cca aca gcc acc ctc aac aac acc   144
Ala Gly Asn Asn Thr Ser Ser Ile Pro Thr Ala Thr Leu Asn Asn Thr
        35                  40                  45
```

| | | |
|---|---|---|
| gtc ttc atc ggc cgt tcc ctg ccc gag ttc gag cag gag ttg ttc ctg<br>Val Phe Ile Gly Arg Ser Leu Pro Glu Phe Glu Gln Glu Leu Phe Leu<br>50                            55                            60 | | 192 |
| ggt atc aag ttt gct gat gag ccc gtg cga ttc acc ccg tcg acg ttg<br>Gly Ile Lys Phe Ala Asp Glu Pro Val Arg Phe Thr Pro Ser Thr Leu<br>65                            70                            75                            80 | | 240 |
| aaa acc gtc tat cgc gcc aat gac agc gac aac ggg gtg tat cat gct<br>Lys Thr Val Tyr Arg Ala Asn Asp Ser Asp Asn Gly Val Tyr His Ala<br>                            85                                    90                            95 | | 288 |
| tcc aca gca tcc gga ctg cag act tcc tcg ggg acc gtg ctc tac aac<br>Ser Thr Ala Ser Gly Leu Gln Thr Ser Ser Gly Thr Val Leu Tyr Asn<br>                100                             105                            110 | | 336 |
| gcc aca gag tat ggg tat gat tgc ccc ggg tat gga tcc gat gag acg<br>Ala Thr Glu Tyr Gly Tyr Asp Cys Pro Gly Tyr Gly Ser Asp Glu Thr<br>                115                             120                            125 | | 384 |
| gag ctg gcg gag gaa gga tat gcg cgg ttc gat gag aac tgt atg aac<br>Glu Leu Ala Glu Glu Gly Tyr Ala Arg Phe Asp Glu Asn Cys Met Asn<br>130                            135                            140 | | 432 |
| ctg aat ata att cgg ccc aag aga gag aaa gag gat gag ttg ttg cct<br>Leu Asn Ile Ile Arg Pro Lys Arg Glu Lys Glu Asp Glu Leu Leu Pro<br>145                            150                            155                            160 | | 480 |
| gtg atg att tgg atc ttt ggt ggt ggt tgg gtg cag ggt gcg act gct<br>Val Met Ile Trp Ile Phe Gly Gly Gly Trp Val Gln Gly Ala Thr Ala<br>                            165                            170                            175 | | 528 |
| gat ccg agg tac aat atg agc tat att gtt cgc cag ggt gcg ttg aat<br>Asp Pro Arg Tyr Asn Met Ser Tyr Ile Val Arg Gln Gly Ala Leu Asn<br>                180                             185                            190 | | 576 |
| gat aag cct gtc ttg ggt gtc tcg atc aat tac cgt gtg gct gcg ttt<br>Asp Lys Pro Val Leu Gly Val Ser Ile Asn Tyr Arg Val Ala Ala Phe<br>                195                             200                            205 | | 624 |
| gga ttc ctt gac tct gtc gag gtt atg gaa tcc ggc aac acg aac cta<br>Gly Phe Leu Asp Ser Val Glu Val Met Glu Ser Gly Asn Thr Asn Leu<br>                210                             215                            220 | | 672 |
| gga ctt cgt gat cag cgc gtc gcc atg cat tgg gtc aaa caa aac atc<br>Gly Leu Arg Asp Gln Arg Val Ala Met His Trp Val Lys Gln Asn Ile<br>225                            230                            235                            240 | | 720 |
| aag gcg ttt ggt ggt gac ccg gac aag atc acc atc tgg gga gaa tca<br>Lys Ala Phe Gly Gly Asp Pro Asp Lys Ile Thr Ile Trp Gly Glu Ser<br>                            245                                   250                            255 | | 768 |
| gct ggt gcc tac agc gtc gga gcc cac ctg gtc acc aac gac ggt gac<br>Ala Gly Ala Tyr Ser Val Gly Ala His Leu Val Thr Asn Asp Gly Asp<br>                            260                                265                            270 | | 816 |
| aac gag ggt cta ttc aga gcc gcc atc atg gaa tcc ggc aac gca gtc<br>Asn Glu Gly Leu Phe Arg Ala Ala Ile Met Glu Ser Gly Asn Ala Val<br>                275                             280                            285 | | 864 |
| gga ccc ccc tac aac ggc acg gac tgg tac cag ccg atg tac gac cag<br>Gly Pro Pro Tyr Asn Gly Thr Asp Trp Tyr Gln Pro Met Tyr Asp Gln<br>                      290                              295                            300 | | 912 |
| atc gtg aac gca acc aac tgc acc acc tca agc aac acc ctt caa tgc<br>Ile Val Asn Ala Thr Asn Cys Thr Thr Ser Ser Asn Thr Leu Gln Cys<br>305                            310                            315                            320 | | 960 |
| ctc cgc gaa gtc ccc ttc tca acg atc tac acc gcc gca gac atc ggc<br>Leu Arg Glu Val Pro Phe Ser Thr Ile Tyr Thr Ala Ala Asp Ile Gly<br>                            325                                   330                            335 | | 1008 |
| ctg gaa tgg ttc gcc acc atc gac ggc acc ttc atc aaa gaa tat ccc<br>Leu Glu Trp Phe Ala Thr Ile Asp Gly Thr Phe Ile Lys Glu Tyr Pro<br>                      340                              345                            350 | | 1056 |
| caa atc agc att acg gag ggc cgc ttc gcc aag gtc ccc atc ctc cat<br>Gln Ile Ser Ile Thr Glu Gly Arg Phe Ala Lys Val Pro Ile Leu His<br>                            355                                   360                            365 | | 1104 |

```
ggc acc aac acc gac gag ggc gtg agt ttc ggt acg acg ggc gtg aac       1152
Gly Thr Asn Thr Asp Glu Gly Val Ser Phe Gly Thr Thr Gly Val Asn
        370                 375                 380 act gat gcc gaa gcg atc cag cag ttg atg gca tcc aaa cgc tgg gtc       1200
Thr Asp Ala Glu Ala Ile Gln Gln Leu Met Ala Ser Lys Arg Trp Val
385                 390                 395                 400 cta aac gaa acc caa gcc acg acc ctc cta tcg cac tat ccc aac atc       1248
Leu Asn Glu Thr Gln Ala Thr Thr Leu Leu Ser His Tyr Pro Asn Ile
                405                 410                 415 tcc gcc cta ggc tgt ccc tac gga tgg ggc aac acg acc tgg ccg aag       1296
Ser Ala Leu Gly Cys Pro Tyr Gly Trp Gly Asn Thr Thr Trp Pro Lys
            420                 425                 430 ctg ggg tat gaa tat aag cgc tac gag tcg atg gcg ggc gat ctg tgc       1344
Leu Gly Tyr Glu Tyr Lys Arg Tyr Glu Ser Met Ala Gly Asp Leu Cys
        435                 440                 445 atg gtt gct ccg agg agg ttg ctc agt cag aag atg aag gag tat gag       1392
Met Val Ala Pro Arg Arg Leu Leu Ser Gln Lys Met Lys Glu Tyr Glu
450                 455                 460 gag caa gtg ttt gcg tat cgg tgg gat gtc gct gcg ttg aat gat tcg       1440
Glu Gln Val Phe Ala Tyr Arg Trp Asp Val Ala Ala Leu Asn Asp Ser
465                 470                 475                 480 agt acg att ggg gtg gcg cat ttt gct gag atc cct ttt gtt ttc gcc       1488
Ser Thr Ile Gly Val Ala His Phe Ala Glu Ile Pro Phe Val Phe Ala
                485                 490                 495 aac cct gtg cag aac atc act ccg ttg gga agt gat ccc gca aga ctg       1536
Asn Pro Val Gln Asn Ile Thr Pro Leu Gly Ser Asp Pro Ala Arg Leu
            500                 505                 510 gag ttg ggt aat ctg gcc gcg agg atg tgg acg gct ttt gtg acg gat       1584
Glu Leu Gly Asn Leu Ala Ala Arg Met Trp Thr Ala Phe Val Thr Asp
        515                 520                 525 ttg gat ccg aat ggg cat ggt gtc tct ggt atc ccc cac tgg ccg aaa       1632
Leu Asp Pro Asn Gly His Gly Val Ser Gly Ile Pro His Trp Pro Lys
530                 535                 540 tac aac ctc act gat ccg agg gac ttt gtg ttc cgg cta ccg agg gat       1680
Tyr Asn Leu Thr Asp Pro Arg Asp Phe Val Phe Arg Leu Pro Arg Asp
545                 550                 555                 560 gga agt tat gtg gag aag gat act ttt agg acg ggg ggg att gat tat       1728
Gly Ser Tyr Val Glu Lys Asp Thr Phe Arg Thr Gly Gly Ile Asp Tyr
                565                 570                 575 att aat aca att gtg cgg taa                                           1749
Ile Asn Thr Ile Val Arg
            580

<210> SEQ ID NO 3
<211> LENGTH: 582
<212> TYPE: PRT
<213> ORGANISM: Aspergillus niger

<400> SEQUENCE: 3

Met Ala Ser Ala Leu Leu Trp Leu Ser Leu Leu Gly Gly Ser Thr Leu
1               5                   10                  15

Ala Ser Thr Leu Asp Thr Ser Asn Thr Pro Thr Ile Lys Arg Ala Asp
            20                  25                  30

Ala Gly Asn Asn Thr Ser Ser Ile Pro Thr Ala Thr Leu Asn Asn Thr
        35                  40                  45

Val Phe Ile Gly Arg Ser Leu Pro Glu Phe Glu Gln Glu Leu Phe Leu
    50                  55                  60

Gly Ile Lys Phe Ala Asp Glu Pro Val Arg Phe Thr Pro Ser Thr Leu
65                  70                  75                  80
```

-continued

```
Lys Thr Val Tyr Arg Ala Asn Asp Ser Asp Asn Gly Val Tyr His Ala
                 85                  90                  95

Ser Thr Ala Ser Gly Leu Gln Thr Ser Ser Gly Thr Val Leu Tyr Asn
            100                 105                 110

Ala Thr Glu Tyr Gly Tyr Asp Cys Pro Gly Tyr Gly Ser Asp Glu Thr
            115                 120                 125

Glu Leu Ala Glu Glu Gly Tyr Ala Arg Phe Asp Glu Asn Cys Met Asn
        130                 135                 140

Leu Asn Ile Ile Arg Pro Lys Arg Glu Lys Glu Asp Glu Leu Leu Pro
145                 150                 155                 160

Val Met Ile Trp Ile Phe Gly Gly Gly Trp Val Gln Gly Ala Thr Ala
                165                 170                 175

Asp Pro Arg Tyr Asn Met Ser Tyr Ile Val Arg Gln Gly Ala Leu Asn
            180                 185                 190

Asp Lys Pro Val Leu Gly Val Ser Ile Asn Tyr Arg Val Ala Ala Phe
        195                 200                 205

Gly Phe Leu Asp Ser Val Glu Val Met Glu Ser Gly Asn Thr Asn Leu
    210                 215                 220

Gly Leu Arg Asp Gln Arg Val Ala Met His Trp Val Lys Gln Asn Ile
225                 230                 235                 240

Lys Ala Phe Gly Gly Asp Pro Asp Lys Ile Thr Ile Trp Gly Glu Ser
                245                 250                 255

Ala Gly Ala Tyr Ser Val Gly Ala His Leu Val Thr Asn Asp Gly Asp
            260                 265                 270

Asn Glu Gly Leu Phe Arg Ala Ala Ile Met Glu Ser Gly Asn Ala Val
        275                 280                 285

Gly Pro Pro Tyr Asn Gly Thr Asp Trp Tyr Gln Pro Met Tyr Asp Gln
    290                 295                 300

Ile Val Asn Ala Thr Asn Cys Thr Thr Ser Ser Asn Thr Leu Gln Cys
305                 310                 315                 320

Leu Arg Glu Val Pro Phe Ser Thr Ile Tyr Thr Ala Ala Asp Ile Gly
                325                 330                 335

Leu Glu Trp Phe Ala Thr Ile Asp Gly Thr Phe Ile Lys Glu Tyr Pro
            340                 345                 350

Gln Ile Ser Ile Thr Glu Gly Arg Phe Ala Lys Val Pro Ile Leu His
        355                 360                 365

Gly Thr Asn Thr Asp Glu Gly Val Ser Phe Gly Thr Thr Gly Val Asn
    370                 375                 380

Thr Asp Ala Glu Ala Ile Gln Gln Leu Met Ala Ser Lys Arg Trp Val
385                 390                 395                 400

Leu Asn Glu Thr Gln Ala Thr Thr Leu Leu Ser His Tyr Pro Asn Ile
                405                 410                 415

Ser Ala Leu Gly Cys Pro Tyr Gly Trp Gly Asn Thr Thr Trp Pro Lys
            420                 425                 430

Leu Gly Tyr Glu Tyr Lys Arg Tyr Glu Ser Met Ala Gly Asp Leu Cys
        435                 440                 445

Met Val Ala Pro Arg Arg Leu Leu Ser Gln Lys Met Lys Glu Tyr Glu
    450                 455                 460

Glu Gln Val Phe Ala Tyr Arg Trp Asp Val Ala Ala Leu Asn Asp Ser
465                 470                 475                 480

Ser Thr Ile Gly Val Ala His Phe Ala Glu Ile Pro Phe Val Phe Ala
                485                 490                 495

Asn Pro Val Gln Asn Ile Thr Pro Leu Gly Ser Asp Pro Ala Arg Leu
            500                 505                 510
```

```
Glu Leu Gly Asn Leu Ala Ala Arg Met Trp Thr Ala Phe Val Thr Asp
            515                 520                 525
Leu Asp Pro Asn Gly His Gly Val Ser Gly Ile Pro His Trp Pro Lys
        530                 535                 540
Tyr Asn Leu Thr Asp Pro Arg Asp Phe Val Phe Arg Leu Pro Arg Asp
545                 550                 555                 560
Gly Ser Tyr Val Glu Lys Asp Thr Phe Arg Thr Gly Gly Ile Asp Tyr
                565                 570                 575
Ile Asn Thr Ile Val Arg
            580

<210> SEQ ID NO 4
<211> LENGTH: 3853
<212> TYPE: DNA
<213> ORGANISM: Aspergillus niger

<400> SEQUENCE: 4
ctttcctgtt gcccggtctt tgttgttgtc ataggataca attacccaga caacgttcgg      60
tttgtcgatc agttttaagt gtgcgtggac tgacagccaa ggccactggg gcccctgcct     120
ctatcattta attccacacg ctcgcctctg cagctctggc accagcgttg caaattccag     180
gggtcagcct acgtggcatt aggctctaag agaatctgag ggaaaggatt tcacttagaa     240
aaatttatcg gtccggcttg tccgatcggt aggaaggcat tgcttcccct catatgcggc     300
cccggttccc aagcagctga ttcgggacgt tttccggctt gatcgctata ctctcataat     360
ctctcctgca agagctggat aaacttggtt tcttatcttc cgtggggatg ccatagtcca     420
gtagacgctg tctcgaaatt gagtagcacc actatttacg ggcaagttaa tggcacatgt     480
attagctttg tactgacggt tgaaatgtgg agcaatttcc ggctatgtac cggatctgtt     540
ccggatatct tcatcgcaat tagttagtac ataaaactcc ctagtcacgc aagaacggtt     600
cgaacataac gaattaaaaa ttctcattct ctggcaaggc ttcgaaatgt ttgtttcctc     660
gcttgctcta ttagcactta ttgctccttt gatcgcaatt gcggtaaaaa tagaacagcc     720
aggaataaat ccaaatccca cagctactgt acgaaatggc acctactatg gtctccataa     780
ccagcactat aatcaagacc tcttttctcgg tattccatat gcacagcaac ctattggtga     840
ccttcgcttg cggaccccac gatcaatgaa cacctcctgg ccagtaccaa gaaatgcaac     900
agaatattca cccgcatgtg ttggatttaa tcagacagag ggtgcttccg aagcctgcct     960
tactctcaat gtcgtccgcc cggcaagcat cgctctttct gaaagtcttc ccgttgctgg    1020
tcagtatata ccccaaatct gatcagaagg ccagaactg actttgcgct cggccccagt     1080
ctggattcat ggcgggggat tcacctccgg ctcttcatca gagaaacaat acaatctgtc    1140
cttcatcgtt gatcagtcag tccaaatgga aaagcccgtt atcgcagtca gtctaaatta    1200
tcgtcttcaa tgctgggggtt ttatgtggag caaggagatg aaggaagccg gagtagggaa    1260
cctgggactt agagaccaac gattagctct gcattggata caagaaagta ggtatctcga    1320
tagtgaagct cttccaagta cggatctgac catgacttag acattgctgc gtttggtgga    1380
gaccctgctc aggttacaat ttggggtgaa agtgccggcg ctaatagtgt tggcacacat    1440
ctggttgctt acgagggcg cgatgatggt atattccgtg cagctatcag tgaaagtggt    1500
gccccaagtg tttaccaacg ttatccaaca cctgctgaat ggcagcccta ttatgatggt    1560
attgtgaatg catcaggctg cagttcagca acggatactt tggcttgtct ccgaacaatt    1620
ccaactaaca tattgcatgg catctttgac aacacgtcta ttgtacccat gcacgctatt    1680
```

```
tcaggcctca gcggagcaaa attcattcct gtcatagatg acgacttcat taaagagagt    1740
gccacggttc agctccagaa gggcaacttc gtcaaagttc cctacttgat tggagctaac    1800
gccgacgaag ggactgcatt tgctgtggag ggagtcaaca cagatgctga gtttcgcgag    1860
ctagtcaaag gttggggcct caacaacgct accacggata tcttggaggc cctataccca    1920
gacattcctc agataggaat ccccgccata atggttggaa ggccaccgtc cggatatgga    1980
aatcaataca agcgtgtggc cgcatttcag ggtgatgtta acatccatgc cgcacgtagg    2040
ttgaccagtc agatctggtc atcccgcaat atctcagtat atagctacat gtttgacgtt    2100
atcagccctg gatatggccc ctctgctggt tcctatgctg gggctactca tggtactgat    2160
attccgtacg ttttctataa tctggatggc ctggggtatg actcgaacaa caagtccata    2220
gaaagcatac ctaacagtta ttcccgcatg agcaaaatta tgtcaagaat gtgggtcagt    2280
tttgtgacaa cattggaccc aaatcattct ggaggtatgg tcccacatcc cattcctatg    2340
attgcgcaat gtcagacccg agctgaatca actatcttct taggaactaa tgttcagtgg    2400
ccgccataca atatcgataa tccggagata atctttttcg ataccgatgt cacgaacctc    2460
acatatgtga gttctgacgt ttaccgtgcg gagggcataa aatacatcag tgatcacctt    2520
gcaagtgatt tcgggcactg agatcacata tcttctcggt ctaattttag aatgactgtg    2580
gtctcatcta accagacttg gcccgcaggt ctttacgccc actggtggta attgatgcaa    2640
cccccaagct atatagtgtc tggggctttg aactactgtc aatgagcgaa aattgactat    2700
ttcccttat gactcatgta gtagcatttg tgctggcact gtgatcaaga tatgtttttc    2760
gagattaccg gtagcagagt agtcgatgtc gccaatatta ttcatctata atgaatagta    2820
ataacttagg agtcattcag tatagtcgat actgacataa gtatctttc ttgtgatatt    2880
tataatatgt cccgtttggc cttgtttgta gtaactctca tagcctgctg cttgagaact    2940
catctgttca atcatagaga taccaattat ggaaggatag gttggcatcg gtgtttgttt    3000
catcaagact actacctaat aagtcactga agaaggctgt agactgaaag cgcgacattg    3060
atgattagaa ttccaacttt ggtcaacata tgcattagac tataaaaggg acatgttaga    3120
agaactaagt acatacgacc atagggtgtg gaaaacaggg cttcccgtcc gctcagccgt    3180
acttaagcca cacgccggga ggttagtagt tgggtgggtg accaccagcg aatcccttct    3240
gttgtatgtt tttgtttctc tataaaactt ttggtcgggc atctcgagat gtcttccagg    3300
atgctaaaac cttcgggttc ctcacagcgg agatggtgtc aactggcttt tttaatgcat    3360
tcttggctaa agtgctcgtg aacacggcaa tatagtacga tgatatctga gtttgtggt    3420
gtcaagacat atgcttattg tgaccaccag accataaatc ggagtattca cagcttatat    3480
catcctcaaa cattgattgc atagtagagt gtctaactct tgactcaagg gattgaaaat    3540
gattatttga aaatataggt agttttgaat aacattctgg cacacgagct ttagctggat    3600
tagtaagatg tgacgccgat tttgggtttg attatgtcat catttggcag ttcccccaga    3660
ggacagcccg gttaagaacg aacctttct gagcccgtat acaaatgcgg ggaacagaga    3720
tgaggagatg ccgaagcatg ctttggcaaa cagaagccac tgtgaaaaac cattcacaga    3780
tatcttgtga tagttggatt gcactgactg tccgcgaaag cgagcatatc tatcccgtat    3840
actgagaact agt                                                      3853
```

<210> SEQ ID NO 5
<211> LENGTH: 1743
<212> TYPE: DNA
<213> ORGANISM: Aspergillus niger
<220> FEATURE:

```
<221> NAME/KEY: CDS
<222> LOCATION: (1)..(1743)

<400> SEQUENCE: 5 atg ttt gtt tcc tcg ctt gct cta tta gca ctt att gct cct ttg atc    48
Met Phe Val Ser Ser Leu Ala Leu Leu Ala Leu Ile Ala Pro Leu Ile
1               5                   10                  15 gca att gcg gta aaa ata gaa cag cca gga ata aat cca aat ccc aca    96
Ala Ile Ala Val Lys Ile Glu Gln Pro Gly Ile Asn Pro Asn Pro Thr
            20                  25                  30 gct act gta cga aat ggc acc tac tat ggt ctc cat aac cag cac tat    144
Ala Thr Val Arg Asn Gly Thr Tyr Tyr Gly Leu His Asn Gln His Tyr
        35                  40                  45 aat caa gac ctc ttt ctc ggt att cca tat gca cag caa cct att ggt    192
Asn Gln Asp Leu Phe Leu Gly Ile Pro Tyr Ala Gln Gln Pro Ile Gly
    50                  55                  60 gac ctt cgc ttg cgg acc cca cga tca atg aac acc tcc tgg cca gta    240
Asp Leu Arg Leu Arg Thr Pro Arg Ser Met Asn Thr Ser Trp Pro Val
65                  70                  75                  80 cca aga aat gca aca gaa tat tca ccc gca tgt gtt gga ttt aat cag    288
Pro Arg Asn Ala Thr Glu Tyr Ser Pro Ala Cys Val Gly Phe Asn Gln
                85                  90                  95 aca gag ggt gct tcc gaa gcc tgc ctt act ctc aat gtc gtc cgc ccg    336
Thr Glu Gly Ala Ser Glu Ala Cys Leu Thr Leu Asn Val Val Arg Pro
            100                 105                 110 gca agc atc gct ctt tct gaa agt ctt ccc gtt gct gtc tgg att cat    384
Ala Ser Ile Ala Leu Ser Glu Ser Leu Pro Val Ala Val Trp Ile His
        115                 120                 125 ggc ggg gga ttc acc tcc ggc tct tca tca gag aaa caa tac aat ctg    432
Gly Gly Gly Phe Thr Ser Gly Ser Ser Ser Glu Lys Gln Tyr Asn Leu
    130                 135                 140 tcc ttc atc gtt gat cag tca gtc caa atg gaa aag ccc gtt atc gca    480
Ser Phe Ile Val Asp Gln Ser Val Gln Met Glu Lys Pro Val Ile Ala
145                 150                 155                 160 gtc agt cta aat tat cgt ctt caa tgc tgg ggt ttt atg tgg agc aag    528
Val Ser Leu Asn Tyr Arg Leu Gln Cys Trp Gly Phe Met Trp Ser Lys
                165                 170                 175 gag atg aag gaa gcc gga gta ggg aac ctg gga ctt aga gac caa cga    576
Glu Met Lys Glu Ala Gly Val Gly Asn Leu Gly Leu Arg Asp Gln Arg
            180                 185                 190 tta gct ctg cat tgg ata caa gaa aac att gct gcg ttt ggt gga gac    624
Leu Ala Leu His Trp Ile Gln Glu Asn Ile Ala Ala Phe Gly Gly Asp
        195                 200                 205 cct gct cag gtt aca att tgg ggt gaa agt gcc ggc gct aat agt gtt    672
Pro Ala Gln Val Thr Ile Trp Gly Glu Ser Ala Gly Ala Asn Ser Val
    210                 215                 220 ggc aca cat ctg gtt gct tac gga ggg cgc gat gat ggt ata ttc cgt    720
Gly Thr His Leu Val Ala Tyr Gly Gly Arg Asp Asp Gly Ile Phe Arg
225                 230                 235                 240 gca gct atc agt gaa agt ggt gcc cca agt gtt tac caa cgt tat cca    768
Ala Ala Ile Ser Glu Ser Gly Ala Pro Ser Val Tyr Gln Arg Tyr Pro
                245                 250                 255 aca cct gct gaa tgg cag ccc tat tat gat ggt att gtg aat gca tca    816
Thr Pro Ala Glu Trp Gln Pro Tyr Tyr Asp Gly Ile Val Asn Ala Ser
            260                 265                 270 ggc tgc agt tca gca acg gat act ttg gct tgt ctc cga aca att cca    864
Gly Cys Ser Ser Ala Thr Asp Thr Leu Ala Cys Leu Arg Thr Ile Pro
        275                 280                 285 act aac ata ttg cat ggc atc ttt gac aac acg tct att gta ccc atg    912
Thr Asn Ile Leu His Gly Ile Phe Asp Asn Thr Ser Ile Val Pro Met
    290                 295                 300
```

```
cac gct att tca ggc ctc agc gga gca aaa ttc att cct gtc ata gat      960
His Ala Ile Ser Gly Leu Ser Gly Ala Lys Phe Ile Pro Val Ile Asp
305                 310                 315                 320 gac gac ttc att aaa gag agt gcc acg gtt cag ctc cag aag ggc aac     1008
Asp Asp Phe Ile Lys Glu Ser Ala Thr Val Gln Leu Gln Lys Gly Asn
                325                 330                 335 ttc gtc aaa gtt ccc tac ttg att gga gct aac gcc gac gaa ggg act     1056
Phe Val Lys Val Pro Tyr Leu Ile Gly Ala Asn Ala Asp Glu Gly Thr
            340                 345                 350 gca ttt gct gtg gag gga gtc aac aca gat gct gag ttt cgc gag cta     1104
Ala Phe Ala Val Glu Gly Val Asn Thr Asp Ala Glu Phe Arg Glu Leu
        355                 360                 365 gtc aaa ggt tgg ggc ctc aac aac gct acc acg gat atc ttg gag gcc     1152
Val Lys Gly Trp Gly Leu Asn Asn Ala Thr Thr Asp Ile Leu Glu Ala
370                 375                 380 cta tac cca gac att cct cag ata gga atc ccc gcc ata atg gtt gga     1200
Leu Tyr Pro Asp Ile Pro Gln Ile Gly Ile Pro Ala Ile Met Val Gly
385                 390                 395                 400 agg cca ccg tcc gga tat gga aat caa tac aag cgt gtg gcc gca ttt     1248
Arg Pro Pro Ser Gly Tyr Gly Asn Gln Tyr Lys Arg Val Ala Ala Phe
                405                 410                 415 cag ggt gat gtt aac atc cat gcc gca cgt agg ttg acc agt cag atc     1296
Gln Gly Asp Val Asn Ile His Ala Ala Arg Arg Leu Thr Ser Gln Ile
            420                 425                 430 tgg tca tcc cgc aat atc tca gta tat agc tac atg ttt gac gtt atc     1344
Trp Ser Ser Arg Asn Ile Ser Val Tyr Ser Tyr Met Phe Asp Val Ile
        435                 440                 445 agc cct gga tat ggc ccc tct gct ggt tcc tat gct ggg gct act cat     1392
Ser Pro Gly Tyr Gly Pro Ser Ala Gly Ser Tyr Ala Gly Ala Thr His
450                 455                 460 ggt act gat att ccg tac gtt ttc tat aat ctg gat ggc ctg ggg tat     1440
Gly Thr Asp Ile Pro Tyr Val Phe Tyr Asn Leu Asp Gly Leu Gly Tyr
465                 470                 475                 480 gac tcg aac aac aag tcc ata gaa agc ata cct aac agt tat tcc cgc     1488
Asp Ser Asn Asn Lys Ser Ile Glu Ser Ile Pro Asn Ser Tyr Ser Arg
                485                 490                 495 atg agc aaa att atg tca aga atg tgg gtc agt ttt gtg aca aca ttg     1536
Met Ser Lys Ile Met Ser Arg Met Trp Val Ser Phe Val Thr Thr Leu
            500                 505                 510 gac cca aat cat tct gga ggt atg gtc cca cat ccc att cct atg att     1584
Asp Pro Asn His Ser Gly Gly Met Val Pro His Pro Ile Pro Met Ile
        515                 520                 525 gcg caa tgt cag acc cga gct gaa tca act atc ttc tta gga act aat     1632
Ala Gln Cys Gln Thr Arg Ala Glu Ser Thr Ile Phe Leu Gly Thr Asn
530                 535                 540 gtt cag tgg ccg cca tac aat atc gat aat ccg gag ata atc ttt ttc     1680
Val Gln Trp Pro Pro Tyr Asn Ile Asp Asn Pro Glu Ile Ile Phe Phe
545                 550                 555                 560 gat acc gat gtc acg aac ctc aca tat act tgg ccc gca ggt ctt tac     1728
Asp Thr Asp Val Thr Asn Leu Thr Tyr Thr Trp Pro Ala Gly Leu Tyr
                565                 570                 575 gcc cac tgg tgg taa                                                  1743
Ala His Trp Trp
            580

<210> SEQ ID NO 6
<211> LENGTH: 580
<212> TYPE: PRT
<213> ORGANISM: Aspergillus niger

<400> SEQUENCE: 6
```

```
Met Phe Val Ser Ser Leu Ala Leu Leu Ala Leu Ile Ala Pro Leu Ile
1               5                   10                  15

Ala Ile Ala Val Lys Ile Glu Gln Pro Gly Ile Asn Pro Asn Pro Thr
            20                  25                  30

Ala Thr Val Arg Asn Gly Thr Tyr Tyr Gly Leu His Asn Gln His Tyr
        35                  40                  45

Asn Gln Asp Leu Phe Leu Gly Ile Pro Tyr Ala Gln Gln Pro Ile Gly
    50                  55                  60

Asp Leu Arg Leu Arg Thr Pro Arg Ser Met Asn Thr Ser Trp Pro Val
65                  70                  75                  80

Pro Arg Asn Ala Thr Glu Tyr Ser Pro Ala Cys Val Gly Phe Asn Gln
                85                  90                  95

Thr Glu Gly Ala Ser Glu Ala Cys Leu Thr Leu Asn Val Val Arg Pro
            100                 105                 110

Ala Ser Ile Ala Leu Ser Glu Ser Leu Pro Val Ala Val Trp Ile His
        115                 120                 125

Gly Gly Gly Phe Thr Ser Gly Ser Ser Glu Lys Gln Tyr Asn Leu
    130                 135                 140

Ser Phe Ile Val Asp Gln Ser Val Gln Met Glu Lys Pro Val Ile Ala
145                 150                 155                 160

Val Ser Leu Asn Tyr Arg Leu Gln Cys Trp Gly Phe Met Trp Ser Lys
                165                 170                 175

Glu Met Lys Glu Ala Gly Val Gly Asn Leu Gly Leu Arg Asp Gln Arg
            180                 185                 190

Leu Ala Leu His Trp Ile Gln Glu Asn Ile Ala Ala Phe Gly Gly Asp
        195                 200                 205

Pro Ala Gln Val Thr Ile Trp Gly Glu Ser Ala Gly Ala Asn Ser Val
    210                 215                 220

Gly Thr His Leu Val Ala Tyr Gly Gly Arg Asp Asp Gly Ile Phe Arg
225                 230                 235                 240

Ala Ala Ile Ser Glu Ser Gly Ala Pro Ser Val Tyr Gln Arg Tyr Pro
                245                 250                 255

Thr Pro Ala Glu Trp Gln Pro Tyr Tyr Asp Gly Ile Val Asn Ala Ser
            260                 265                 270

Gly Cys Ser Ser Ala Thr Asp Thr Leu Ala Cys Leu Arg Thr Ile Pro
        275                 280                 285

Thr Asn Ile Leu His Gly Ile Phe Asp Asn Thr Ser Ile Val Pro Met
    290                 295                 300

His Ala Ile Ser Gly Leu Ser Gly Ala Lys Phe Ile Pro Val Ile Asp
305                 310                 315                 320

Asp Asp Phe Ile Lys Glu Ser Ala Thr Val Gln Leu Gln Lys Gly Asn
                325                 330                 335

Phe Val Lys Val Pro Tyr Leu Ile Gly Ala Asn Ala Asp Glu Gly Thr
            340                 345                 350

Ala Phe Ala Val Glu Gly Val Asn Thr Asp Ala Glu Phe Arg Glu Leu
        355                 360                 365

Val Lys Gly Trp Gly Leu Asn Asn Ala Thr Thr Asp Ile Leu Glu Ala
    370                 375                 380

Leu Tyr Pro Asp Ile Pro Gln Ile Gly Ile Pro Ala Ile Met Val Gly
385                 390                 395                 400

Arg Pro Pro Ser Gly Tyr Gly Asn Gln Tyr Lys Arg Val Ala Ala Phe
                405                 410                 415

Gln Gly Asp Val Asn Ile His Ala Ala Arg Arg Leu Thr Ser Gln Ile
```

```
                    420              425              430
Trp Ser Ser Arg Asn Ile Ser Val Tyr Ser Tyr Met Phe Asp Val Ile
            435                  440                 445
Ser Pro Gly Tyr Gly Pro Ser Ala Gly Ser Tyr Ala Gly Ala Thr His
    450                  455                 460
Gly Thr Asp Ile Pro Tyr Val Phe Tyr Asn Leu Asp Gly Leu Gly Tyr
465                  470                 475                  480
Asp Ser Asn Asn Lys Ser Ile Glu Ser Ile Pro Asn Ser Tyr Ser Arg
                485                  490                 495
Met Ser Lys Ile Met Ser Arg Met Trp Val Ser Phe Val Thr Thr Leu
            500                  505                 510
Asp Pro Asn His Ser Gly Gly Met Val Pro His Pro Ile Pro Met Ile
    515                  520                 525
Ala Gln Cys Gln Thr Arg Ala Glu Ser Thr Ile Phe Leu Gly Thr Asn
    530                  535                 540
Val Gln Trp Pro Pro Tyr Asn Ile Asp Asn Pro Glu Ile Ile Phe Phe
545                  550                 555                  560
Asp Thr Asp Val Thr Asn Leu Thr Tyr Thr Trp Pro Ala Gly Leu Tyr
                565                  570                 575
Ala His Trp Trp
        580

<210> SEQ ID NO 7
<211> LENGTH: 2769
<212> TYPE: DNA
<213> ORGANISM: Aspergillus niger

<400> SEQUENCE: 7
gtgaacaatg attagacttg agaacgtgg tctccgattg gaagtggact atctatttaa      60
tagtattgcc aaggctttct gatcggcaaa catattgtcc tcccgtggtg actggttct     120
cgcctgatgt gaatagtgat tatcaattta taccccttcgt cagcactgat tgaataagaa    180
cttacctcac attgccctca tttctatgct ggaaccatgc acctattttt aagccatccg    240
gccgatctta ctcacggtat gggctgactt tgtatcacaa cccatacctg tcgaccgtct    300
aaagtggggt cagtgacaag catgatgccg gtcagcatca tcagctcaac aaattctagc    360
caacaacgga gatcagtggt ccgacatttg atgtagaatt aaacccgcac acgtcggaat    420
ggcttcattc tcggtcttag tttcccaatc gaagctggtt cagcgcccag acgcggagcg    480
tggggggtggg acccccggatt ttccccccaca accttggctg tggttggcac ttttcatta    540
gcctccatcc tgtgcgcaga tactagagaa ctctacatca tgccatcgag gtttgttagt    600
tagatttgtt aactagctga gcggtgtagg tgcatgccgt acggtgagtt tgtctatctt    660
ttgtatagcc ggaagccgaa ggtaccccgc gtcatggcta tataaggctt gtatatccca    720
tgctctggta gatgggacaa caagaacggc gatccgatag aatcatggtg cagggtgtgg    780
cttttggact gctcgggctg gctgcctctg ctttgggcac ttatgcgccc tactacgcga    840
atttgacatg ggagcaacca cggactctgt ccaactggtc caaccttacc gtcgagacac    900
ggacagggac gttcattggt atgctcaatg acacttaccc agacgttcga cagtttctgc    960
gagttcctta tgccaaggta attctctcgc tgtacacatg tcatactgtg tctgacatga   1020
ccagcctcct attggggatt taagatggct tcctcctcat cggcttgaca actcaagcag   1080
aacatatgac tccaccttct atggcccagg taagtagtct tccatacaac tatgagcagt   1140
tccaattaac ccgagttcag cctgtccgca gtatgttcca gcagagagcg attttggaa    1200
```

-continued

```
tgaatatgaa ccggagaatt tgctgctcaa tgtcggcgaa aggctcaacc agggctctac      1260
ggcatggtcc tcgtcagagg attgcctgtc cctagcggta tggactccat cgtatgctaa      1320
tgagacatcc aagctgccag ttgcgctgtt tgtcacggga ggtggtggca tcacagggg       1380 tatcaacatt ccgtcccagc tgccctctgc ttgggtatct cgctctcagg agcatatcgt      1440
tgttaccatc aattaccgcg tcaatatttt tggcagtaag tatttgctct atatttgcaa      1500
atattagcct gacatgtata gatcccaaat cgcgtgcgtt gaatgatacg tcgcttacgc      1560
tgatggacgt gcgcgctgct gtggagtggg tatatgagaa cattgaagcg ttcggtggta      1620
atcccgaaaa tattatggtc agactacaag tttcctctca catgactaga gctaacagta      1680
agcagctatg gggacagtca caaggtgctt tgctgacgca tctgtacacc ctcgcatggc      1740
cagaagagcc tcttgccgcc aagttcggcg tcatctccca aggagcatct gccacactca      1800
acctctctac cacgcccgat gtgtaccaag actttgacat cgtggccaag ggactaggct      1860
gcaattatgg tgatgatgcc gaggccgagc tggagtgcat gcgtgggatt tcctgggtgc      1920
agatcgagga gtatatcaac cgctacaata gctctccttc tattgctttc acgaactata      1980
ttcgtatgta cccatcttgc tcttttaact gcccctacta caatatcag ccgatgagaa       2040 atacatcttc tccgacgaaa gacagcgtta ccttgagcgg aaggttgccc gaggcccgtc      2100
aattcgatct gacacggcgc gagaattccc tagcacaaac acgacctcag taaatattga      2160
agaaggcgaa tcagactgtc tggcagtgac tgaccttgcg ctacgtgcgt ccattgggct      2220
cgagacctat cgctactact gggctggtat gtccaatgac tttccatact gaagatagtg      2280
ctaacataaa caggcaactt ctccaatatc agtcccgtac cgtggctagg agcattccac      2340
tggaccgacc tgctgatgat cttcggtacg tataatctgg acgtcggcga gatctcgcag      2400
ttggaagtcg acacctctgc cacgatgcaa gattatctac tcgcctttct gaaggactca      2460
tcaaccgtca gcgagacggt cggatggccg ttatatctgg caacgagac caacggagga      2520 ctcatcctgg agttcggtaa cggcacagca gtgcggacca tcacaggtga ctggctcgac      2580
gcgggatgtt tcaattcatc tatcccattc agaatctggg ggtagcctat acacaccatc      2640
atcagagtag tatatacatc atatccacaa atccatctcc acctatatac ataaaccca       2700 actgaatcta caacagcgcc tggtccttct tcccctcccc ctctttaatt tccctcgcct      2760
tctccccat                                                              2769
```

<210> SEQ ID NO 8
<211> LENGTH: 1623
<212> TYPE: DNA
<213> ORGANISM: Aspergillus niger
<220> FEATURE:
<221> NAME/KEY: CDS
<222> LOCATION: (1)..(1623)

<400> SEQUENCE: 8

```
atg gtg cag ggt gtg gct ttt gga ctg ctc ggg ctg gct gcc tct gct          48
Met Val Gln Gly Val Ala Phe Gly Leu Leu Gly Leu Ala Ala Ser Ala
1               5                   10                  15 ttg ggc act tat gcg ccc tac tac gcg aat ttg aca tgg gag caa cca          96
Leu Gly Thr Tyr Ala Pro Tyr Tyr Ala Asn Leu Thr Trp Glu Gln Pro
            20                  25                  30 cgg act ctg tcc aac tgg tcc aac ctt acc gtc gag aca cgg aca ggg         144
Arg Thr Leu Ser Asn Trp Ser Asn Leu Thr Val Glu Thr Arg Thr Gly
        35                  40                  45 acg ttc att ggt atg ctc aat gac act tac cca gac gtt cga cag ttt         192
Thr Phe Ile Gly Met Leu Asn Asp Thr Tyr Pro Asp Val Arg Gln Phe
    50                  55                  60
```

```
ctg cga gtt cct tat gcc aag cct cct att ggg gat tta aga tgg ctt      240
Leu Arg Val Pro Tyr Ala Lys Pro Pro Ile Gly Asp Leu Arg Trp Leu
 65              70              75              80 cct cct cat cgg ctt gac aac tca agc aga aca tat gac tcc acc ttc      288
Pro Pro His Arg Leu Asp Asn Ser Ser Arg Thr Tyr Asp Ser Thr Phe
             85              90              95 tat ggc cca gcc tgt ccg cag tat gtt cca gca gag agc gat ttt tgg      336
Tyr Gly Pro Ala Cys Pro Gln Tyr Val Pro Ala Glu Ser Asp Phe Trp
            100             105             110 aat gaa tat gaa ccg gag aat ttg ctg ctc aat gtc ggc gaa agg ctc      384
Asn Glu Tyr Glu Pro Glu Asn Leu Leu Leu Asn Val Gly Glu Arg Leu
        115             120             125 aac cag ggc tct acg gca tgg tcc tcg tca gag gat tgc ctg tcc cta      432
Asn Gln Gly Ser Thr Ala Trp Ser Ser Ser Glu Asp Cys Leu Ser Leu
130             135             140 gcg gta tgg act cca tcg tat gct aat gag aca tcc aag ctg cca gtt      480
Ala Val Trp Thr Pro Ser Tyr Ala Asn Glu Thr Ser Lys Leu Pro Val
145             150             155             160 gcg ctg ttt gtc acg gga ggt ggt ggc atc aca ggg ggt atc aac att      528
Ala Leu Phe Val Thr Gly Gly Gly Gly Ile Thr Gly Gly Ile Asn Ile
                165             170             175 ccg tcc cag ctg ccc tct gct tgg gta tct cgc tct cag gag cat atc      576
Pro Ser Gln Leu Pro Ser Ala Trp Val Ser Arg Ser Gln Glu His Ile
            180             185             190 gtt gtt acc atc aat tac cgc gtc aat att ttt ggc aat ccc aaa tcg      624
Val Val Thr Ile Asn Tyr Arg Val Asn Ile Phe Gly Asn Pro Lys Ser
        195             200             205 cgt gcg ttg aat gat acg tcg ctt acg ctg atg gac gtg cgc gct gct      672
Arg Ala Leu Asn Asp Thr Ser Leu Thr Leu Met Asp Val Arg Ala Ala
    210             215             220 gtg gag tgg gta tat gag aac att gaa gcg ttc ggt ggt aat ccc gaa      720
Val Glu Trp Val Tyr Glu Asn Ile Glu Ala Phe Gly Gly Asn Pro Glu
225             230             235             240 aat att atg gtc aga cta caa gtt tcc tct cac atg act aga gct aac      768
Asn Ile Met Val Arg Leu Gln Val Ser Ser His Met Thr Arg Ala Asn
                245             250             255 agt aag cag cta tgg gga cag tca caa ggt gct ttg ctg acg cat ctg      816
Ser Lys Gln Leu Trp Gly Gln Ser Gln Gly Ala Leu Leu Thr His Leu
            260             265             270 tac acc ctc gca tgg cca gaa gag cct ctt gcc gcc aag ttc ggc gtc      864
Tyr Thr Leu Ala Trp Pro Glu Glu Pro Leu Ala Ala Lys Phe Gly Val
        275             280             285 atc tcc caa gga gca tct gcc aca ctc aac ctc tct acc acg ccc gat      912
Ile Ser Gln Gly Ala Ser Ala Thr Leu Asn Leu Ser Thr Thr Pro Asp
    290             295             300 gtg tac caa gac ttt gac atc gtg gcc aag gga cta ggc tgc aat tat      960
Val Tyr Gln Asp Phe Asp Ile Val Ala Lys Gly Leu Gly Cys Asn Tyr
305             310             315             320 ggt gat gat gcc gag gcc gag ctg gag tgc atg cgt ggg att tcc tgg     1008
Gly Asp Asp Ala Glu Ala Glu Leu Glu Cys Met Arg Gly Ile Ser Trp
                325             330             335 gtg cag atc gag gag tat atc aac cgc tac aat agc tct cct tct att     1056
Val Gln Ile Glu Glu Tyr Ile Asn Arg Tyr Asn Ser Ser Pro Ser Ile
            340             345             350 gct ttc acg aac tat att ccc gat gag aaa tac atc ttc tcc gac gaa     1104
Ala Phe Thr Asn Tyr Ile Pro Asp Glu Lys Tyr Ile Phe Ser Asp Glu
        355             360             365 aga cag cgt tac ctt gag cgg aag gtt gcc cga ggc ccg tca att cga     1152
Arg Gln Arg Tyr Leu Glu Arg Lys Val Ala Arg Gly Pro Ser Ile Arg
    370             375             380
```

```
tct gac acg gcg cga gaa ttc cct agc aca aac acg acc tca gta aat   1200
Ser Asp Thr Ala Arg Glu Phe Pro Ser Thr Asn Thr Thr Ser Val Asn
385                 390                 395                 400 att gaa gaa ggc gaa tca gac tgt ctg gca gtg act gac ctt gcg cta   1248
Ile Glu Glu Gly Glu Ser Asp Cys Leu Ala Val Thr Asp Leu Ala Leu
                405                 410                 415 cgt gcg tcc att ggg ctc gag acc tat cgc tac tac tgg gct ggc aac   1296
Arg Ala Ser Ile Gly Leu Glu Thr Tyr Arg Tyr Tyr Trp Ala Gly Asn
            420                 425                 430 ttc tcc aat atc agt ccc gta ccg tgg cta gga gca ttc cac tgg acc   1344
Phe Ser Asn Ile Ser Pro Val Pro Trp Leu Gly Ala Phe His Trp Thr
        435                 440                 445 gac ctg ctg atg atc ttc ggt acg tat aat ctg gac gtc ggc gag atc   1392
Asp Leu Leu Met Ile Phe Gly Thr Tyr Asn Leu Asp Val Gly Glu Ile
450                 455                 460 tcg cag ttg gaa gtc gac acc tct gcc acg atg caa gat tat cta ctc   1440
Ser Gln Leu Glu Val Asp Thr Ser Ala Thr Met Gln Asp Tyr Leu Leu
465                 470                 475                 480 gcc ttt ctg aag gac tca tca acc gtc agc gag acg gtc gga tgg ccg   1488
Ala Phe Leu Lys Asp Ser Ser Thr Val Ser Glu Thr Val Gly Trp Pro
                485                 490                 495 tta tat ctg ggc aac gag acc aac gga gga ctc atc ctg gag ttc ggt   1536
Leu Tyr Leu Gly Asn Glu Thr Asn Gly Gly Leu Ile Leu Glu Phe Gly
            500                 505                 510 aac ggc aca gca gtg cgg acc atc aca ggt gac tgg ctc gac gcg gga   1584
Asn Gly Thr Ala Val Arg Thr Ile Thr Gly Asp Trp Leu Asp Ala Gly
        515                 520                 525 tgt ttc aat tca tct atc cca ttc aga atc tgg ggg tag               1623
Cys Phe Asn Ser Ser Ile Pro Phe Arg Ile Trp Gly
530                 535                 540

<210> SEQ ID NO 9
<211> LENGTH: 540
<212> TYPE: PRT
<213> ORGANISM: Aspergillus niger

<400> SEQUENCE: 9

Met Val Gln Gly Val Ala Phe Gly Leu Leu Gly Leu Ala Ala Ser Ala
1               5                   10                  15

Leu Gly Thr Tyr Ala Pro Tyr Tyr Ala Asn Leu Thr Trp Glu Gln Pro
            20                  25                  30

Arg Thr Leu Ser Asn Trp Ser Asn Leu Thr Val Glu Thr Arg Thr Gly
        35                  40                  45

Thr Phe Ile Gly Met Leu Asn Asp Thr Tyr Pro Asp Val Arg Gln Phe
    50                  55                  60

Leu Arg Val Pro Tyr Ala Lys Pro Pro Ile Gly Asp Leu Arg Trp Leu
65                  70                  75                  80

Pro Pro His Arg Leu Asp Asn Ser Ser Arg Thr Tyr Asp Ser Thr Phe
                85                  90                  95

Tyr Gly Pro Ala Cys Pro Gln Tyr Val Pro Ala Glu Ser Asp Phe Trp
            100                 105                 110

Asn Glu Tyr Glu Pro Glu Asn Leu Leu Leu Asn Val Gly Glu Arg Leu
        115                 120                 125

Asn Gln Gly Ser Thr Ala Trp Ser Ser Ser Glu Asp Cys Leu Ser Leu
    130                 135                 140

Ala Val Trp Thr Pro Ser Tyr Ala Asn Glu Thr Ser Lys Leu Pro Val
145                 150                 155                 160

Ala Leu Phe Val Thr Gly Gly Gly Gly Ile Thr Gly Gly Ile Asn Ile
```

```
                    165                 170                 175
Pro Ser Gln Leu Pro Ser Ala Trp Val Ser Arg Ser Gln Glu His Ile
                180                 185                 190
Val Val Thr Ile Asn Tyr Arg Val Asn Ile Phe Gly Asn Pro Lys Ser
            195                 200                 205
Arg Ala Leu Asn Asp Thr Ser Leu Thr Leu Met Asp Val Arg Ala Ala
        210                 215                 220
Val Glu Trp Val Tyr Glu Asn Ile Glu Ala Phe Gly Gly Asn Pro Glu
225                 230                 235                 240
Asn Ile Met Val Arg Leu Gln Val Ser Ser His Met Thr Arg Ala Asn
                245                 250                 255
Ser Lys Gln Leu Trp Gly Gln Ser Gln Gly Ala Leu Leu Thr His Leu
            260                 265                 270
Tyr Thr Leu Ala Trp Pro Glu Pro Leu Ala Ala Lys Phe Gly Val
        275                 280                 285
Ile Ser Gln Gly Ala Ser Ala Thr Leu Asn Leu Ser Thr Thr Pro Asp
        290                 295                 300
Val Tyr Gln Asp Phe Asp Ile Val Ala Lys Gly Leu Gly Cys Asn Tyr
305                 310                 315                 320
Gly Asp Asp Ala Glu Ala Glu Leu Glu Cys Met Arg Gly Ile Ser Trp
                325                 330                 335
Val Gln Ile Glu Glu Tyr Ile Asn Arg Tyr Asn Ser Ser Pro Ser Ile
            340                 345                 350
Ala Phe Thr Asn Tyr Ile Pro Asp Glu Lys Tyr Ile Phe Ser Asp Glu
        355                 360                 365
Arg Gln Arg Tyr Leu Glu Arg Lys Val Ala Arg Gly Pro Ser Ile Arg
    370                 375                 380
Ser Asp Thr Ala Arg Glu Phe Pro Ser Thr Asn Thr Thr Ser Val Asn
385                 390                 395                 400
Ile Glu Glu Gly Glu Ser Asp Cys Leu Ala Val Thr Asp Leu Ala Leu
                405                 410                 415
Arg Ala Ser Ile Gly Leu Glu Thr Tyr Arg Tyr Tyr Trp Ala Gly Asn
            420                 425                 430
Phe Ser Asn Ile Ser Pro Val Pro Trp Leu Gly Ala Phe His Trp Thr
        435                 440                 445
Asp Leu Leu Met Ile Phe Gly Thr Tyr Asn Leu Asp Val Gly Glu Ile
        450                 455                 460
Ser Gln Leu Glu Val Asp Thr Ser Ala Thr Met Gln Asp Tyr Leu Leu
465                 470                 475                 480
Ala Phe Leu Lys Asp Ser Ser Thr Val Ser Glu Thr Val Gly Trp Pro
                485                 490                 495
Leu Tyr Leu Gly Asn Glu Thr Asn Gly Gly Leu Ile Leu Glu Phe Gly
            500                 505                 510
Asn Gly Thr Ala Val Arg Thr Ile Thr Gly Asp Trp Leu Asp Ala Gly
        515                 520                 525
Cys Phe Asn Ser Ser Ile Pro Phe Arg Ile Trp Gly
    530                 535                 540

<210> SEQ ID NO 10
<211> LENGTH: 3235
<212> TYPE: DNA
<213> ORGANISM: Aspergillus niger

<400> SEQUENCE: 10
gttttcaatt tggactgaat tttggcggca tttcttgtat aaaattaaaa ggggcgttga         60
```

```
ctggattttg gtacttggga tttattctta gctttgactg tacatagttt gggcgtggtt    120
tgatagccga cgatcggccg acccacgaac cagatttgca tatgattaca ttccttcaat    180
tttggtccga gtcccaaccc gcctttcaac cccaacaact acaagcacgt tgtgtttgct    240
acattgactc actcgatatt gctgaaccat gcaggccgcc caactgagtt attacaccaa    300
gcatgcgaat cggaaagttc gacaaagcgg gtgaaatgtc cgagttggcg aaccaaagcg    360
caacggtcga ggctcctttc cccgcagagg cagccattct gcagcctttg aactgcgggg    420
gaaacggcat ttgatcaact cggcactgat gcagtgacca acaggatgtt agcaatgttg    480
gcctaatata ttcttactga tctgctgata cgtccctccc ttgcatcagc ctcggtttgc    540
gcatgagaac gggttcgaac gttcctgggc cacccggttg gcgtgatatt ctccgcccac    600
gctgtctgtc cccctgatgg gaaaccttcg gatcagcgat catcaggcca gttggctatg    660
agaatagggg ctttgctgtc ttgatgccta aaatgcaggt ctcatagcaa gatccacagc    720
cgaggaggca catggcgatg tcgaaaccca tgggagctga tttttcggtt ctcggatcgt    780
gctccaagac atagaaggat attgagcact tgaaacgaag gggtgaaaaa tggaactgta    840
tatagagtta ctcccagccc gatccgagag cctatgaccc atagcggtac agatcatggc    900
catcatgaag gccctccttt ggctctccct ttccctcgcc gtctgggcga ctccagttca    960
acgggatgca gctcctactg tcactattgc gcatccatcg gccaccgtca ttggaaaatc   1020
tggcaatgtc gagagcttca acaatattcc ctttgcgcag gcccccacag gctcgctgcg   1080
tctgaagccc ccacaaccct tggaaactgc cctcggcact gttcaggcca caggagcctc   1140
gcaatcgtgt ccgcagatgt acttcaccac ggatgagagc gaattcccga catcggtcat   1200
tggcctcctc gctgatctcc ctttggtaca gtcggctacc aatgctctcg aggattgcct   1260
gaacattgac attcggcgtc cggccgggac caccgcggac tcgaagctgc ctgtgctggt   1320
ctggatcttt ggcggaggct ttgaacttgg ttcaaaggcg atgtatgatg gtacaacgat   1380
ggtatcatcg tcgatagaca agaacatgcc tatcgtgttt gtagcaatga attatcgcgt   1440
gggaggtttc gggttcttgc ccggaaagga gatcctggag gacgggtccg cgaacctagg   1500
gctcctggac caacgccttg ccctgcagtg ggttgccgac aacatcgagg cctttggtgg   1560
agacccggac aaggtgacga tttggggaga atcagcagga gccatttccg ttttttgatca   1620 gatgatcttg tacgacggaa acatcactta caaggataag cccttgttcc gggggggccat   1680 catggactcc ggtagtgttg ttcccgcaga ccccgtcgat ggggtcaagg gacagcaagt   1740
atatgatgcg gtagtggaat ctgcaggctg ttcctcttct aacgacaccc tagcttgtct   1800
gcgtgaacta gactacaccg acttcctcaa tgccggcaaac tccgtgccag gcattttaag   1860
ctaccattct gtggcgttat catatgtgcc tcgaccggac gggacggcgt tgtcggcatc   1920
accggacgtt ttgggcaaag cagggaaata tgctcgggtc ccgttcatcg tgggcgacca   1980
agaggatgag gggaccttat tcgccttgtt tcagtccaac attacgacga tcgacgaggt   2040
ggtcgactac ctggcctcat acttcttcta tgacgctagc cgagagcagc ttgaagaact   2100
agtggccctg tacccagaca ccaccacgta cgggtctccg ttcaggacag gcgcggccaa   2160
caactggtat ccgcaattta agcgattggc cgccattctc ggcgacttgg tcttcaccat   2220
tacccggcgg gcattcctct cgtatgcaga ggaaatctcc cctgatcttc gaactggtc   2280 gtacctggcg acctatgact atggcacccc agttctgggg accttccacg gaagtgacct   2340
gctgcaggtt ttctatggga tcaagccaaa ctatgcagct agttctagcc acacgtacta   2400
tctgagcttt gtgtatacgc tggatccgaa ctccaaccgg ggggagtaca ttgagtggcc   2460
```

```
gcagtggaag gaatcgcggc agttgatgaa tttcggagcg aacgacgcca gtctccttac    2520
ggatgatttc cgcaacggga catatgagtt catcctgcag aataccgcgg cgttccacat    2580
ctgatgccat tggcggaggg gtccggacgg tcaggaactt agccttatga gatgaatgat    2640
ggacgtgtct ggcctcggaa aaggatatat ggggatcatg atagtactag ccatattaat    2700
gaagggcata taccacgcgt tggacctgcg ttatagcttc ccgttagtta tagtaccatc    2760
gttataccag ccaatcaagt caccacgcac gaccggggac ggcgaatccc cgggaattga    2820
aagaaattgc atcccaggcc agtgaggcca gcgattggcc acctctccaa ggcacagggc    2880
cattctgcag cgctggtgga ttcatcgcaa tttcccccgg cccggcccga caccgctata    2940
ggctggttct cccacaccat cggagattcg tcgcctaatg tctcgtccgt tcacaagctg    3000
aagagcttga agtggcgaga tgtctctgca ggaattcaag ctagatgcta agcgatattg    3060
catggcaata tgtgttgatg catgtgcttc ttccttcagc ttcccctcgt gcagatgagg    3120
tttggctata aattgaagtg gttggtcggg gttccgtgag gggctgaagt gcttcctccc    3180
ttttagacgc aactgagagc ctgagcttca tccccagcat cattcaccct cagca        3235
```

```
<210> SEQ ID NO 11
<211> LENGTH: 1689
<212> TYPE: DNA
<213> ORGANISM: Aspergillus niger
<220> FEATURE:
<221> NAME/KEY: CDS
<222> LOCATION: (1)..(1689)

<400> SEQUENCE: 11
```

| | | | | | | | | | | | | | | | | |
|---|---|---|---|---|---|---|---|---|---|---|---|---|---|---|---|---|
| atg | gcc | atc | atg | aag | gcc | ctc | ctt | tgg | ctc | tcc | ctt | tcc | ctc | gcc | gtc | 48 |
| Met | Ala | Ile | Met | Lys | Ala | Leu | Leu | Trp | Leu | Ser | Leu | Ser | Leu | Ala | Val | |
| 1 | | | | 5 | | | | | 10 | | | | | 15 | | |

| tgg | gcg | act | cca | gtt | caa | cgg | gat | gca | gct | cct | act | gtc | act | att | gcg | 96 |
|---|---|---|---|---|---|---|---|---|---|---|---|---|---|---|---|---|
| Trp | Ala | Thr | Pro | Val | Gln | Arg | Asp | Ala | Ala | Pro | Thr | Val | Thr | Ile | Ala | |
| | | | 20 | | | | | 25 | | | | | 30 | | | |

| cat | cca | tcg | gcc | acc | gtc | att | gga | aaa | tct | ggc | aat | gtc | gag | agc | ttc | 144 |
|---|---|---|---|---|---|---|---|---|---|---|---|---|---|---|---|---|
| His | Pro | Ser | Ala | Thr | Val | Ile | Gly | Lys | Ser | Gly | Asn | Val | Glu | Ser | Phe | |
| | | 35 | | | | | 40 | | | | | 45 | | | | |

| aac | aat | att | ccc | ttt | gcg | cag | gcc | ccc | aca | ggc | tcg | ctg | cgt | ctg | aag | 192 |
|---|---|---|---|---|---|---|---|---|---|---|---|---|---|---|---|---|
| Asn | Asn | Ile | Pro | Phe | Ala | Gln | Ala | Pro | Thr | Gly | Ser | Leu | Arg | Leu | Lys | |
| 50 | | | | | 55 | | | | | 60 | | | | | | |

| ccc | cca | caa | ccc | ttg | gaa | act | gcc | ctc | ggc | act | gtt | cag | gcc | aca | gga | 240 |
|---|---|---|---|---|---|---|---|---|---|---|---|---|---|---|---|---|
| Pro | Pro | Gln | Pro | Leu | Glu | Thr | Ala | Leu | Gly | Thr | Val | Gln | Ala | Thr | Gly | |
| 65 | | | | 70 | | | | | 75 | | | | | 80 | | |

| gcc | tcg | caa | tcg | tgt | ccg | cag | atg | tac | ttc | acc | acg | gat | gag | agc | gaa | 288 |
|---|---|---|---|---|---|---|---|---|---|---|---|---|---|---|---|---|
| Ala | Ser | Gln | Ser | Cys | Pro | Gln | Met | Tyr | Phe | Thr | Thr | Asp | Glu | Ser | Glu | |
| | | | | 85 | | | | | 90 | | | | | 95 | | |

| ttc | ccg | aca | tcg | gtc | att | ggc | ctc | ctc | gct | gat | ctc | cct | ttg | gta | cag | 336 |
|---|---|---|---|---|---|---|---|---|---|---|---|---|---|---|---|---|
| Phe | Pro | Thr | Ser | Val | Ile | Gly | Leu | Leu | Ala | Asp | Leu | Pro | Leu | Val | Gln | |
| | | | 100 | | | | | 105 | | | | | 110 | | | |

| tcg | gct | acc | aat | gct | ctc | gag | gat | tgc | ctg | aac | att | gac | att | cgg | cgt | 384 |
|---|---|---|---|---|---|---|---|---|---|---|---|---|---|---|---|---|
| Ser | Ala | Thr | Asn | Ala | Leu | Glu | Asp | Cys | Leu | Asn | Ile | Asp | Ile | Arg | Arg | |
| | | 115 | | | | | 120 | | | | | 125 | | | | |

| ccg | gcc | ggg | acc | acc | gcg | gac | tcg | aag | ctg | cct | gtg | ctg | gtc | tgg | atc | 432 |
|---|---|---|---|---|---|---|---|---|---|---|---|---|---|---|---|---|
| Pro | Ala | Gly | Thr | Thr | Ala | Asp | Ser | Lys | Leu | Pro | Val | Leu | Val | Trp | Ile | |
| | 130 | | | | | 135 | | | | | 140 | | | | | |

| ttt | ggc | gga | ggc | ttt | gaa | ctt | ggt | tca | aag | gcg | atg | tat | gat | ggt | aca | 480 |
|---|---|---|---|---|---|---|---|---|---|---|---|---|---|---|---|---|
| Phe | Gly | Gly | Gly | Phe | Glu | Leu | Gly | Ser | Lys | Ala | Met | Tyr | Asp | Gly | Thr | |
| 145 | | | | | 150 | | | | | 155 | | | | | 160 | |

| acg | atg | gta | tca | tcg | tcg | ata | gac | aag | aac | atg | cct | atc | gtg | ttt | gta | 528 |
|---|---|---|---|---|---|---|---|---|---|---|---|---|---|---|---|---|
| Thr | Met | Val | Ser | Ser | Ser | Ile | Asp | Lys | Asn | Met | Pro | Ile | Val | Phe | Val | |

-continued

|  |  |  |  |  |  |  |  |  |  |  |  |  |  |  |  |
|---|---|---|---|---|---|---|---|---|---|---|---|---|---|---|---|

```
                       165                     170                     175
gca atg aat tat cgc gtg gga ggt ttc ggg ttc ttg ccc gga aag gag       576
Ala Met Asn Tyr Arg Val Gly Gly Phe Gly Phe Leu Pro Gly Lys Glu
            180                     185                     190 atc ctg gag gac ggg tcc gcg aac cta ggg ctc ctg gac caa cgc ctt       624
Ile Leu Glu Asp Gly Ser Ala Asn Leu Gly Leu Leu Asp Gln Arg Leu
            195                     200                     205 gcc ctg cag tgg gtt gcc gac aac atc gag gcc ttt ggt gga gac ccg       672
Ala Leu Gln Trp Val Ala Asp Asn Ile Glu Ala Phe Gly Gly Asp Pro
210                     215                     220 gac aag gtg acg att tgg gga gaa tca gca gga gcc att tcc gtt ttt       720
Asp Lys Val Thr Ile Trp Gly Glu Ser Ala Gly Ala Ile Ser Val Phe
225                     230                     235                     240 gat cag atg atc ttg tac gac gga aac atc act tac aag gat aag ccc       768
Asp Gln Met Ile Leu Tyr Asp Gly Asn Ile Thr Tyr Lys Asp Lys Pro
                245                     250                     255 ttg ttc cgg ggg gcc atc atg gac tcc ggt agt gtt gtt ccc gca gac       816
Leu Phe Arg Gly Ala Ile Met Asp Ser Gly Ser Val Val Pro Ala Asp
                260                     265                     270 ccc gtc gat ggg gtc aag gga cag caa gta tat gat gcg gta gtg gaa       864
Pro Val Asp Gly Val Lys Gly Gln Gln Val Tyr Asp Ala Val Val Glu
            275                     280                     285 tct gca ggc tgt tcc tct tct aac gac acc cta gct tgt ctg cgt gaa       912
Ser Ala Gly Cys Ser Ser Ser Asn Asp Thr Leu Ala Cys Leu Arg Glu
            290                     295                     300 cta gac tac acc gac ttc ctc aat gcg gca aac tcc gtg cca ggc att       960
Leu Asp Tyr Thr Asp Phe Leu Asn Ala Ala Asn Ser Val Pro Gly Ile
305                     310                     315                     320 tta agc tac cat tct gtg gcg tta tca tat gtg cct cga ccg gac ggg      1008
Leu Ser Tyr His Ser Val Ala Leu Ser Tyr Val Pro Arg Pro Asp Gly
                325                     330                     335 acg gcg ttg tcg gca tca ccg gac gtt ttg ggc aaa gca ggg aaa tat      1056
Thr Ala Leu Ser Ala Ser Pro Asp Val Leu Gly Lys Ala Gly Lys Tyr
                340                     345                     350 gct cgg gtc ccg ttc atc gtg ggc gac caa gag gat gag ggg acc tta      1104
Ala Arg Val Pro Phe Ile Val Gly Asp Gln Glu Asp Glu Gly Thr Leu
            355                     360                     365 ttc gcc ttg ttt cag tcc aac att acg acg atc gac gag gtg gtc gac      1152
Phe Ala Leu Phe Gln Ser Asn Ile Thr Thr Ile Asp Glu Val Val Asp
370                     375                     380 tac ctg gcc tca tac ttc ttc tat gac gct agc cga gag cag ctt gaa      1200
Tyr Leu Ala Ser Tyr Phe Phe Tyr Asp Ala Ser Arg Glu Gln Leu Glu
385                     390                     395                     400 gaa cta gtg gcc ctg tac cca gac acc acg tac ggg tct ccg ttc          1248
Glu Leu Val Ala Leu Tyr Pro Asp Thr Thr Thr Tyr Gly Ser Pro Phe
                405                     410                     415 agg aca ggc gcg gcc aac aac tgg tat ccg caa ttt aag cga ttg gcc      1296
Arg Thr Gly Ala Ala Asn Asn Trp Tyr Pro Gln Phe Lys Arg Leu Ala
                420                     425                     430 gcc att ctc ggc gac ttg gtc ttc acc att acc cgg cgg gca ttc ctc      1344
Ala Ile Leu Gly Asp Leu Val Phe Thr Ile Thr Arg Arg Ala Phe Leu
            435                     440                     445 tcg tat gca gag gaa atc tcc cct gat ctt ccg aac tgg tcg tac ctg      1392
Ser Tyr Ala Glu Glu Ile Ser Pro Asp Leu Pro Asn Trp Ser Tyr Leu
450                     455                     460 gcg acc tat gac tat ggc acc cca gtt ctg ggg acc ttc cac gga agt      1440
Ala Thr Tyr Asp Tyr Gly Thr Pro Val Leu Gly Thr Phe His Gly Ser
465                     470                     475                     480 gac ctg ctg cag gtg ttc tat ggg atc aag cca aac tat gca gct agt      1488
Asp Leu Leu Gln Val Phe Tyr Gly Ile Lys Pro Asn Tyr Ala Ala Ser
```

```
                      485                 490                 495
tct agc cac acg tac tat ctg agc ttt gtg tat acg ctg gat ccg aac    1536
Ser Ser His Thr Tyr Tyr Leu Ser Phe Val Tyr Thr Leu Asp Pro Asn
            500                 505                 510 tcc aac cgg ggg gag tac att gag tgg ccg cag tgg aag gaa tcg cgg    1584
Ser Asn Arg Gly Glu Tyr Ile Glu Trp Pro Gln Trp Lys Glu Ser Arg
        515                 520                 525 cag ttg atg aat ttc gga gcg aac gac gcc agt ctc ctt acg gat gat    1632
Gln Leu Met Asn Phe Gly Ala Asn Asp Ala Ser Leu Leu Thr Asp Asp
530                 535                 540 ttc cgc aac ggg aca tat gag ttc atc ctg cag aat acc gcg gcg ttc    1680
Phe Arg Asn Gly Thr Tyr Glu Phe Ile Leu Gln Asn Thr Ala Ala Phe
545                 550                 555                 560 cac atc tga                                                         1689
His Ile <210> SEQ ID NO 12
<211> LENGTH: 562
<212> TYPE: PRT
<213> ORGANISM: Aspergillus niger

<400> SEQUENCE: 12

Met Ala Ile Met Lys Ala Leu Leu Trp Leu Ser Leu Ser Leu Ala Val
1               5                   10                  15

Trp Ala Thr Pro Val Gln Arg Asp Ala Ala Pro Thr Val Thr Ile Ala
            20                  25                  30

His Pro Ser Ala Thr Val Ile Gly Lys Ser Gly Asn Val Glu Ser Phe
        35                  40                  45

Asn Asn Ile Pro Phe Ala Gln Ala Pro Thr Gly Ser Leu Arg Leu Lys
    50                  55                  60

Pro Pro Gln Pro Leu Glu Thr Ala Leu Gly Thr Val Gln Ala Thr Gly
65                  70                  75                  80

Ala Ser Gln Ser Cys Pro Gln Met Tyr Phe Thr Thr Asp Glu Ser Glu
                85                  90                  95

Phe Pro Thr Ser Val Ile Gly Leu Leu Ala Asp Leu Pro Leu Val Gln
            100                 105                 110

Ser Ala Thr Asn Ala Leu Glu Asp Cys Leu Asn Ile Asp Ile Arg Arg
        115                 120                 125

Pro Ala Gly Thr Thr Ala Asp Ser Lys Leu Pro Val Leu Val Trp Ile
    130                 135                 140

Phe Gly Gly Gly Phe Glu Leu Gly Ser Lys Ala Met Tyr Asp Gly Thr
145                 150                 155                 160

Thr Met Val Ser Ser Ile Asp Lys Asn Met Pro Ile Val Phe Val
                165                 170                 175

Ala Met Asn Tyr Arg Val Gly Gly Phe Gly Phe Leu Pro Gly Lys Glu
            180                 185                 190

Ile Leu Glu Asp Gly Ser Ala Asn Leu Gly Leu Leu Asp Gln Arg Leu
        195                 200                 205

Ala Leu Gln Trp Val Ala Asp Asn Ile Glu Ala Phe Gly Gly Asp Pro
    210                 215                 220

Asp Lys Val Thr Ile Trp Gly Glu Ser Ala Gly Ala Ile Ser Val Phe
225                 230                 235                 240

Asp Gln Met Ile Leu Tyr Asp Gly Asn Ile Thr Tyr Lys Asp Lys Pro
                245                 250                 255

Leu Phe Arg Gly Ala Ile Met Asp Ser Gly Ser Val Val Pro Ala Asp
            260                 265                 270
```

```
Pro Val Asp Gly Val Lys Gly Gln Gln Val Tyr Asp Ala Val Val Glu
    275                 280                 285

Ser Ala Gly Cys Ser Ser Asn Asp Thr Leu Ala Cys Leu Arg Glu
    290                 295                 300

Leu Asp Tyr Thr Asp Phe Leu Asn Ala Ala Asn Ser Val Pro Gly Ile
305                 310                 315                 320

Leu Ser Tyr His Ser Val Ala Leu Ser Tyr Val Pro Arg Pro Asp Gly
                325                 330                 335

Thr Ala Leu Ser Ala Ser Pro Asp Val Leu Gly Lys Ala Gly Lys Tyr
                340                 345                 350

Ala Arg Val Pro Phe Ile Val Gly Asp Gln Asp Glu Gly Thr Leu
            355                 360                 365

Phe Ala Leu Phe Gln Ser Asn Ile Thr Thr Ile Asp Glu Val Val Asp
370                 375                 380

Tyr Leu Ala Ser Tyr Phe Phe Tyr Asp Ala Ser Arg Glu Gln Leu Glu
385                 390                 395                 400

Glu Leu Val Ala Leu Tyr Pro Asp Thr Thr Tyr Gly Ser Pro Phe
            405                 410                 415

Arg Thr Gly Ala Ala Asn Asn Trp Tyr Pro Gln Phe Lys Arg Leu Ala
            420                 425                 430

Ala Ile Leu Gly Asp Leu Val Phe Thr Ile Thr Arg Arg Ala Phe Leu
            435                 440                 445

Ser Tyr Ala Glu Glu Ile Ser Pro Asp Leu Pro Asn Trp Ser Tyr Leu
            450                 455                 460

Ala Thr Tyr Asp Tyr Gly Thr Pro Val Leu Gly Thr Phe His Gly Ser
465                 470                 475                 480

Asp Leu Leu Gln Val Phe Tyr Gly Ile Lys Pro Asn Tyr Ala Ala Ser
                485                 490                 495

Ser Ser His Thr Tyr Tyr Leu Ser Phe Val Tyr Thr Leu Asp Pro Asn
            500                 505                 510

Ser Asn Arg Gly Glu Tyr Ile Glu Trp Pro Gln Trp Lys Glu Ser Arg
            515                 520                 525

Gln Leu Met Asn Phe Gly Ala Asn Asp Ala Ser Leu Leu Thr Asp Asp
    530                 535                 540

Phe Arg Asn Gly Thr Tyr Glu Phe Ile Leu Gln Asn Thr Ala Ala Phe
545                 550                 555                 560

His Ile

<210> SEQ ID NO 13
<211> LENGTH: 2097
<212> TYPE: DNA
<213> ORGANISM: Aspergillus niger

<400> SEQUENCE: 13
cctggctgac gctataccga agacgatgtc gatgtcgtct ttgctcagag gccccgagtc     60
gtttggggca cgtcaagaaa gtagtcttcg ctgctgcttg aagacatgat caggacacgc    120
ggttcgacct tcgagtgtac atgatatccg tagaatttgc ttgtgactac caaggcatat    180
gttagttcgt gcagtggtaa aagcggcttc tcttcttcaa tctgcgaggt ggagatgcct    240
actatgatcg tcatccaact tggtgtctac aagacgaaca caagcttagt tccgacgaac    300
cagtgaaaac tctgtaagat atataagagc atcaagagtc ggacttgctt aggagagtgg    360
atagttgttg atgctcgcgg aagctctcat atagtataga tatgaagtat cggtgagtcg    420
tagtagtctt tgtattatat agggagaggc tgaatggtgt gggtcatgat aatttccaca    480
```

-continued

```
taatagcgat taaagcccta gatcgagggt atcttgaggc ataaatgata gtatcagtgg    540
acatatcctg agatgaggat gatatgagat gatagagatg aggaagaaag aggaaagaga    600
gaggcaagaa cagagatttt tataccttg cagagcagcc catccgtcac tgaattcagg     660
catcttcact ccatactatc acgagtcaac gtgaagttgt ataagcgtag tgacaggccg    720
cagtgacgat gatccgtcac tgcggtggct atccgcgact gatcttgcta ccgtgactg     780 cgttgactct ggtgaaccaa gtgttcggga aggggtgaaa atgaagctga agcgggtcag    840
ggaacattcc aagcaacact agacgagtca gcgacgagtc agcgatccac tcggtctcac    900
acgctcccaa tagtctcaat ttggtgccaa tggcaactaa gtattccatc cactttaat    960 taaagtgatc agcggtgcac gaattcacat gctggatctg gtacagatca gattaatatc    1020
tcctggaata cgatgaaggc ccacctcagg attcacgata aatttctggt gactgccagc    1080
tcgaatggca ttctccgtca ctctacacct gccgttggtt aattctccga acctctaatt   1140
gtcaatttct gccaaaatgc gtctatcatc gctggccctg catccagcg ccatcctacc    1200 cgccttaggc tacagcatca acgacttctc ctgcaatagc accgaacacc cgaatccagt    1260
tgtgctccta catgggctag cgccaccta ctacgaagac ttgaattacc tgcaaggttg     1320
gctacagacc caaggctatt gcacttacgc caaaacctac ggtgcatatg aaggcttccc    1380
ctttgtcggc ggcctcaagg ccatcgccga atcggcacg gaaatcgccg cgtacatccg     1440
cgaggtgaaa gaaaagacgg gcgccgacaa gattgacctt gtcggtcact ccgaaggcgc    1500
cttccagacc ctctacgtcc ctaagttcga ggatggtatc tcggagatgc tggataagct    1560
ggtggccatt gcacctccca ccagaggcac caacttggcg gggatctatg acatcgcata    1620
tgttctggga aatctatcgc gcgatctgat aggcgacgtc ctggatacog tgggctgcgc    1680 cgcctgtgat gatctgggtc cggatggagc agcgattgac cgcttgaacg atggcgagcc    1740
tatcgtgcag ccgggaaata atctaacggt gattgcatcg cggtccgacg aattggtcac    1800
cccaaccacc acctccttcg tgcatgaaga tggggtgacc aatgaatggg tgcaagacac    1860
ttgtcctcta gaccctgtcg gtcatatcgg tgaggcatac gatctgaacg tctggaattt    1920
ggtcaaaaac gccttggact ctacgccgaa gcgtgagttc gtctgctcgc tgggatctcc    1980
cggcaggtga gactatcatc ttctgaaaat ttgtatataa gcatttatat ttggataccc    2040
ggttaccagt cattagtgtc ataatgtata ataatcac cacaacttcc tccaagc        2097
```

<210> SEQ ID NO 14
<211> LENGTH: 834
<212> TYPE: DNA
<213> ORGANISM: Aspergillus niger
<220> FEATURE:
<221> NAME/KEY: CDS
<222> LOCATION: (1)..(834)

<400> SEQUENCE: 14

```
atg cgt cta tca tcg ctg gcc ctg gca tcc agc gcc atc cta ccc gcc       48
Met Arg Leu Ser Ser Leu Ala Leu Ala Ser Ser Ala Ile Leu Pro Ala
1               5                   10                  15 tta ggc tac agc atc aac gac ttc tcc tgc aat agc acc gaa cac ccg       96
Leu Gly Tyr Ser Ile Asn Asp Phe Ser Cys Asn Ser Thr Glu His Pro
            20                  25                  30 aat cca gtt gtg ctc cta cat ggg cta ggc gcc acc tac tac gaa gac      144
Asn Pro Val Val Leu Leu His Gly Leu Gly Ala Thr Tyr Tyr Glu Asp
        35                  40                  45 ttg aat tac ctg caa ggt tgg cta cag acc caa ggc tat tgc act tac      192
Leu Asn Tyr Leu Gln Gly Trp Leu Gln Thr Gln Gly Tyr Cys Thr Tyr
    50                  55                  60
```

-continued

|  |  |  |  |  |  |  |  |  |  |  |  |  |  |  |  |  |
|---|---|---|---|---|---|---|---|---|---|---|---|---|---|---|---|---|
| gcc | aaa | acc | tac | ggt | gca | tat | gaa | ggc | ttc | ccc | ttt | gtc | ggc | ggc | ctc | 240 |
| Ala | Lys | Thr | Tyr | Gly | Ala | Tyr | Glu | Gly | Phe | Pro | Phe | Val | Gly | Gly | Leu |  |
| 65 |  |  |  | 70 |  |  |  |  | 75 |  |  |  |  |  | 80 |  |
| aag | gcc | atc | gcc | gaa | tcg | gcc | acg | gaa | atc | gcc | gcg | tac | atc | cgc | gag | 288 |
| Lys | Ala | Ile | Ala | Glu | Ser | Ala | Thr | Glu | Ile | Ala | Ala | Tyr | Ile | Arg | Glu |  |
|  |  |  |  |  | 85 |  |  |  |  | 90 |  |  |  |  | 95 |  |
| gtg | aaa | gaa | aag | acg | ggc | gcc | gac | aag | att | gac | ctt | gtc | ggt | cac | tcc | 336 |
| Val | Lys | Glu | Lys | Thr | Gly | Ala | Asp | Lys | Ile | Asp | Leu | Val | Gly | His | Ser |  |
|  |  |  | 100 |  |  |  |  | 105 |  |  |  |  | 110 |  |  |  |
| gaa | ggc | gcc | ttc | cag | acc | ctc | tac | gtc | cct | aag | ttc | gag | gat | ggt | atc | 384 |
| Glu | Gly | Ala | Phe | Gln | Thr | Leu | Tyr | Val | Pro | Lys | Phe | Glu | Asp | Gly | Ile |  |
|  |  | 115 |  |  |  |  | 120 |  |  |  |  | 125 |  |  |  |  |
| tcg | gag | atg | ctg | gat | aag | ctg | gtg | gcc | att | gca | cct | ccc | acc | aga | ggc | 432 |
| Ser | Glu | Met | Leu | Asp | Lys | Leu | Val | Ala | Ile | Ala | Pro | Pro | Thr | Arg | Gly |  |
| 130 |  |  |  |  | 135 |  |  |  |  | 140 |  |  |  |  |  |  |
| acc | aac | ttg | gcg | ggg | atc | tat | gac | atc | gca | tat | gtt | ctg | gga | aat | cta | 480 |
| Thr | Asn | Leu | Ala | Gly | Ile | Tyr | Asp | Ile | Ala | Tyr | Val | Leu | Gly | Asn | Leu |  |
| 145 |  |  |  |  | 150 |  |  |  |  | 155 |  |  |  |  | 160 |  |
| tcg | cgc | gat | ctg | ata | ggc | gac | gtc | ctg | gat | acc | gtg | ggc | tgc | gcc | gcc | 528 |
| Ser | Arg | Asp | Leu | Ile | Gly | Asp | Val | Leu | Asp | Thr | Val | Gly | Cys | Ala | Ala |  |
|  |  |  |  | 165 |  |  |  |  | 170 |  |  |  |  | 175 |  |  |
| tgt | gat | gat | ctg | ggt | ccg | gat | gga | gca | gcg | att | gac | cgc | ttg | aac | gat | 576 |
| Cys | Asp | Asp | Leu | Gly | Pro | Asp | Gly | Ala | Ala | Ile | Asp | Arg | Leu | Asn | Asp |  |
|  |  | 180 |  |  |  |  | 185 |  |  |  |  | 190 |  |  |  |  |
| ggc | gag | cct | atc | gtg | cag | ccg | gga | aat | aat | cta | acg | gtg | att | gca | tcg | 624 |
| Gly | Glu | Pro | Ile | Val | Gln | Pro | Gly | Asn | Asn | Leu | Thr | Val | Ile | Ala | Ser |  |
|  | 195 |  |  |  |  | 200 |  |  |  |  | 205 |  |  |  |  |  |
| cgg | tcc | gac | gaa | ttg | gtc | acc | cca | acc | acc | acc | tcc | ttc | gtg | cat | gaa | 672 |
| Arg | Ser | Asp | Glu | Leu | Val | Thr | Pro | Thr | Thr | Thr | Ser | Phe | Val | His | Glu |  |
| 210 |  |  |  |  | 215 |  |  |  |  | 220 |  |  |  |  |  |  |
| gat | ggg | gtg | acc | aat | gaa | tgg | gtg | caa | gac | act | tgt | cct | cta | gac | cct | 720 |
| Asp | Gly | Val | Thr | Asn | Glu | Trp | Val | Gln | Asp | Thr | Cys | Pro | Leu | Asp | Pro |  |
| 225 |  |  |  |  | 230 |  |  |  |  | 235 |  |  |  |  | 240 |  |
| gtc | ggt | cat | atc | ggt | gag | gca | tac | gat | ctg | aac | gtc | tgg | aat | ttg | gtc | 768 |
| Val | Gly | His | Ile | Gly | Glu | Ala | Tyr | Asp | Leu | Asn | Val | Trp | Asn | Leu | Val |  |
|  |  |  |  | 245 |  |  |  |  | 250 |  |  |  |  | 255 |  |  |
| aaa | aac | gcc | ttg | gac | tct | acg | ccg | aag | cgt | gag | ttc | gtc | tgc | tcg | ctg | 816 |
| Lys | Asn | Ala | Leu | Asp | Ser | Thr | Pro | Lys | Arg | Glu | Phe | Val | Cys | Ser | Leu |  |
|  |  | 260 |  |  |  |  | 265 |  |  |  |  | 270 |  |  |  |  |
| gga | tct | ccc | ggc | agg | tga |  |  |  |  |  |  |  |  |  |  | 834 |
| Gly | Ser | Pro | Gly | Arg |  |  |  |  |  |  |  |  |  |  |  |  |
|  | 275 |  |  |  |  |  |  |  |  |  |  |  |  |  |  |  |

<210> SEQ ID NO 15
<211> LENGTH: 277
<212> TYPE: PRT
<213> ORGANISM: Aspergillus niger

<400> SEQUENCE: 15

Met Arg Leu Ser Ser Leu Ala Leu Ala Ser Ser Ala Ile Leu Pro Ala
1               5                   10                  15

Leu Gly Tyr Ser Ile Asn Asp Phe Ser Cys Asn Ser Thr Glu His Pro
            20                  25                  30

Asn Pro Val Val Leu Leu His Gly Leu Gly Ala Thr Tyr Tyr Glu Asp
        35                  40                  45

Leu Asn Tyr Leu Gln Gly Trp Leu Gln Thr Gln Gly Tyr Cys Thr Tyr
    50                  55                  60

Ala Lys Thr Tyr Gly Ala Tyr Glu Gly Phe Pro Phe Val Gly Gly Leu
65                  70                  75                  80

Lys Ala Ile Ala Glu Ser Ala Thr Glu Ile Ala Ala Tyr Ile Arg Glu
            85                  90                  95

Val Lys Glu Lys Thr Gly Ala Asp Lys Ile Asp Leu Val Gly His Ser
        100                 105                 110

Glu Gly Ala Phe Gln Thr Leu Tyr Val Pro Lys Phe Glu Asp Gly Ile
        115                 120                 125

Ser Glu Met Leu Asp Lys Leu Val Ala Ile Ala Pro Pro Thr Arg Gly
        130                 135                 140

Thr Asn Leu Ala Gly Ile Tyr Asp Ile Ala Tyr Val Leu Gly Asn Leu
145                 150                 155                 160

Ser Arg Asp Leu Ile Gly Asp Val Leu Asp Thr Val Gly Cys Ala Ala
                165                 170                 175

Cys Asp Asp Leu Gly Pro Asp Gly Ala Ala Ile Asp Arg Leu Asn Asp
            180                 185                 190

Gly Glu Pro Ile Val Gln Pro Gly Asn Asn Leu Thr Val Ile Ala Ser
            195                 200                 205

Arg Ser Asp Glu Leu Val Thr Pro Thr Thr Thr Ser Phe Val His Glu
    210                 215                 220

Asp Gly Val Thr Asn Glu Trp Val Gln Asp Thr Cys Pro Leu Asp Pro
225                 230                 235                 240

Val Gly His Ile Gly Glu Ala Tyr Asp Leu Asn Val Trp Asn Leu Val
                245                 250                 255

Lys Asn Ala Leu Asp Ser Thr Pro Lys Arg Glu Phe Val Cys Ser Leu
            260                 265                 270

Gly Ser Pro Gly Arg
            275

<210> SEQ ID NO 16
<211> LENGTH: 1881
<212> TYPE: DNA
<213> ORGANISM: Aspergillus niger

<400> SEQUENCE: 16
ccgagtgatc cgcgacttct gggtcagctt tgttctgcgg gctccaccag tgccgtcatc      60
gcacgcgaga cccgccccgg atgcttagct gaagccggca tagtccatcc ccgctcgggc     120
gtgatgccca acggtcactg gaggagaggt gcagggagga tgccgttgca tgaatcaagc     180
ccggggtttg actttcatcc gctcgttccc tactggcggg ttcgccctct ccatcgaagc     240
cacggatcct tccatccgga tcctggcaga acagtgagga agcagagctt ggttatagta     300
gaaattatta ataccgagct ggtctgccca ttttccaa accttccctc tttccatccc       360
tctcgcctcg caccccttt atcctccctc ccgccatgta tatccctcg gtgctgcttc       420 tggccgcgag cctgttccat ggcgcaacgg cgctgcccac gcccggctcc acgcccatcc     480
cgcccagcca ggatccctgg tacagtgcgc ccgagggctt cgaggaggct gatcccggtg     540
ccatcctgcg cgtgcggccc gcgcccggca acttgaccgt ggtagtgggc aatgcgtcgg     600
cggcctacaa catcctctac cgcactacag acagtcagta caagccctcc tgggctgtga     660
ccaccctgct ggtgccccc gtggccgcct cgccgccgt caaccagagt gtcctgctct       720
cccaccagat cgcctacgat tcgttcgacg tcaatgccag tcccagctac gccatgtaca     780
ccagcccgcc ctccgatatt atcctcgccc tgcagcgcgg ctggttcgtt aacgtccccg     840
attacgaggg ccccaatgcc tctttcaccg ccggtgtgca gtccggccat gccaccctcg     900
actcggtccg cagcgtgctc gcctccggat tcggcctgaa cgaggacgcc cagtacgctc     960
tgtggggtta ctctggcggt gccttggcca gcgaatgggc tgctgaactg cagatgcaat    1020

-continued

```
acgctcccga gttgaacatt gccggtctgg ccgtgggtgg tctcactccc aatgttacca    1080
gcgtcatgga cacggtgacc tcgaccatca gtgcgggact catccccgcc gccgccctgg    1140
gtctgtcgag ccagcacccc gagacctacg agttcatcct cagccagctc aagacgacgg    1200
gaccctacaa ccgcacagga ttcctagccg ccaaggacct gaccctgtcc gaggcggagg    1260
tcttctacgc cttccagaac atcttcgatt actttgtcaa cggatcggcc acgttccagg    1320
cggaggtggt gcagaaggcg ctgaaccagg acggatacat gggctaccat gggttcccgc    1380
agatgccggt gctcgcgtac aaggctattc acgatgagat cagtcccatc caggatacgg    1440
atcgcgtgat caagcgctac tgtggtctgg gattgaacat cttgtatgag cggaacacca    1500
tcggtggcca ctcggcagag caggtgaatg caacgccag ggcgtggaac tggttgacga    1560
gcattttcga cggaacgtat gcgcagcagt acaagaccga ggggtgcacg atccgcaatg    1620
tcactctgaa cacgacttcc tccgtttatt agagagggg ctgttgttat gtgaataatg    1680
ctgaagatgg ctgtgtatgg acggtccgct ctcctgtata gtaatgggct aatgcatgcg    1740
gcttcatgaa catggtacga aagattagat tatgtatata gtgtggaagt ggtaatgatg    1800
atataatatc tgtctatgat ctatgttcct gctattctat acaaacgcga ccattcacag    1860
aatgactact ggcacatctg c                                              1881

<210> SEQ ID NO 17
<211> LENGTH: 1257
<212> TYPE: DNA
<213> ORGANISM: Aspergillus niger
<220> FEATURE:
<221> NAME/KEY: CDS
<222> LOCATION: (1)..(1257)

<400> SEQUENCE: 17 atg tat atc ccc tcg gtg ctg ctt ctg gcc gcg agc ctg ttc cat ggc    48
Met Tyr Ile Pro Ser Val Leu Leu Leu Ala Ala Ser Leu Phe His Gly
1               5                   10                  15 gca acg gcg ctg ccc acg ccc ggc tcc acg ccc atc ccg ccc agc cag    96
Ala Thr Ala Leu Pro Thr Pro Gly Ser Thr Pro Ile Pro Pro Ser Gln
            20                  25                  30 gat ccc tgg tac agt gcg ccc gag ggc ttc gag gag gct gat ccc ggt   144
Asp Pro Trp Tyr Ser Ala Pro Glu Gly Phe Glu Glu Ala Asp Pro Gly
        35                  40                  45 gcc atc ctg cgc gtg cgg ccc gcg ccc ggc aac ttg acc gtg gta gtg   192
Ala Ile Leu Arg Val Arg Pro Ala Pro Gly Asn Leu Thr Val Val Val
    50                  55                  60 ggc aat gcg tcg gcg gcc tac aac atc ctc tac cgc act aca gac agt   240
Gly Asn Ala Ser Ala Ala Tyr Asn Ile Leu Tyr Arg Thr Thr Asp Ser
65                  70                  75                  80 cag tac aag ccc tcc tgg gct gtg acc acc ctg ctg gtg ccc ccc gtg   288
Gln Tyr Lys Pro Ser Trp Ala Val Thr Thr Leu Leu Val Pro Pro Val
                85                  90                  95 gcc gcc tcc gcc gcc gtc aac cag agt gtc ctg ctc tcc cac cag atc   336
Ala Ala Ser Ala Ala Val Asn Gln Ser Val Leu Leu Ser His Gln Ile
            100                 105                 110 gcc tac gat tcg ttc gac gtc aat gcc agt ccc agc tac gcc atg tac   384
Ala Tyr Asp Ser Phe Asp Val Asn Ala Ser Pro Ser Tyr Ala Met Tyr
        115                 120                 125 acc agc ccg ccc tcc gat att atc ctc gcc ctg cag cgc ggc tgg ttc   432
Thr Ser Pro Pro Ser Asp Ile Ile Leu Ala Leu Gln Arg Gly Trp Phe
    130                 135                 140 gtt aac gtc ccc gat tac gag ggc ccc aat gcc tct ttc acc gcc ggt   480
Val Asn Val Pro Asp Tyr Glu Gly Pro Asn Ala Ser Phe Thr Ala Gly
```

```
                    145                 150                 155                 160
gtg cag tcc ggc cat gcc acc ctc gac tcg gtc cgc agc gtg ctc gcc       528
Val Gln Ser Gly His Ala Thr Leu Asp Ser Val Arg Ser Val Leu Ala
                165                 170                 175 tcc gga ttc ggc ctg aac gag gac gcc cag tac gct ctg tgg ggt tac       576
Ser Gly Phe Gly Leu Asn Glu Asp Ala Gln Tyr Ala Leu Trp Gly Tyr
            180                 185                 190 tct ggc ggt gcc ttg gcc agc gaa tgg gct gct gaa ctg cag atg caa       624
Ser Gly Gly Ala Leu Ala Ser Glu Trp Ala Ala Glu Leu Gln Met Gln
        195                 200                 205 tac gct ccc gag ttg aac att gcc ggt ctg gcc gtg ggt ggt ctc act       672
Tyr Ala Pro Glu Leu Asn Ile Ala Gly Leu Ala Val Gly Gly Leu Thr
    210                 215                 220 ccc aat gtt acc agc gtc atg gac acg gtg acc tcg acc atc agt gcg       720
Pro Asn Val Thr Ser Val Met Asp Thr Val Thr Ser Thr Ile Ser Ala
225                 230                 235                 240 gga ctc atc ccc gcc gcc gcc ctg ggt ctg tcg agc cag cac ccc gag       768
Gly Leu Ile Pro Ala Ala Ala Leu Gly Leu Ser Ser Gln His Pro Glu
                245                 250                 255 acc tac gag ttc atc ctc agc cag ctc aag acg acg gga ccc tac aac       816
Thr Tyr Glu Phe Ile Leu Ser Gln Leu Lys Thr Thr Gly Pro Tyr Asn
            260                 265                 270 cgc aca gga ttc cta gcc gcc aag gac ctg acc ctg tcc gag gcg gag       864
Arg Thr Gly Phe Leu Ala Ala Lys Asp Leu Thr Leu Ser Glu Ala Glu
        275                 280                 285 gtc ttc tac gcc ttc cag aac atc ttc gat tac ttt gtc aac gga tcg       912
Val Phe Tyr Ala Phe Gln Asn Ile Phe Asp Tyr Phe Val Asn Gly Ser
    290                 295                 300 gcc acg ttc cag gcg gag gtg gtg cag aag gcg ctg aac cag gac gga       960
Ala Thr Phe Gln Ala Glu Val Val Gln Lys Ala Leu Asn Gln Asp Gly
305                 310                 315                 320 tac atg ggc tac cat ggg ttc ccg cag atg ccg gtg ctc gcg tac aag      1008
Tyr Met Gly Tyr His Gly Phe Pro Gln Met Pro Val Leu Ala Tyr Lys
                325                 330                 335 gct att cac gat gag atc agt ccc atc cag gat acg gat cgc gtg atc      1056
Ala Ile His Asp Glu Ile Ser Pro Ile Gln Asp Thr Asp Arg Val Ile
            340                 345                 350 aag cgc tac tgt ggt ctg gga ttg aac atc ttg tat gag cgg aac acc      1104
Lys Arg Tyr Cys Gly Leu Gly Leu Asn Ile Leu Tyr Glu Arg Asn Thr
        355                 360                 365 atc ggt ggc cac tcg gca gag cag gtg aat ggc aac gcc agg gcg tgg      1152
Ile Gly Gly His Ser Ala Glu Gln Val Asn Gly Asn Ala Arg Ala Trp
    370                 375                 380 aac tgg ttg acg agc att ttc gac gga acg tat gcg cag cag tac aag      1200
Asn Trp Leu Thr Ser Ile Phe Asp Gly Thr Tyr Ala Gln Gln Tyr Lys
385                 390                 395                 400 acc gag ggg tgc acg atc cgc aat gtc act ctg aac acg act tcc tcc      1248
Thr Glu Gly Cys Thr Ile Arg Asn Val Thr Leu Asn Thr Thr Ser Ser
                405                 410                 415 gtt tat tag                                                          1257
Val Tyr <210> SEQ ID NO 18
<211> LENGTH: 418
<212> TYPE: PRT
<213> ORGANISM: Aspergillus niger

<400> SEQUENCE: 18

Met Tyr Ile Pro Ser Val Leu Leu Leu Ala Ala Ser Leu Phe His Gly
1               5                   10                  15
```

-continued

```
Ala Thr Ala Leu Pro Thr Pro Gly Ser Thr Pro Ile Pro Pro Ser Gln
         20                  25                  30

Asp Pro Trp Tyr Ser Ala Pro Glu Gly Phe Glu Glu Ala Asp Pro Gly
         35                  40                  45

Ala Ile Leu Arg Val Arg Pro Ala Pro Gly Asn Leu Thr Val Val Val
 50                  55                  60

Gly Asn Ala Ser Ala Ala Tyr Asn Ile Leu Tyr Arg Thr Thr Asp Ser
 65                  70                  75                  80

Gln Tyr Lys Pro Ser Trp Ala Val Thr Thr Leu Leu Val Pro Pro Val
             85                  90                  95

Ala Ala Ser Ala Ala Val Asn Gln Ser Val Leu Leu Ser His Gln Ile
             100                 105                 110

Ala Tyr Asp Ser Phe Asp Val Asn Ala Ser Pro Ser Tyr Ala Met Tyr
             115                 120                 125

Thr Ser Pro Pro Ser Asp Ile Ile Leu Ala Leu Gln Arg Gly Trp Phe
         130                 135                 140

Val Asn Val Pro Asp Tyr Glu Gly Pro Asn Ala Ser Phe Thr Ala Gly
145                 150                 155                 160

Val Gln Ser Gly His Ala Thr Leu Asp Ser Val Arg Ser Val Leu Ala
             165                 170                 175

Ser Gly Phe Gly Leu Asn Glu Asp Ala Gln Tyr Ala Leu Trp Gly Tyr
             180                 185                 190

Ser Gly Gly Ala Leu Ala Ser Glu Trp Ala Ala Glu Leu Gln Met Gln
             195                 200                 205

Tyr Ala Pro Glu Leu Asn Ile Ala Gly Leu Ala Val Gly Gly Leu Thr
         210                 215                 220

Pro Asn Val Thr Ser Val Met Asp Thr Val Thr Ser Thr Ile Ser Ala
225                 230                 235                 240

Gly Leu Ile Pro Ala Ala Ala Leu Gly Leu Ser Ser Gln His Pro Glu
             245                 250                 255

Thr Tyr Glu Phe Ile Leu Ser Gln Leu Lys Thr Thr Gly Pro Tyr Asn
             260                 265                 270

Arg Thr Gly Phe Leu Ala Ala Lys Asp Leu Thr Leu Ser Glu Ala Glu
         275                 280                 285

Val Phe Tyr Ala Phe Gln Asn Ile Phe Asp Tyr Phe Val Asn Gly Ser
290                 295                 300

Ala Thr Phe Gln Ala Glu Val Val Gln Lys Ala Leu Asn Gln Asp Gly
305                 310                 315                 320

Tyr Met Gly Tyr His Gly Phe Pro Gln Met Pro Val Leu Ala Tyr Lys
             325                 330                 335

Ala Ile His Asp Glu Ile Ser Pro Ile Gln Asp Thr Asp Arg Val Ile
             340                 345                 350

Lys Arg Tyr Cys Gly Leu Gly Leu Asn Ile Leu Tyr Glu Arg Asn Thr
         355                 360                 365

Ile Gly Gly His Ser Ala Glu Gln Val Asn Gly Asn Ala Arg Ala Trp
         370                 375                 380

Asn Trp Leu Thr Ser Ile Phe Asp Gly Thr Tyr Ala Gln Gln Tyr Lys
385                 390                 395                 400

Thr Glu Gly Cys Thr Ile Arg Asn Val Thr Leu Asn Thr Thr Ser Ser
             405                 410                 415

Val Tyr
```

<210> SEQ ID NO 19
<211> LENGTH: 2809

<212> TYPE: DNA
<213> ORGANISM: Aspergillus niger

<400> SEQUENCE: 19

```
agtaatgtat catttgaaag atcagtaaat gaaatctgct gcacaatgca cgctttgaga      60
acgacgatgc gaatcgtaga atgcccaagt cagtctgcgt ggtcagacga gacccataca     120
ttgcatatgt acaatctagt agtataatat ggtgtaaatc cccataacct gatactcata     180
cacactatca gggcttgggt acatgagcga agtagtccca acaatcaaac aatcatccaa     240
actccaagcc aaatgccagc gaaaacaaca aaagcacaac atgatgttac agtgcactag     300
ggaaaccaat ctgtgtcacc atcactcagg acaccagata taacgaaccc ccctcacaga     360
ccacgagtct tctccggatc catctgcacc tcatcaccgc taatttcctt gaccgtctca     420
aacgccggct tgcccgcata tagctgctgg gacgagctgg agccgccgcc ttccgtcgtc     480
gataccgaga tgggctggtt ccgcggaac cgcttgcgca tatcgatcag gccgcgtcta     540
tagaaggaca aacagttagt aaccctgatg acttggcggt gattgcgttt tacaagaagg     600
tagcggctct ttactcactt gcactcgctg aatcccttcc gcaattgctg gcatcgcatg     660
ggaagctcgt cgacgtacgg ctcactcaga cattcgcggg gcgagcgccg ttgcaccatg     720
atgcagtctg attcttggag acattgggcc agagcatttc ctgttcatcc aggtgagatt     780
gattagagag tgtggagctg aagctgaagt tgggacaat gaggtggtga tctccgttcg     840
gggatacgtc gagtatccaa gccgcaattt aagagtatgg taaaggatat aagggtcaaa     900
cgtactgatc tcttggcagg aactcggcat tttggcgaac aacaatggcc gaattgctca     960
gccaactgac aagcaggaac aataccggtc tgcggcggcg gacatctgga gataaatttgt   1020
ctgatcggaa aacaaactca accaacgggc cttgccccgg attaggtaag ccatcacatg    1080
aagaaggccc ccatgacgtc tgggggaat cctgacttgc tgcttgttcc gcttgattta     1140
tcctcttccc ctagtcatgc ggtcttgggt cttgaagca ttgcttcggc gcattatggt      1200
tcactactac tactgcaggt gataagtatt ttagttggtt gatttgcaaa ttgtccatcc    1260
cttttcgata ataggaggtt tggtcttaat cgtcatggcg cgcgttccgg tcattggacg    1320
gctgttttgg ttcgagtatt tggccctttt tgggtcgctg attttggtat tgctggaatg   1380
ggttatacat attatcacat tctgtctgcg taagtagtgt gttcattctc tggaattgtg    1440
gtctatgtcg aggggcaaga gctaactgac gcagctgaac ctgttattaa gttctgttac    1500
gatcgatcca agactatctt caacgccttc attcctcccg atgacccggc taagcgcggt    1560
aaagaagaga aaattgctgc gtcggttgct ctggcgtcgg acttcacgga tatatgcgcg    1620
ctgttcggat atgaggcgga ggaacatatc gtccagacag gggatggcta tctgcttggt    1680
ctgcaccgac tgccctatcg gaaaggagag gaggggagga agatcaacca gggcgaaggg    1740
agcatcaaga agaaggtcgt ctatctccac catggtctca tgatgtgcag tgaagtctgg    1800
atctgtctgt cagaggagca gcgatgcctt ccgtttcaat tagtcgaaag gggctatgac    1860
gtgtggttgg ggaacaatag aggaaacaag tactcgaaga agtccgtcaa gcattcgccc    1920
ctgtcgaacg agttctggga cttttcgatc gatcagttct cgttccatga tatcccagac    1980
agcatcaagt atatcctgga agtgacaggg cagccctccc tgtcatacgt ggggttctcg    2040
cagggaacag cgcaggcatt tgcgacgctg tccattcatc ctttgttgaa tcagaagatc    2100
gatgtctttg tggctctcgc gccggcaatg gctccgacag gtcttccaaa tcatctcgtg    2160
gactcgctca tgaaggcttc gccgaacttc ctgtttctgc tgtttggcag acgcagcatc    2220
cttagctcaa cgacgatgtg gcagacaatt ctctacccgc ctatctttgt ttggatcatc    2280
```

```
gacacgtcac ttcgcggcct gttcaattgg aggtgcaaga acatcagccg ctggcagaag    2340
ctggcagggt acctgcatct gttttccttc actagcacca agtcggtcgt ccattggttc    2400
cagattattc ggcaccggaa tttccagttc tacgatgacg aaatccatgc cccgctcagt    2460
attgtggcca gtgagcgatt ttacaagccg gtcaagtacc cgactaagaa cattaagacg    2520
cccattgtcc tgttgtatgg cggtagcgat agtctcgttg atatcaacgt gatgttgtcc    2580
gagctccctc gcgggaccgt ggcgaaggaa atcccgcagt atgagcattt agatttcttg    2640
tgggcgcgtg atgtggacca attggtattc aaccatgtct tcgaagcgct ggagcggtac    2700
agctcggaga atcagaaagg gacattgatg gagaaggtta atggtgccgc gggcacatat    2760
gtaccgacat aaagtacgag gtcctgcacc aatgaagaca cgcataatc                2809
```

```
<210> SEQ ID NO 20
<211> LENGTH: 1413
<212> TYPE: DNA
<213> ORGANISM: Aspergillus niger
<220> FEATURE:
<221> NAME/KEY: CDS
<222> LOCATION: (1)..(1413)

<400> SEQUENCE: 20 atg gcg cgc gtt ccg gtc att gga cgg ctg ttt tgg ttc gag tat ttg        48
Met Ala Arg Val Pro Val Ile Gly Arg Leu Phe Trp Phe Glu Tyr Leu
1               5                   10                  15 gcc ctt ttt ggg tcg ctg att ttg gta ttg ctg gaa tgg gtt ata cat        96
Ala Leu Phe Gly Ser Leu Ile Leu Val Leu Leu Glu Trp Val Ile His
                20                  25                  30 att atc aca ttc tgt ctg cct gaa cct gtt att aag ttc tgt tac gat       144
Ile Ile Thr Phe Cys Leu Pro Glu Pro Val Ile Lys Phe Cys Tyr Asp
            35                  40                  45 cga tcc aag act atc ttc aac gcc ttc att cct ccc gat gac ccg gct       192
Arg Ser Lys Thr Ile Phe Asn Ala Phe Ile Pro Pro Asp Asp Pro Ala
50                  55                  60 aag cgc ggt aaa gaa gag aaa att gct gcg tcg gtt gct ctg gcg tcg       240
Lys Arg Gly Lys Glu Glu Lys Ile Ala Ala Ser Val Ala Leu Ala Ser
65                  70                  75                  80 gac ttc acg gat ata tgc gcg ctg ttc gga tat gag gcg gag gaa cat       288
Asp Phe Thr Asp Ile Cys Ala Leu Phe Gly Tyr Glu Ala Glu Glu His
                85                  90                  95 atc gtc cag aca ggg gat ggc tat ctg ctt ggt ctg cac cga ctg ccc       336
Ile Val Gln Thr Gly Asp Gly Tyr Leu Leu Gly Leu His Arg Leu Pro
            100                 105                 110 tat cgg aaa gga gag gag ggg agg aag atc aac cag ggc gaa ggg agc       384
Tyr Arg Lys Gly Glu Glu Gly Arg Lys Ile Asn Gln Gly Glu Gly Ser
        115                 120                 125 atc aag aag aag gtc gtc tat ctc cac cat ggt ctc atg atg tgc agt       432
Ile Lys Lys Lys Val Val Tyr Leu His His Gly Leu Met Met Cys Ser
130                 135                 140 gaa gtc tgg atc tgt ctg tca gag gag cag cga tgc ctt ccg ttt caa       480
Glu Val Trp Ile Cys Leu Ser Glu Glu Gln Arg Cys Leu Pro Phe Gln
145                 150                 155                 160 tta gtc gaa agg ggc tat gac gtg tgg ttg ggg aac aat aga gga aac       528
Leu Val Glu Arg Gly Tyr Asp Val Trp Leu Gly Asn Asn Arg Gly Asn
                165                 170                 175 aag tac tcg aag aag tcc gtc aag cat tcg ccc ctg tcg aac gag ttc       576
Lys Tyr Ser Lys Lys Ser Val Lys His Ser Pro Leu Ser Asn Glu Phe
            180                 185                 190 tgg gac ttt tcg atc gat cag ttc tcg ttc cat gat atc cca gac agc       624
Trp Asp Phe Ser Ile Asp Gln Phe Ser Phe His Asp Ile Pro Asp Ser
```

-continued

```
                195                 200                 205
atc aag tat atc ctg gaa gtg aca ggg cag ccc tcc ctg tca tac gtg      672
Ile Lys Tyr Ile Leu Glu Val Thr Gly Gln Pro Ser Leu Ser Tyr Val
210                 215                 220 ggg ttc tcg cag gga aca gcg cag gca ttt gcg acg ctg tcc att cat      720
Gly Phe Ser Gln Gly Thr Ala Gln Ala Phe Ala Thr Leu Ser Ile His
225                 230                 235                 240 cct ttg ttg aat cag aag atc gat gtc ttt gtg gct ctc gcg ccg gca      768
Pro Leu Leu Asn Gln Lys Ile Asp Val Phe Val Ala Leu Ala Pro Ala
            245                 250                 255 atg gct ccg aca ggt ctt cca aat cat ctc gtg gac tcg ctc atg aag      816
Met Ala Pro Thr Gly Leu Pro Asn His Leu Val Asp Ser Leu Met Lys
        260                 265                 270 gct tcg ccg aac ttc ctg ttt ctg ctg ttt ggc aga cgc agc atc ctt      864
Ala Ser Pro Asn Phe Leu Phe Leu Leu Phe Gly Arg Arg Ser Ile Leu
    275                 280                 285 agc tca acg acg atg tgg cag aca att ctc tac ccg cct atc ttt gtt      912
Ser Ser Thr Thr Met Trp Gln Thr Ile Leu Tyr Pro Pro Ile Phe Val
290                 295                 300 tgg atc atc gac acg tca ctt cgc ggc ctg ttc aat tgg agg tgc aag      960
Trp Ile Ile Asp Thr Ser Leu Arg Gly Leu Phe Asn Trp Arg Cys Lys
305                 310                 315                 320 aac atc agc cgc tgg cag aag ctg gca ggg tac ctg cat ctg ttt tcc     1008
Asn Ile Ser Arg Trp Gln Lys Leu Ala Gly Tyr Leu His Leu Phe Ser
            325                 330                 335 ttc act agc acc aag tcg gtc gtc cat tgg ttc cag att att cgg cac     1056
Phe Thr Ser Thr Lys Ser Val Val His Trp Phe Gln Ile Ile Arg His
        340                 345                 350 cgg aat ttc cag ttc tac gat gac gaa atc cat gcc ccg ctc agt att     1104
Arg Asn Phe Gln Phe Tyr Asp Asp Glu Ile His Ala Pro Leu Ser Ile
    355                 360                 365 gtg gcc agt gag cga ttt tac aag ccg gtc aag tac ccg act aag aac     1152
Val Ala Ser Glu Arg Phe Tyr Lys Pro Val Lys Tyr Pro Thr Lys Asn
370                 375                 380 att aag acg ccc att gtc ctg ttg tat ggc ggt agc gat agt ctc gtt     1200
Ile Lys Thr Pro Ile Val Leu Leu Tyr Gly Gly Ser Asp Ser Leu Val
385                 390                 395                 400 gat atc aac gtg atg ttg tcc gag ctc cct cgc ggg acc gtg gcg aag     1248
Asp Ile Asn Val Met Leu Ser Glu Leu Pro Arg Gly Thr Val Ala Lys
            405                 410                 415 gaa atc ccg cag tat gag cat tta gat ttc ttg tgg gcg cgt gat gtg     1296
Glu Ile Pro Gln Tyr Glu His Leu Asp Phe Leu Trp Ala Arg Asp Val
        420                 425                 430 gac caa ttg gta ttc aac cat gtc ttc gaa gcg ctg gag cgg tac agc     1344
Asp Gln Leu Val Phe Asn His Val Phe Glu Ala Leu Glu Arg Tyr Ser
    435                 440                 445 tcg gag aat cag aaa ggg aca ttg atg gag aag gtt aat ggt gcc gcg     1392
Ser Glu Asn Gln Lys Gly Thr Leu Met Glu Lys Val Asn Gly Ala Ala
450                 455                 460 ggc aca tat gta ccg aca taa                                         1413
Gly Thr Tyr Val Pro Thr
465                 470
```

<210> SEQ ID NO 21
<211> LENGTH: 470
<212> TYPE: PRT
<213> ORGANISM: Aspergillus niger

<400> SEQUENCE: 21

```
Met Ala Arg Val Pro Val Ile Gly Arg Leu Phe Trp Phe Glu Tyr Leu
1               5                   10                  15
```

```
Ala Leu Phe Gly Ser Leu Ile Leu Val Leu Glu Trp Val Ile His
             20                  25                  30
Ile Ile Thr Phe Cys Leu Pro Glu Pro Val Ile Lys Phe Cys Tyr Asp
             35                  40                  45
Arg Ser Lys Thr Ile Phe Asn Ala Phe Ile Pro Pro Asp Asp Pro Ala
 50                  55                  60
Lys Arg Gly Lys Glu Glu Lys Ile Ala Ala Ser Val Ala Leu Ala Ser
 65                  70                  75                  80
Asp Phe Thr Asp Ile Cys Ala Leu Phe Gly Tyr Glu Ala Glu His
             85                  90                  95
Ile Val Gln Thr Gly Asp Gly Tyr Leu Leu Gly Leu His Arg Leu Pro
             100                 105                 110
Tyr Arg Lys Gly Glu Glu Gly Arg Lys Ile Asn Gln Gly Glu Gly Ser
             115                 120                 125
Ile Lys Lys Lys Val Val Tyr Leu His His Gly Leu Met Met Cys Ser
 130                 135                 140
Glu Val Trp Ile Cys Leu Ser Glu Glu Gln Arg Cys Leu Pro Phe Gln
 145                 150                 155                 160
Leu Val Glu Arg Gly Tyr Asp Val Trp Leu Gly Asn Asn Arg Gly Asn
             165                 170                 175
Lys Tyr Ser Lys Lys Ser Val Lys His Ser Pro Leu Ser Asn Glu Phe
             180                 185                 190
Trp Asp Phe Ser Ile Asp Gln Phe Ser Phe His Asp Ile Pro Asp Ser
             195                 200                 205
Ile Lys Tyr Ile Leu Glu Val Thr Gly Gln Pro Ser Leu Ser Tyr Val
             210                 215                 220
Gly Phe Ser Gln Gly Thr Ala Gln Ala Phe Ala Thr Leu Ser Ile His
 225                 230                 235                 240
Pro Leu Leu Asn Gln Lys Ile Asp Val Phe Val Ala Leu Ala Pro Ala
             245                 250                 255
Met Ala Pro Thr Gly Leu Pro Asn His Leu Val Asp Ser Leu Met Lys
             260                 265                 270
Ala Ser Pro Asn Phe Leu Phe Leu Leu Phe Gly Arg Arg Ser Ile Leu
             275                 280                 285
Ser Ser Thr Thr Met Trp Gln Thr Ile Leu Tyr Pro Pro Ile Phe Val
             290                 295                 300
Trp Ile Ile Asp Thr Ser Leu Arg Gly Leu Phe Asn Trp Arg Cys Lys
 305                 310                 315                 320
Asn Ile Ser Arg Trp Gln Lys Leu Ala Gly Tyr Leu His Leu Phe Ser
             325                 330                 335
Phe Thr Ser Thr Lys Ser Val Val His Trp Phe Gln Ile Ile Arg His
             340                 345                 350
Arg Asn Phe Gln Phe Tyr Asp Asp Glu Ile His Ala Pro Leu Ser Ile
             355                 360                 365
Val Ala Ser Glu Arg Phe Tyr Lys Pro Val Lys Tyr Pro Thr Lys Asn
 370                 375                 380
Ile Lys Thr Pro Ile Val Leu Leu Tyr Gly Gly Ser Asp Ser Leu Val
 385                 390                 395                 400
Asp Ile Asn Val Met Leu Ser Glu Leu Pro Arg Gly Thr Val Ala Lys
             405                 410                 415
Glu Ile Pro Gln Tyr Glu His Leu Asp Phe Leu Trp Ala Arg Asp Val
             420                 425                 430
Asp Gln Leu Val Phe Asn His Val Phe Glu Ala Leu Glu Arg Tyr Ser
```

```
                    435                 440                 445
Ser Glu Asn Gln Lys Gly Thr Leu Met Glu Lys Val Asn Gly Ala Ala
    450                 455                 460

Gly Thr Tyr Val Pro Thr
465                 470

<210> SEQ ID NO 22
<211> LENGTH: 3328
<212> TYPE: DNA
<213> ORGANISM: Aspergillus niger

<400> SEQUENCE: 22
gatttatgaa gacaggggag ctctcagtag atgatcttcg cacaattgca cttcctgggg      60
agcctgttta gtctctagtg aattattgat agacaggtca tctgcctcga ggggttcta     120 ctaacaacgt gatatctatg ttgctccttt actttagaag aaaggttctg cttggtagct     180
ggaacccagt atatagttga tgtgagtata tgaagattcc aatgctttgg aatattccgc     240
cgtggctgaa tgatgggact ctcactgcca agccaaggga ttcctcccga aattttgca     300 catatgttgt tgatgcctta tccctctggc attcactcgt tgctgcctcg ggtgggaccc     360
gacagtcctc aaacgatgaa atcttattgg ctctgctagt tgagctcggt ttcaccattt     420
ctattggcgc tttctcactc tactccatat tacagcttcc gctttgcaat gcggggctgt     480
gctgcgactt tgaattgctc gcatagcaag agacactgac cagcaatcca gctcttctgc     540
ccacatatgt tgcctttgcc ttagtatctc ataattatg tgtccagtga acagtttgt     600 ttgtactgta gcttgagttg ggaatcgtgt cctgtgacca tggaaatata tattctggat     660
ctcagaacat ctctaccgtt tgtaattttt gatatacttc caggatggg acaatgggga     720 cgatgagtat tgggatgcca tatcacttga aagcctctta gacagactgc acctatttt     780 attatgctaa attctttacg agacactttc ttcaagtttc tggccctttg tgaggcagag     840
tgaaacacga gcgttcaaac ttgtgttgta gatgtttatg atatttatct cagacagtct     900
ttccacatcc tgtaatcccc aacagaaaaa gatacacagt atatcactag aagctcctaa     960
tagttatcat gctgcaccct aacagcaatg cagtcaccct gctgcgtcag cgaccccgat    1020
tccggagaag tatccgagat agcgataagg atgcggagat aagattggca agtggagatg    1080
agaaagatat cctcggcctc agaagtaggc ccgatgataa ataactagtg aacaagtccc    1140
ccgcccttct ccgagcaaac tacacttcaa catgctgaat gcacgctcca ttgctctggc    1200
ctcgttgcca gttcttctcc tactattcgc ccagcaactt gcctctcacc caaccgagca    1260
gattcaagcc attctggctc cgtgggtccc ggccgcacta caagatgtcg tgctctataa    1320
tcgacctcgc gtcataatcc cccagggcac tgtcgtcggc acgaccttga cagacacgct    1380
caagtccccg gtagatgctt ccgaggaat tccatacgca ttgcctccaa ttggggatag    1440
acggtttcgc cgtgcggagg ctgtccatgc gacggacgag attatcgatg ctagtgaatt    1500
cggcccaagg tatgcttctt atacgacatt cagatcatat ctgacctttc aggtgccctg    1560
gaaagcagct cttgaatcca atgacatag tggtgatga agactgtctc acagtcaatg    1620
tcttccggcc tcatggcgct cagggaaaac tccctgtcgc tgtatacgtg cacggcggag    1680
cctacaatcg cggcactggt aggtgtatca ccctcagtcc tctatatacc cacagctaaa    1740
tatccagcct ccggacacaa cacggcctcg atggtcggct ggtcggacga gcccttcgtt    1800
gcagtcagct tcaactaccg gtacgtcctc aaacctgtcc tccgaatcaa ctcaactaac    1860
aacccatcag catcggcgcc ctcggcttcc tcccatccac cctaaccgcc aaagaaggaa    1920
```

```
tcctcaacct aggcctccat gaccagatcc tcctgctgca atgggtccaa gaaaacatcg    1980
cacatttcaa cggcgaccca acccaagtca ctctaatcgg cctctccgcc ggcgcgcact    2040
ccgtatgccc ccttctaaga tacaaataga actcagtccc ctaccccaa actaacgcca     2100 cacagatagc ccaccacatc atgaactaca acccaccaaa cacccccctc tttcaccgcg    2160
ccatcatcga atccggcgcc gccacctccc gcgccgtcca ccctacaac gcctccctcc     2220 acgaatccca attcacagac ttcctcactg aaacgggctg cactaacctc cccgacactg    2280
ccattttgcc ctgtctccgc gccctcccat cctcagccat taccaccgcc tccatctccg    2340
tcttcgacaa atacaacccc tccatccgct gggccttcca acccgtcatc gaccacgaga    2400
tcatccaccg ccggcccatc gacgcctggc gctcaggaaa gtggaatagg atgcccatcc    2460
taacgggctt caactcgaac gaggggacat actacgtccc tcgcaacctc tctctctccg    2520
aggatttcac ttcgttcttc cgaaccctcc tccccgcgta ccccgagagc gacatccaga    2580
ccatcgatga gatctacccc gatccgaatg tatatgctac ggcgtcgcca tacctcgaga    2640
caaggccgat cccgagtcta ggaaggcagt ttaagcggct ggaggcggcg tatgggcatt    2700
atgcgtatgc gtgtccagta cggcagacgg cggggtttgt tgctaatgat gatggttgtg    2760
gtgagccggt gttttttgtat cgctgggcgt tgaataagac tgttattgga ggcgcgaacc    2820
atggtgatca gatggagtat gagacgttta atcctgcggt tagggatatt tcggaggctc    2880
agagggaggt tgcggggttg tttcatgcgt atgtgacttc gtttgtggtg catggggatc    2940
cgaatgttct gggggggtagg tatgagggga gggaggtttg ggagaggtat agtggggagg    3000
gaggggaggt gatggtgttt ggggagggga atgatgaacg tgctgggggg gatggagttg    3060
gggttgcggc gaggttgaag agggatgagt gggggggtgaa ggagtgtgga ttttggtctg    3120
ggaggagtgg gatttccgag tgatggtttg tttatatata gtctagtgga aggggatgta    3180
tatactgtag tcactatctg tagaaacttta cttggtgtgt agatagtaaa tactacaact    3240
gctgaagacc ttgggataga acgacatgct gtttaatcct caaccctgac tagatatatt    3300
gtgcattact tgcatccacg cctaacat                                       3328
```

<210> SEQ ID NO 23
<211> LENGTH: 1779
<212> TYPE: DNA
<213> ORGANISM: Aspergillus niger
<220> FEATURE:
<221> NAME/KEY: CDS
<222> LOCATION: (1)..(1779)

<400> SEQUENCE: 23

```
atg ctg aat gca cgc tcc att gct ctg gcc tcg ttg cca gtt ctt ctc    48
Met Leu Asn Ala Arg Ser Ile Ala Leu Ala Ser Leu Pro Val Leu Leu
1               5                   10                  15 cta cta ttc gcc cag caa ctt gcc tct cac cca acc gag cag att caa    96
Leu Leu Phe Ala Gln Gln Leu Ala Ser His Pro Thr Glu Gln Ile Gln
            20                  25                  30 gcc att ctg gct ccg tgg gtc ccg gcc gca cta caa gat gtc gtg ctc   144
Ala Ile Leu Ala Pro Trp Val Pro Ala Ala Leu Gln Asp Val Val Leu
        35                  40                  45 tat aat cga cct cgc gtc ata atc ccc cag ggc act gtc gtc ggc acg   192
Tyr Asn Arg Pro Arg Val Ile Ile Pro Gln Gly Thr Val Val Gly Thr
    50                  55                  60 acc ttg aca gac acg ctc aag tcc ccg gta gat gct ttc cga gga att   240
Thr Leu Thr Asp Thr Leu Lys Ser Pro Val Asp Ala Phe Arg Gly Ile
65                  70                  75                  80 cca tac gca ttg cct cca att ggg gat aga cgg ttt cgc cgt gcg gag   288
```

-continued

```
                Pro Tyr Ala Leu Pro Pro Ile Gly Asp Arg Arg Phe Arg Arg Ala Glu
                                85                  90                  95 gct gtc cat gcg acg gac gag att atc gat gct agt gaa ttc ggc cca        336
Ala Val His Ala Thr Asp Glu Ile Ile Asp Ala Ser Glu Phe Gly Pro
                100                 105                 110 agg tgc cct gga aag cag ctc ttg aat cca aat gac ata ggt ggt gat        384
Arg Cys Pro Gly Lys Gln Leu Leu Asn Pro Asn Asp Ile Gly Gly Asp
            115                 120                 125 gaa gac tgt ctc aca gtc aat gtc ttc cgg cct cat ggc gct cag gga        432
Glu Asp Cys Leu Thr Val Asn Val Phe Arg Pro His Gly Ala Gln Gly
        130                 135                 140 aaa ctc cct gtc gct gta tac gtg cac ggc gga gcc tac aat cgc ggc        480
Lys Leu Pro Val Ala Val Tyr Val His Gly Gly Ala Tyr Asn Arg Gly
145                 150                 155                 160 act gct aaa tat cca gcc tcc gga cac aac acg gcc tcg atg gtc ggc        528
Thr Ala Lys Tyr Pro Ala Ser Gly His Asn Thr Ala Ser Met Val Gly
                165                 170                 175 tgg tcg gac gag ccc ttc gtt gca gtc agc ttc aac tac cgc atc ggc        576
Trp Ser Asp Glu Pro Phe Val Ala Val Ser Phe Asn Tyr Arg Ile Gly
            180                 185                 190 gcc ctc ggc ttc ctc cca tcc acc cta acc gcc aaa gaa gga atc ctc        624
Ala Leu Gly Phe Leu Pro Ser Thr Leu Thr Ala Lys Glu Gly Ile Leu
        195                 200                 205 aac cta ggc ctc cat gac cag atc ctc ctg ctg caa tgg gtc caa gaa        672
Asn Leu Gly Leu His Asp Gln Ile Leu Leu Leu Gln Trp Val Gln Glu
    210                 215                 220 aac atc gca cat ttc aac ggc gac cca acc caa gtc act cta atc ggc        720
Asn Ile Ala His Phe Asn Gly Asp Pro Thr Gln Val Thr Leu Ile Gly
225                 230                 235                 240 ctc tcc gcc ggc gcg cac tcc ata gcc cac cac atc atg aac tac aac        768
Leu Ser Ala Gly Ala His Ser Ile Ala His His Ile Met Asn Tyr Asn
                245                 250                 255 cca cca aac acc ccc ctc ttt cac cgc gcc atc atc gaa tcc ggc gcc        816
Pro Pro Asn Thr Pro Leu Phe His Arg Ala Ile Ile Glu Ser Gly Ala
            260                 265                 270 gcc acc tcc cgc gcc gtc cac ccc tac aac gcc tcc ctc cac gaa tcc        864
Ala Thr Ser Arg Ala Val His Pro Tyr Asn Ala Ser Leu His Glu Ser
        275                 280                 285 caa ttc aca gac ttc ctc act gaa acg ggc tgc act aac ctc ccc gac        912
Gln Phe Thr Asp Phe Leu Thr Glu Thr Gly Cys Thr Asn Leu Pro Asp
    290                 295                 300 act gcc att ttg ccc tgt ctc cgc gcc ctc cca tcc tca gcc att acc        960
Thr Ala Ile Leu Pro Cys Leu Arg Ala Leu Pro Ser Ser Ala Ile Thr
305                 310                 315                 320 acc gcc tcc atc tcc gtc ttc gac aaa tac aac ccc tcc atc cgc tgg       1008
Thr Ala Ser Ile Ser Val Phe Asp Lys Tyr Asn Pro Ser Ile Arg Trp
                325                 330                 335 gcc ttc caa ccc gtc atc gac cac gag atc atc cac cgc cgg ccc atc       1056
Ala Phe Gln Pro Val Ile Asp His Glu Ile Ile His Arg Arg Pro Ile
            340                 345                 350 gac gcc tgg cgc tca gga aag tgg aat agg atg ccc atc cta acg ggc       1104
Asp Ala Trp Arg Ser Gly Lys Trp Asn Arg Met Pro Ile Leu Thr Gly
        355                 360                 365 ttc aac tcg aac gag ggg aca tac tac gtc cct cgc aac ctc tct ctc       1152
Phe Asn Ser Asn Glu Gly Thr Tyr Tyr Val Pro Arg Asn Leu Ser Leu
    370                 375                 380 tcc gag gat ttc act tcg ttc ttc cga acc ctc ctc ccc gcg tac ccc       1200
Ser Glu Asp Phe Thr Ser Phe Phe Arg Thr Leu Leu Pro Ala Tyr Pro
385                 390                 395                 400 gag agc gac atc cag acc atc gat gag atc tac ccc gat ccg aat gta       1248
```

```
Glu Ser Asp Ile Gln Thr Ile Asp Glu Ile Tyr Pro Asp Pro Asn Val
                405                 410                 415 tat gct acg gcg tcg cca tac ctc gag aca agg ccg atc ccg agt cta      1296
Tyr Ala Thr Ala Ser Pro Tyr Leu Glu Thr Arg Pro Ile Pro Ser Leu
            420                 425                 430 gga agg cag ttt aag cgg ctg gag gcg gcg tat ggg cat tat gcg tat      1344
Gly Arg Gln Phe Lys Arg Leu Glu Ala Ala Tyr Gly His Tyr Ala Tyr
        435                 440                 445 gcg tgt cca gta cgg cag acg gcg ggg ttt gtt gct aat gat gat ggt      1392
Ala Cys Pro Val Arg Gln Thr Ala Gly Phe Val Ala Asn Asp Asp Gly
    450                 455                 460 tgt ggt gag ccg gtg ttt ttg tat cgc tgg gcg ttg aat aag act gtt      1440
Cys Gly Glu Pro Val Phe Leu Tyr Arg Trp Ala Leu Asn Lys Thr Val
465                 470                 475                 480 att gga ggc gcg aac cat ggt gat cag atg gag tat gag acg ttt aat      1488
Ile Gly Gly Ala Asn His Gly Asp Gln Met Glu Tyr Glu Thr Phe Asn
                485                 490                 495 cct gcg gtt agg gat att tcg gag gct cag agg gag gtt gcg ggg ttg      1536
Pro Ala Val Arg Asp Ile Ser Glu Ala Gln Arg Glu Val Ala Gly Leu
            500                 505                 510 ttt cat gcg tat gtg act tcg ttt gtg gtg cat ggg gat ccg aat gtt      1584
Phe His Ala Tyr Val Thr Ser Phe Val Val His Gly Asp Pro Asn Val
        515                 520                 525 ctg ggg ggt agg tat gag ggg agg gag gtt tgg gag agg tat agt ggg      1632
Leu Gly Gly Arg Tyr Glu Gly Arg Glu Val Trp Glu Arg Tyr Ser Gly
    530                 535                 540 gag gga ggg gag gtg atg gtg ttt ggg gag ggg aat gat gaa cgt gct      1680
Glu Gly Gly Glu Val Met Val Phe Gly Glu Gly Asn Asp Glu Arg Ala
545                 550                 555                 560 ggg ggg gat gga gtt ggg gtt gcg gcg agg ttg aag agg gat gag tgg      1728
Gly Gly Asp Gly Val Gly Val Ala Ala Arg Leu Lys Arg Asp Glu Trp
                565                 570                 575 ggg gtg aag gag tgt gga ttt tgg tct ggg agg agt ggg att tcc gag      1776
Gly Val Lys Glu Cys Gly Phe Trp Ser Gly Arg Ser Gly Ile Ser Glu
            580                 585                 590 tga                                                                  1779

<210> SEQ ID NO 24
<211> LENGTH: 592
<212> TYPE: PRT
<213> ORGANISM: Aspergillus niger

<400> SEQUENCE: 24

Met Leu Asn Ala Arg Ser Ile Ala Leu Ala Ser Leu Pro Val Leu Leu
1               5                   10                  15

Leu Leu Phe Ala Gln Gln Leu Ala Ser His Pro Thr Glu Gln Ile Gln
            20                  25                  30

Ala Ile Leu Ala Pro Trp Val Pro Ala Ala Leu Gln Asp Val Val Leu
        35                  40                  45

Tyr Asn Arg Pro Arg Val Ile Ile Pro Gln Gly Thr Val Val Gly Thr
    50                  55                  60

Thr Leu Thr Asp Thr Leu Lys Ser Pro Val Asp Ala Phe Arg Gly Ile
65                  70                  75                  80

Pro Tyr Ala Leu Pro Pro Ile Gly Asp Arg Arg Phe Arg Arg Ala Glu
                85                  90                  95

Ala Val His Ala Thr Asp Glu Ile Ile Asp Ala Ser Glu Phe Gly Pro
            100                 105                 110

Arg Cys Pro Gly Lys Gln Leu Leu Asn Pro Asn Asp Ile Gly Gly Asp
        115                 120                 125
```

```
Glu Asp Cys Leu Thr Val Asn Val Phe Arg Pro His Gly Ala Gln Gly
    130                 135                 140
Lys Leu Pro Val Ala Val Tyr Val His Gly Gly Ala Tyr Asn Arg Gly
145                 150                 155                 160
Thr Ala Lys Tyr Pro Ala Ser Gly His Asn Thr Ala Ser Met Val Gly
                165                 170                 175
Trp Ser Asp Glu Pro Phe Val Ala Val Ser Phe Asn Tyr Arg Ile Gly
            180                 185                 190
Ala Leu Gly Phe Leu Pro Ser Thr Leu Thr Ala Lys Glu Gly Ile Leu
        195                 200                 205
Asn Leu Gly Leu His Asp Gln Ile Leu Leu Leu Gln Trp Val Gln Glu
    210                 215                 220
Asn Ile Ala His Phe Asn Gly Asp Pro Thr Gln Val Thr Leu Ile Gly
225                 230                 235                 240
Leu Ser Ala Gly Ala His Ser Ile Ala His His Ile Met Asn Tyr Asn
                245                 250                 255
Pro Pro Asn Thr Pro Leu Phe His Arg Ala Ile Ile Glu Ser Gly Ala
            260                 265                 270
Ala Thr Ser Arg Ala Val His Pro Tyr Asn Ala Ser Leu His Glu Ser
        275                 280                 285
Gln Phe Thr Asp Phe Leu Thr Glu Thr Gly Cys Thr Asn Leu Pro Asp
    290                 295                 300
Thr Ala Ile Leu Pro Cys Leu Arg Ala Leu Pro Ser Ser Ala Ile Thr
305                 310                 315                 320
Thr Ala Ser Ile Ser Val Phe Asp Lys Tyr Asn Pro Ser Ile Arg Trp
                325                 330                 335
Ala Phe Gln Pro Val Ile Asp His Glu Ile Ile His Arg Arg Pro Ile
            340                 345                 350
Asp Ala Trp Arg Ser Gly Lys Trp Asn Arg Met Pro Ile Leu Thr Gly
        355                 360                 365
Phe Asn Ser Asn Glu Gly Thr Tyr Tyr Val Pro Arg Asn Leu Ser Leu
    370                 375                 380
Ser Glu Asp Phe Thr Ser Phe Phe Arg Thr Leu Leu Pro Ala Tyr Pro
385                 390                 395                 400
Glu Ser Asp Ile Gln Thr Ile Asp Glu Ile Tyr Pro Asp Pro Asn Val
                405                 410                 415
Tyr Ala Thr Ala Ser Pro Tyr Leu Glu Thr Arg Pro Ile Pro Ser Leu
            420                 425                 430
Gly Arg Gln Phe Lys Arg Leu Glu Ala Ala Tyr Gly His Tyr Ala Tyr
        435                 440                 445
Ala Cys Pro Val Arg Gln Thr Ala Gly Phe Val Ala Asn Asp Asp Gly
    450                 455                 460
Cys Gly Glu Pro Val Phe Leu Tyr Arg Trp Ala Leu Asn Lys Thr Val
465                 470                 475                 480
Ile Gly Gly Ala Asn His Gly Asp Gln Met Glu Tyr Glu Thr Phe Asn
                485                 490                 495
Pro Ala Val Arg Asp Ile Ser Glu Ala Gln Arg Glu Val Ala Gly Leu
            500                 505                 510
Phe His Ala Tyr Val Thr Ser Phe Val His Gly Asp Pro Asn Val
        515                 520                 525
Leu Gly Gly Arg Tyr Glu Gly Arg Glu Val Trp Glu Arg Tyr Ser Gly
    530                 535                 540
Glu Gly Gly Glu Val Met Val Phe Gly Glu Gly Asn Asp Glu Arg Ala
```

```
                545                 550                 555                 560
Gly Gly Asp Gly Val Gly Val Ala Ala Arg Leu Lys Arg Asp Glu Trp
                565                 570                 575
Gly Val Lys Glu Cys Gly Phe Trp Ser Gly Arg Ser Gly Ile Ser Glu
                580                 585                 590

<210> SEQ ID NO 25
<211> LENGTH: 3932
<212> TYPE: DNA
<213> ORGANISM: Aspergillus niger

<400> SEQUENCE: 25
cagataacgt tttgagtttg gggatcttga ttatctcggc tccaaacaga ctcgcctatc      60
cgagagatca agtacataat gcaactagct attagtcaaa tataacgccg gcagaagtct     120
attttgtcct tttctctttc tttcctcgaa gaaaacccgt ggattaactt gagccggtcg     180
gcctcaaagt cggctcaacc ggcgcgttgc aactttaaa tgcagacaac catcgtttcc      240
ggccgttgtg ggggcgatgt agatcagatc caaattccca aaacatccat ggggtaaatc     300
aagaattgag gttacatcga ccgatagggc tcttaatcca accctcttca cggggaaaac     360
cttctatatg atacatggtt tactcctctg tttctcttcc tccccggagg tgccaaatcc     420
gggcgcatcg tgtctattct tagcaaccag cgaatttgac aaattgatcc aatcccatag     480
aatcagagta actctacaac ccaatcagtc gcctaatacg cacagcaaaa gaagatgcat     540
tcggacagcc aacgcaagaa aagagattaa aaaaaaaaaa aaaaaaaaaa aaaaaaaaaa     600
aaaaggcctc ccctcatcac ctcaccaaag tcgcaatcaa tcagcgacca ctagctacat     660
cgcgactgaa cgatagcatt ccgcatggtg ttaaagttca agacagttgc tatgcttgcc     720
cgaacccttta cacattcttg ccctttccgt agaattccaa gctcatcgga cagagagtag     780
tgtttctgtg aatgtggtgg tttaccaccg ttacctctgc tgtctatcac ttgctcctac     840
ccctgagcac aggcaccata gttacaacac ccccacgggg ccattgtctg ttttcagctt     900
cagcttcgtc gacaatggac tgtcatatcc cctcatctca aaagaatgtc ggaaacactg     960
tatggcatgg cgtgtgggaa ccgatcaatt tgtataatat cttaggccca cctcttcccc    1020
tccgagaggt ttgacatcag ggggtttcag agatagtccg tcgatattta tggcttcctc    1080
tgtcttcttg ccgctacttg cggcctcatt actgcccaca ctcgcttcta cacagaatgc    1140
cgatacaccg acatccgctc ctactgtgca agtccgcaat ggcacatacg agggtctcta    1200
taatcccacg tacaatcagg acttgttcct cggcataccg tatgcgcagc ctccggttgg    1260
tgagctacga ttccgtccac cacaaccgct caacacgacg tggactggca ctcgaaatgc    1320
aacagcctat tacaatgaat gtatcggtta tggtagcgac gactggtatt ggaccgacgt    1380
agtctccgaa gattgtctcg ctctcagtgt gattcgacct cacggcatcg actcaagcgc    1440
gaagctgccc gtcgtcttct ggatgcatgg tggagaattc gcagaaggag gcactcgcga    1500
ctcccgttac aacctctcct acatcgtcca acaatcccag gagatgcaat ctcccatcat    1560
tggcgtgact gtcaactacc gcctttcggg atggggattc tctctatagcc aggaagtcgc    1620
cgacgaaggc tccgccaact taggactccg cgaccaacgg cacgctctgt actggctcca    1680
agagaatatc gcttccttcg gcggcgaccc gtcgcggctc accatctggg gccaaagtgc    1740
cggtgccaac agcgtcggtc tccatttagt ggcatacgac ggccagaatg atggcatctt    1800
ccgtgccggg atcgccgaga gcggctccgt accctccctc gcagcataca tgagcgccga    1860
agatgcacaa ccatactatg atgccgtcgt caacgcaacc aactgcaccg gctcttccaa    1920
```

-continued

```
caccccttact tgtctccgtg aagttcccac cgacgtcctc agctccatct tcaacagctc    1980
cctcgtcgct ggggcaggat atcatcccgt cattgacggc gatttcctca gagcctcggg    2040
gatagttaat ctccagactg gccaattcgc caaaaccccg cttcttatcg gcaccaactt    2100
cgacgaaggg accaagtatg cccctcatgg ctataatacc accgaccaat ttgtctccct    2160
cgtccaagcc aacggaacca attataccag cgctctcacc attgcatccc tgtacccaga    2220
tgacccagcc gttggtattc cgggaacccct tcaaggtcgt cccccaccgt catacggtta    2280
ccagtggaag cgcgtggctg ccttcctcgg cgatctgctc atgcacgcgc ctcgccgcgt    2340
gacaacccag tggctggcac actggaatgt acctgcctac gtgtatcact ggaacgtgat    2400
gacactaggg ccattagatg gagccgcgca tggctatgaa gtccccttca gtttccataa    2460
ttatgatggt ttgggcgatg aacggggaaa cgacagcgtg acctggccac aactatcgac    2520
tatgatgtca cggatgtggg tgagctttat taatcatttg gatccgaatt atagtaatag    2580
tgagtgattt gccccaccta cctctggaca ctgctttagg agcttgaggg taaggaagga    2640
tgctgacacg ctgctctgct agtgacggat atccactggc ctgtctacac aacagaaacc    2700
ccgcaaaata tggtctttga tgtcaatgtg actggactgg cttatgttga accagatacc    2760
tatagagcgg agggaattgc gtatatcact agcattctgc agagtgcctt taatcggtag    2820
ggtagactag aggcttcaat atcaatagat atcacacata caggagagca gcccatgttt    2880
ccctccagat caagagctat tccgttaaaa ggtagtgcat ccccgcaccg ggggaaggc    2940 cggggagtgc ttacctctgt gtgaaactag aattccagca acgatggttt tagaaaggcc    3000
agatctgttg actcattgtt tgatcctccg atgttgcatc cgagaaagct tctgcttggt    3060
cgtgccaagg atgttaacag ctgctgttga ggcaactcta gaaacccct agacctttac    3120 tatctcgctg actagagggt acagtaggtc ctactttgaa ttccttggcg gttgggattt    3180
cgcggaaggt tgtctcaacc ctcaatgctt gtcacgacag acggcttggc aatgagacga    3240
gaccacgggc gattgacatg tgtcaagcag tagctatcgg gaatctgaaa aagcatggct    3300
gtcatggact ttgcaggcaa aggctgtctg ttctagacca tcggctagag cgcggtgagc    3360
atactaggcg agctgaaaag cctagaagcg gttgccggtt atccgctttg tttgtgccct    3420 ttccgttttcc gggcgtaggc aatcacattt aggcaatgcc gtgtgggcct tggagatctc    3480
acctaacctt attgcatttt acctcacggt gatacaacct gagtgactat cagggaaact    3540
gagcctattg atcatcacat attagcacca cacaaagctg ccaaggaaca atagtaatgt    3600
gagcgccaag gagatatctt tgaactttgt ctccagatct tgtactacat acccagccag    3660
acaggggttc gtatcgatgg ctccacagcg ggatatcatg aatcttcatg tcgtcacgac    3720 tcataccctcg agcgatagg ccgggtatta ctccatctgg aaattgtcat gactgtagag    3780
ctcagctgtc cgggatacga gcattatccg tcagtttata aattccaggg ccatcctgct    3840
caatctcaac atgtgggctc ttacgctgtc atcatattag ttagggtcca agagaatcac    3900
agaatcattg gcattgttct tcatcgttcc aa                                   3932
```

<210> SEQ ID NO 26
<211> LENGTH: 1518
<212> TYPE: DNA
<213> ORGANISM: Aspergillus niger
<220> FEATURE:
<221> NAME/KEY: CDS
<222> LOCATION: (1)..(1518)

<400> SEQUENCE: 26

```
atg gct tcc tct gtc ttc ttg ccg cta ctt gcg gcc tca tta ctg ccc        48
```

```
                Met Ala Ser Ser Val Phe Leu Pro Leu Leu Ala Ala Ser Leu Leu Pro
                1               5                   10                  15 aca ctc gct tct aca cag aat gcc gat aca ccg aca tcc gct cct act         96
Thr Leu Ala Ser Thr Gln Asn Ala Asp Thr Pro Thr Ser Ala Pro Thr
            20                  25                  30 gtg caa gtc cgc aat ggc aca tac gag ggt ctc tat aat ccc acg tac         144
Val Gln Val Arg Asn Gly Thr Tyr Glu Gly Leu Tyr Asn Pro Thr Tyr
        35                  40                  45 aat cag gac ttg ttc ctc ggc ata ccg tat gcg cag cct ccg gtt ggt         192
Asn Gln Asp Leu Phe Leu Gly Ile Pro Tyr Ala Gln Pro Pro Val Gly
    50                  55                  60 gag cta cga ttc cgt cca cca caa ccg ctc aac acg acg tgg act ggc         240
Glu Leu Arg Phe Arg Pro Pro Gln Pro Leu Asn Thr Thr Trp Thr Gly
65              70                  75                  80 act cga aat gca aca gcc tat tac aat gaa tgt atc ggt tat ggt agc         288
Thr Arg Asn Ala Thr Ala Tyr Tyr Asn Glu Cys Ile Gly Tyr Gly Ser
                85                  90                  95 gac gac tgg tat tgg acc gac gta gtc tcc gaa gat tgt ctc gct ctc         336
Asp Asp Trp Tyr Trp Thr Asp Val Val Ser Glu Asp Cys Leu Ala Leu
            100                 105                 110 agt gtg att cga cct cac ggc atc gac tca agc gcg aag ctg ccc gtc         384
Ser Val Ile Arg Pro His Gly Ile Asp Ser Ser Ala Lys Leu Pro Val
        115                 120                 125 gtc ttc tgg atg cat ggt gga gaa ttc gca gaa gga ggc act cgc gac         432
Val Phe Trp Met His Gly Gly Glu Phe Ala Glu Gly Gly Thr Arg Asp
    130                 135                 140 tcc cgt tac aac ctc tcc tac atc gtc caa caa tcc cag gag atg caa         480
Ser Arg Tyr Asn Leu Ser Tyr Ile Val Gln Gln Ser Gln Glu Met Gln
145                 150                 155                 160 tct ccc atc att ggc gtg act gtc aac tac cgc ctt tcg gga tgg gga         528
Ser Pro Ile Ile Gly Val Thr Val Asn Tyr Arg Leu Ser Gly Trp Gly
                165                 170                 175 ttc ctc tat agc cag gaa gtc gcc gac gaa ggc tcc gcc aac tta gga         576
Phe Leu Tyr Ser Gln Glu Val Ala Asp Glu Gly Ser Ala Asn Leu Gly
            180                 185                 190 ctc cgc gac caa cgg cac gct ctg tac tgg ctc caa gag aat atc gct         624
Leu Arg Asp Gln Arg His Ala Leu Tyr Trp Leu Gln Glu Asn Ile Ala
        195                 200                 205 tcc ttc ggc ggc gac ccg tcg cgg ctc acc atc tgg ggc caa agt gcc         672
Ser Phe Gly Gly Asp Pro Ser Arg Leu Thr Ile Trp Gly Gln Ser Ala
    210                 215                 220 ggt gcc aac agc gtc ggt ctc cat tta gtg gca tac gac ggc cag aat         720
Gly Ala Asn Ser Val Gly Leu His Leu Val Ala Tyr Asp Gly Gln Asn
225                 230                 235                 240 gat ggc atc ttc cgt gcc ggg atc gcc gag agc ggc tcc gta ccc tcc         768
Asp Gly Ile Phe Arg Ala Gly Ile Ala Glu Ser Gly Ser Val Pro Ser
                245                 250                 255 ctc gca gca tac atg agc gcc gaa gat gca caa cca tac tat gat gcc         816
Leu Ala Ala Tyr Met Ser Ala Glu Asp Ala Gln Pro Tyr Tyr Asp Ala
            260                 265                 270 gtc gtc aac gca acc aac tgc acc ggc tct tcc aac acc ctt act tgt         864
Val Val Asn Ala Thr Asn Cys Thr Gly Ser Ser Asn Thr Leu Thr Cys
        275                 280                 285 ctc cgt gaa gtt ccc acc gac gtc ctc agc tcc atc ttc aac agc tcc         912
Leu Arg Glu Val Pro Thr Asp Val Leu Ser Ser Ile Phe Asn Ser Ser
    290                 295                 300 ctc gtc gct ggg gca gga tat cat ccc gtc att gac ggc gat ttc ctc         960
Leu Val Ala Gly Ala Gly Tyr His Pro Val Ile Asp Gly Asp Phe Leu
305                 310                 315                 320 aga gcc tcg ggg ata gtt aat ctc cag act ggc caa ttc gcc aaa acc         1008
```

```
Arg Ala Ser Gly Ile Val Asn Leu Gln Thr Gly Gln Phe Ala Lys Thr
                325                 330                 335 ccg ctt ctt atc ggc acc aac ttc gac gaa ggg acc aag tat gcc cct    1056
Pro Leu Leu Ile Gly Thr Asn Phe Asp Glu Gly Thr Lys Tyr Ala Pro
                340                 345                 350 cat ggc tat aat acc acc gac caa ttt gtc tcc ctc gtc caa gcc aac    1104
His Gly Tyr Asn Thr Thr Asp Gln Phe Val Ser Leu Val Gln Ala Asn
                355                 360                 365 gga acc aat tat acc agc gct ctc acc att gca tcc ctg tac cca gat    1152
Gly Thr Asn Tyr Thr Ser Ala Leu Thr Ile Ala Ser Leu Tyr Pro Asp
        370                 375                 380 gac cca gcc gtt ggt att ccg gga acc ctt caa ggt cgt ccc cca ccg    1200
Asp Pro Ala Val Gly Ile Pro Gly Thr Leu Gln Gly Arg Pro Pro Pro
385                 390                 395                 400 tca tac ggt tac cag tgg aag cgc gtg gct gcc ttc ctc ggc gat ctg    1248
Ser Tyr Gly Tyr Gln Trp Lys Arg Val Ala Ala Phe Leu Gly Asp Leu
                405                 410                 415 ctc atg cac gcg cct cgc cgc gtg aca acc cag tgg ctg gca cac tgg    1296
Leu Met His Ala Pro Arg Arg Val Thr Thr Gln Trp Leu Ala His Trp
                420                 425                 430 aat gta cct gcc tac gtg tat cac tgg aac gtg atg aca cta ggg cca    1344
Asn Val Pro Ala Tyr Val Tyr His Trp Asn Val Met Thr Leu Gly Pro
                435                 440                 445 tta gat gga gcc gcg cat ggc tat gaa gtc ccc ttc agt ttc cat aat    1392
Leu Asp Gly Ala Ala His Gly Tyr Glu Val Pro Phe Ser Phe His Asn
        450                 455                 460 tat gat ggt ttg ggc gat gaa cgg gga aac gac agc gtg acc tgg cca    1440
Tyr Asp Gly Leu Gly Asp Glu Arg Gly Asn Asp Ser Val Thr Trp Pro
465                 470                 475                 480 caa cta tcg act atg atg tca cgg atg tgg gtg agc ttt att aat cat    1488
Gln Leu Ser Thr Met Met Ser Arg Met Trp Val Ser Phe Ile Asn His
                485                 490                 495 ttg gat ccg aat tat agt aat agt gag tga                            1518
Leu Asp Pro Asn Tyr Ser Asn Ser Glu
                500                 505

<210> SEQ ID NO 27
<211> LENGTH: 505
<212> TYPE: PRT
<213> ORGANISM: Aspergillus niger

<400> SEQUENCE: 27

Met Ala Ser Ser Val Phe Leu Pro Leu Leu Ala Ala Ser Leu Leu Pro
1               5                   10                  15

Thr Leu Ala Ser Thr Gln Asn Ala Asp Thr Pro Thr Ser Ala Pro Thr
                20                  25                  30

Val Gln Val Arg Asn Gly Thr Tyr Glu Gly Leu Tyr Asn Pro Thr Tyr
            35                  40                  45

Asn Gln Asp Leu Phe Leu Gly Ile Pro Tyr Ala Gln Pro Pro Val Gly
        50                  55                  60

Glu Leu Arg Phe Arg Pro Pro Gln Pro Leu Asn Thr Thr Trp Thr Gly
65                  70                  75                  80

Thr Arg Asn Ala Thr Ala Tyr Tyr Asn Glu Cys Ile Gly Tyr Gly Ser
                85                  90                  95

Asp Asp Trp Tyr Trp Thr Asp Val Val Ser Glu Asp Cys Leu Ala Leu
                100                 105                 110

Ser Val Ile Arg Pro His Gly Ile Asp Ser Ser Ala Lys Leu Pro Val
            115                 120                 125

Val Phe Trp Met His Gly Gly Glu Phe Ala Glu Gly Gly Thr Arg Asp
```

```
                130                 135                 140
Ser Arg Tyr Asn Leu Ser Tyr Ile Val Gln Gln Ser Gln Glu Met Gln
145                 150                 155                 160

Ser Pro Ile Ile Gly Val Thr Val Asn Tyr Arg Leu Ser Gly Trp Gly
            165                 170                 175

Phe Leu Tyr Ser Gln Glu Val Ala Asp Glu Gly Ser Ala Asn Leu Gly
            180                 185                 190

Leu Arg Asp Gln Arg His Ala Leu Tyr Trp Leu Gln Glu Asn Ile Ala
            195                 200                 205

Ser Phe Gly Gly Asp Pro Ser Arg Leu Thr Ile Trp Gly Gln Ser Ala
210                 215                 220

Gly Ala Asn Ser Val Gly Leu His Leu Val Ala Tyr Asp Gly Gln Asn
225                 230                 235                 240

Asp Gly Ile Phe Arg Ala Gly Ile Ala Glu Ser Gly Ser Val Pro Ser
            245                 250                 255

Leu Ala Ala Tyr Met Ser Ala Glu Asp Ala Gln Pro Tyr Tyr Asp Ala
            260                 265                 270

Val Val Asn Ala Thr Asn Cys Thr Gly Ser Ser Asn Thr Leu Thr Cys
            275                 280                 285

Leu Arg Glu Val Pro Thr Asp Val Leu Ser Ser Ile Phe Asn Ser Ser
290                 295                 300

Leu Val Ala Gly Ala Tyr His Pro Val Ile Asp Gly Asp Phe Leu
305                 310                 315                 320

Arg Ala Ser Gly Ile Val Asn Leu Gln Thr Gly Gln Phe Ala Lys Thr
            325                 330                 335

Pro Leu Leu Ile Gly Thr Asn Phe Asp Glu Gly Thr Lys Tyr Ala Pro
            340                 345                 350

His Gly Tyr Asn Thr Thr Asp Gln Phe Val Ser Leu Val Gln Ala Asn
            355                 360                 365

Gly Thr Asn Tyr Thr Ser Ala Leu Thr Ile Ala Ser Leu Tyr Pro Asp
370                 375                 380

Asp Pro Ala Val Gly Ile Pro Gly Thr Leu Gln Gly Arg Pro Pro
385                 390                 395                 400

Ser Tyr Gly Tyr Gln Trp Lys Arg Val Ala Ala Phe Leu Gly Asp Leu
            405                 410                 415

Leu Met His Ala Pro Arg Arg Val Thr Thr Gln Trp Leu Ala His Trp
            420                 425                 430

Asn Val Pro Ala Tyr Val Tyr His Trp Asn Val Met Thr Leu Gly Pro
            435                 440                 445

Leu Asp Gly Ala Ala His Gly Tyr Glu Val Pro Phe Ser Phe His Asn
450                 455                 460

Tyr Asp Gly Leu Gly Asp Glu Arg Gly Asn Asp Ser Val Thr Trp Pro
465                 470                 475                 480

Gln Leu Ser Thr Met Met Ser Arg Met Trp Val Ser Phe Ile Asn His
            485                 490                 495

Leu Asp Pro Asn Tyr Ser Asn Ser Glu
            500                 505

<210> SEQ ID NO 28
<211> LENGTH: 3091
<212> TYPE: DNA
<213> ORGANISM: Aspergillus niger

<400> SEQUENCE: 28
ggcgaacggg cctgagcgtg cgtcggaggc agaagtagag ccgggactat ggatattggc    60
```

```
gaggaatata ttatagtaga ttatagggag tcgaatgcag ctcggattgg gttgttactt    120
tgagtcagat ggacattgtt ggaaaagatg aacgcgacgg gaaaaaaaca tgaggatttg    180
cggggatttc gtcacatgcg gaggcgcgga ttttcccctc cggatttact tcctcaactc    240
tcctttctct ttcatttcca tccgatttga gtccaactca tctcactcga agaatctcat    300
taatttcagg gtcctgctca gcccagtcaa ggttccttag tttcgatcct tcagttggcc    360
cgtcatgtcc attgaccagg aatggagcaa gccccgatga ggatcggcca gcggagacaa    420
ctgccaatcc ttggtatcca tacccttaac agcgcaatgg caccagctct ctgccgattc    480
acgtcatctg cacagcctag ctgccgatta ggcttgaccc cttctcactt gcggcatcag    540
tgccgctgat actagccccc acagagtgtt tctcccttcg actgtggctc ggaacgtggg    600
ggcgggttcc aagttcttat gcccagagtt ggttggctag ccttgctcat ctgggtggcc    660
agcacacctc ccatacaata ggatccgtgg tgttggcagg attcttgtca tttcgccatg    720
tcgaatcacc gcatgcggaa ggaggacgcc ttgccttgca atgttttctc cacatctgcg    780
accctattgt tcagaccctg gagccgattc cgcgagatgt attcctgccg gccactgaa    840 agtgctttat aacgtctggg gtgtccttt attgatgaga gcatgatctt tcgcgttaca    900
gttctcacaa tcggttaaag cattcgtggc cccgaggctc gttgcacaac acaatatgat    960
tttctttcat ctggcaccgt tcttctttct ctttggtcta gtagtatctt ctcagaaccc   1020
tacggtggac cttggctaca caagatataa aggcaaatct ctgcccaatg gtatcagtca   1080
gtggctgggg atacgctacg cggctgcacc taccgggtct ctgcggttct ctgcgccaca   1140
ggatcctgac acggtagatg gcgttcaaga agcattcaag gtatggtttt ttctacaata   1200
aataaaaaga tatattgcga gtctgtgctt tgctaatacc cagggcacag catggtcccc   1260
ggtgtgttcc caccagccaa tatcccactc ccgcaggcac gtccgaggat tgtctcttcc   1320
tcgatgtata cgctcccagc tcggtggaag ctactacgag gctgcccgtt ttcgtttgga   1380
ttcaaggagg cggcttcaat gccaactcca gccccaacta caatggaaca ggattgatcg   1440
aagcggccaa tatgtccatg gtggtggtca ccttcaacta cagggtcggt ccgtacgggt   1500
tcctctctgg atccgaggtg ctggagggag gaagcgtgaa caatggcctg aaggaccaaa   1560
tcaaggtcct gaagtgggtg caagagcata tcagcaaggt atgcggacac tcaccaaccc   1620
acagcaaatc accgctaatt gcagccgcag tttggaggcg atcccagtca cgttgttatc   1680
ggcggcgaca gcgcaggcgc agcgtctatc actctccatc tttcagccca cggtggcaga   1740
gacgacgaac tattccacgc tgccgccgca gagtcccaaa gctttgctcc tatgttgacc   1800
gtcaatcaaa gccaattcgc ctataacaac ctggtcatcc gcgccggctg cgcaagcgat   1860
tcagacaccc tcgcctgctt acgccgacta aacaccacag aactgcagcg catcaacatc   1920
aacacaccct acccaccgc ccaacaagca cctctctacc tgtacggtcc cgtcgtcgac   1980
ggctccctca tcccagacta cacataccgg cttttccagc aaggcaaatt catcaaagtc   2040
cccgtaatct tcggcgacga caccaacgaa ggaacaatct tcgtcccaa aacgacctcc   2100 accgtcggcg aagccgacac cttcatccaa gaccaattcc ccaacatcaa cttcacccac   2160
ctaaccaagc tgaacgactg gtatctcaaa gaaaaccaaa ctcgcgagtt ccccaattcc   2220 tcccctact ggcgtcccgc tagcaccgcg tacggtgaaa tcagatatat ctgtccgggg   2280
atctacatgt cctctgtgtt tgctagtgcc ggtgtcaaca gctggaacta tcattatgct   2340
gtgcaggacc ccgccgcgga agcctcaggc agaggtgtca gtcatactgt ggaagaaaat   2400
gccatttggg gcccgcagta tgtgagtggc acaccgccgg cgtcgtatct cactgagaat   2460
```

-continued

```
gcgccaattg tgccggtgat gcagggctac tggacgagtt tcattagagt gtttgatccg    2520
aatccgctga ggtatccggg gagtccggag tggaagacgt ggagtgatgg acatggggag    2580
gattatcggc ggatatttgt ccgcacgaat gagacgagga tggagacggt gtcggaggcg    2640
cagagggaaa ggtgcgaata ttggagtagt gttgggccgg acttgtcgca gtgattgcac    2700
ttattatctt tgttcggtgg taaggtatat atatagatag tataatattg taagctatag    2760
agtgatggta cgtgaattga atatatggag aaagatggtc ttgtataaat caaaacattc    2820
ttttttggct gccattccac gatcatcatt cccaatgatc aaaccaagta actataaccg    2880
aatatataca tctatatcaa cctgcttctc atcagaatta ccaaaagacg ggtccggcac    2940
acacagctag accgagcaga tacgtcgaca tgaacccagg tgatgaaaca taatgcaaca    3000
aaagaaagag aaaagaaggc aaaacaagtg agaagcacta ctgctccaca tagagcagta    3060
aacgaacgat gaatgaggga tatcatcatc a                                  3091
```

<210> SEQ ID NO 29
<211> LENGTH: 1617
<212> TYPE: DNA
<213> ORGANISM: Aspergillus niger
<220> FEATURE:
<221> NAME/KEY: CDS
<222> LOCATION: (1)..(1617)

<400> SEQUENCE: 29

```
atg att ttc ttt cat ctg gca ccg ttc ttc ttt ctc ttt ggt cta gta      48
Met Ile Phe Phe His Leu Ala Pro Phe Phe Phe Leu Phe Gly Leu Val
1               5                   10                  15 gta tct tct cag aac cct acg gtg gac ctt ggc tac aca aga tat aaa      96
Val Ser Ser Gln Asn Pro Thr Val Asp Leu Gly Tyr Thr Arg Tyr Lys
            20                  25                  30 ggc aaa tct ctg ccc aat ggt atc agt cag tgg ctg ggg ata cgc tac     144
Gly Lys Ser Leu Pro Asn Gly Ile Ser Gln Trp Leu Gly Ile Arg Tyr
        35                  40                  45 gcg gct gca cct acc ggg tct ctg cgg ttc tct gcg cca cag gat cct     192
Ala Ala Ala Pro Thr Gly Ser Leu Arg Phe Ser Ala Pro Gln Asp Pro
    50                  55                  60 gac acg gta gat ggc gtt caa gaa gca ttc aag cat ggt ccc cgg tgt     240
Asp Thr Val Asp Gly Val Gln Glu Ala Phe Lys His Gly Pro Arg Cys
65                  70                  75                  80 gtt ccc acc agc caa tat ccc act ccc gca ggc acg tcc gag gat tgt     288
Val Pro Thr Ser Gln Tyr Pro Thr Pro Ala Gly Thr Ser Glu Asp Cys
                85                  90                  95 ctc ttc ctc gat gta tac gct ccc agc tcg gtg gaa gct act acg agg     336
Leu Phe Leu Asp Val Tyr Ala Pro Ser Ser Val Glu Ala Thr Thr Arg
            100                 105                 110 ctg ccc gtt ttc gtt tgg att caa gga ggc ggc ttc aat gcc aac tcc     384
Leu Pro Val Phe Val Trp Ile Gln Gly Gly Gly Phe Asn Ala Asn Ser
        115                 120                 125 agc ccc aac tac aat gga aca gga ttg atc gaa gcg gcc aat atg tcc     432
Ser Pro Asn Tyr Asn Gly Thr Gly Leu Ile Glu Ala Ala Asn Met Ser
    130                 135                 140 atg gtg gtg gtc acc ttc aac tac agg gtc ggt ccg tac ggg ttc ctc     480
Met Val Val Val Thr Phe Asn Tyr Arg Val Gly Pro Tyr Gly Phe Leu
145                 150                 155                 160 tct gga tcc gag gtg ctg gag gga gga agc gtg aac aat ggc ctg aag     528
Ser Gly Ser Glu Val Leu Glu Gly Gly Ser Val Asn Asn Gly Leu Lys
                165                 170                 175 gac caa atc aag gtc ctg aag tgg gtg caa gag cat atc agc aag ttt     576
Asp Gln Ile Lys Val Leu Lys Trp Val Gln Glu His Ile Ser Lys Phe
```

```
                180                 185                 190
gga ggc gat ccc agt cac gtt gtt atc ggc ggc gac agc gca ggc gca      624
Gly Gly Asp Pro Ser His Val Val Ile Gly Gly Asp Ser Ala Gly Ala
            195                 200                 205 gcg tct atc act ctc cat ctt tca gcc cac ggt ggc aga gac gac gaa      672
Ala Ser Ile Thr Leu His Leu Ser Ala His Gly Gly Arg Asp Asp Glu
210                 215                 220 cta ttc cac gct gcc gcc gca gag tcc caa agc ttt gct cct atg ttg      720
Leu Phe His Ala Ala Ala Ala Glu Ser Gln Ser Phe Ala Pro Met Leu
225                 230                 235                 240 acc gtc aat caa agc caa ttc gcc tat aac aac ctg gtc atc cgc gcc      768
Thr Val Asn Gln Ser Gln Phe Ala Tyr Asn Asn Leu Val Ile Arg Ala
            245                 250                 255 ggc tgc gca agc gat tca gac acc ctc gcc tgc tta cgc cga cta aac      816
Gly Cys Ala Ser Asp Ser Asp Thr Leu Ala Cys Leu Arg Arg Leu Asn
            260                 265                 270 acc aca gaa ctg cag cgc atc aac atc aac aca ccc tta ccc acc gcc      864
Thr Thr Glu Leu Gln Arg Ile Asn Ile Asn Thr Pro Leu Pro Thr Ala
            275                 280                 285 caa caa gca cct ctc tac ctg tac ggt ccc gtc gtc gac ggc tcc ctc      912
Gln Gln Ala Pro Leu Tyr Leu Tyr Gly Pro Val Val Asp Gly Ser Leu
            290                 295                 300 atc cca gac tac aca tac cgg ctt ttc cag caa ggc aaa ttc atc aaa      960
Ile Pro Asp Tyr Thr Tyr Arg Leu Phe Gln Gln Gly Lys Phe Ile Lys
305                 310                 315                 320 gtc ccc gta atc ttc ggc gac gac acc aac gaa gga aca atc ttc gtc     1008
Val Pro Val Ile Phe Gly Asp Asp Thr Asn Glu Gly Thr Ile Phe Val
            325                 330                 335 ccc aaa acg acc tcc acc gtc ggc gaa gcc gac acc ttc atc caa gac     1056
Pro Lys Thr Thr Ser Thr Val Gly Glu Ala Asp Thr Phe Ile Gln Asp
            340                 345                 350 caa ttc ccc aac atc aac ttc acc cac cta acc aag ctg aac gac tgg     1104
Gln Phe Pro Asn Ile Asn Phe Thr His Leu Thr Lys Leu Asn Asp Trp
            355                 360                 365 tat ctc aaa gaa aac caa act cgc gag ttc ccc aat tcc tcc ccc tac     1152
Tyr Leu Lys Glu Asn Gln Thr Arg Glu Phe Pro Asn Ser Ser Pro Tyr
370                 375                 380 tgg cgt ccc gct agc acc gcg tac ggt gaa atc aga tat atc tgt ccg     1200
Trp Arg Pro Ala Ser Thr Ala Tyr Gly Glu Ile Arg Tyr Ile Cys Pro
385                 390                 395                 400 ggg atc tac atg tcc tct gtg ttt gct agt gcc ggt gtc aac agc tgg     1248
Gly Ile Tyr Met Ser Ser Val Phe Ala Ser Ala Gly Val Asn Ser Trp
            405                 410                 415 aac tat cat tat gct gtg cag gac ccc gcc gcg gaa gcc tca ggc aga     1296
Asn Tyr His Tyr Ala Val Gln Asp Pro Ala Ala Glu Ala Ser Gly Arg
            420                 425                 430 ggt gtc agt cat act gtg gaa gaa aat gcc att tgg ggc ccg cag tat     1344
Gly Val Ser His Thr Val Glu Glu Asn Ala Ile Trp Gly Pro Gln Tyr
            435                 440                 445 gtg agt ggc aca ccg ccg gcg tcg tat ctc act gag aat gcg cca att     1392
Val Ser Gly Thr Pro Pro Ala Ser Tyr Leu Thr Glu Asn Ala Pro Ile
450                 455                 460 gtg ccg gtg atg cag ggc tac tgg acg agt ttc att aga gtg ttt gat     1440
Val Pro Val Met Gln Gly Tyr Trp Thr Ser Phe Ile Arg Val Phe Asp
465                 470                 475                 480 ccg aat ccg ctg agg tat ccg ggg agt ccg gag tgg aag acg tgg agt     1488
Pro Asn Pro Leu Arg Tyr Pro Gly Ser Pro Glu Trp Lys Thr Trp Ser
            485                 490                 495 gat gga cat ggg gag gat tat cgg cgg ata ttt gtc cgc acg aat gag     1536
Asp Gly His Gly Glu Asp Tyr Arg Arg Ile Phe Val Arg Thr Asn Glu
```

```
                500             505             510
acg agg atg gag acg gtg tcg gag gcg cag agg gaa agg tgc gaa tat   1584
Thr Arg Met Glu Thr Val Ser Glu Ala Gln Arg Glu Arg Cys Glu Tyr
        515                 520                 525 tgg agt agt gtt ggg ccg gac ttg tcg cag tga                       1617
Trp Ser Ser Val Gly Pro Asp Leu Ser Gln
530                 535

<210> SEQ ID NO 30
<211> LENGTH: 538
<212> TYPE: PRT
<213> ORGANISM: Aspergillus niger

<400> SEQUENCE: 30

Met Ile Phe Phe His Leu Ala Pro Phe Phe Leu Phe Gly Leu Val
1               5                   10                  15

Val Ser Ser Gln Asn Pro Thr Val Asp Leu Gly Tyr Thr Arg Tyr Lys
            20                  25                  30

Gly Lys Ser Leu Pro Asn Gly Ile Ser Gln Trp Leu Gly Ile Arg Tyr
            35                  40                  45

Ala Ala Ala Pro Thr Gly Ser Leu Arg Phe Ser Ala Pro Gln Asp Pro
50                  55                  60

Asp Thr Val Asp Gly Val Gln Glu Ala Phe Lys His Gly Pro Arg Cys
65              70                  75                      80

Val Pro Thr Ser Gln Tyr Pro Thr Pro Ala Gly Thr Ser Glu Asp Cys
                85                  90                  95

Leu Phe Leu Asp Val Tyr Ala Pro Ser Ser Val Glu Ala Thr Thr Arg
                100                 105                 110

Leu Pro Val Phe Val Trp Ile Gln Gly Gly Gly Phe Asn Ala Asn Ser
            115                 120                 125

Ser Pro Asn Tyr Asn Gly Thr Gly Leu Ile Glu Ala Ala Asn Met Ser
130                 135                 140

Met Val Val Val Thr Phe Asn Tyr Arg Val Gly Pro Tyr Gly Phe Leu
145                 150                 155                 160

Ser Gly Ser Glu Val Leu Glu Gly Gly Ser Val Asn Asn Gly Leu Lys
                165                 170                 175

Asp Gln Ile Lys Val Leu Lys Trp Val Gln Glu His Ile Ser Lys Phe
            180                 185                 190

Gly Gly Asp Pro Ser His Val Val Ile Gly Gly Asp Ser Ala Gly Ala
        195                 200                 205

Ala Ser Ile Thr Leu His Ser Ala His Gly Arg Asp Asp Glu
210                 215                 220

Leu Phe His Ala Ala Ala Glu Ser Gln Ser Phe Ala Pro Met Leu
225                 230                 235                 240

Thr Val Asn Gln Ser Gln Phe Ala Tyr Asn Asn Leu Val Ile Arg Ala
            245                 250                 255

Gly Cys Ala Ser Asp Ser Asp Thr Leu Ala Cys Leu Arg Arg Leu Asn
            260                 265                 270

Thr Thr Glu Leu Gln Arg Ile Asn Ile Asn Thr Pro Leu Pro Thr Ala
            275                 280                 285

Gln Gln Ala Pro Leu Tyr Leu Tyr Gly Pro Val Val Asp Gly Ser Leu
290                 295                 300

Ile Pro Asp Tyr Thr Tyr Arg Leu Phe Gln Gln Gly Lys Phe Ile Lys
305                 310                 315                 320

Val Pro Val Ile Phe Gly Asp Asp Thr Asn Glu Gly Thr Ile Phe Val
                325                 330                 335
```

```
Pro Lys Thr Thr Ser Thr Val Gly Glu Ala Asp Thr Phe Ile Gln Asp
            340                 345                 350

Gln Phe Pro Asn Ile Asn Phe Thr His Leu Thr Lys Leu Asn Asp Trp
        355                 360                 365

Tyr Leu Lys Glu Asn Gln Thr Arg Glu Phe Pro Asn Ser Ser Pro Tyr
    370                 375                 380

Trp Arg Pro Ala Ser Thr Ala Tyr Gly Glu Ile Arg Tyr Ile Cys Pro
385                 390                 395                 400

Gly Ile Tyr Met Ser Ser Val Phe Ala Ser Ala Gly Val Asn Ser Trp
                405                 410                 415

Asn Tyr His Tyr Ala Val Gln Asp Pro Ala Ala Glu Ala Ser Gly Arg
            420                 425                 430

Gly Val Ser His Thr Val Glu Glu Asn Ala Ile Trp Gly Pro Gln Tyr
                435                 440                 445

Val Ser Gly Thr Pro Pro Ala Ser Tyr Leu Thr Glu Asn Ala Pro Ile
    450                 455                 460

Val Pro Val Met Gln Gly Tyr Trp Thr Ser Phe Ile Arg Val Phe Asp
465                 470                 475                 480

Pro Asn Pro Leu Arg Tyr Pro Gly Ser Pro Glu Trp Lys Thr Trp Ser
                485                 490                 495

Asp Gly His Gly Glu Asp Tyr Arg Arg Ile Phe Val Arg Thr Asn Glu
            500                 505                 510

Thr Arg Met Glu Thr Val Ser Glu Ala Gln Arg Glu Arg Cys Glu Tyr
                515                 520                 525

Trp Ser Ser Val Gly Pro Asp Leu Ser Gln
    530                 535

<210> SEQ ID NO 31
<211> LENGTH: 4575
<212> TYPE: DNA
<213> ORGANISM: Aspergillus niger

<400> SEQUENCE: 31
gatgcaactt cagtgaaatt gagacgattg taactcatca tcgcatctca catggaaagg      60
ttgtacaccc aacaattaga cctcaacata tttcacggat attcctgcaa gatatataat     120
aaagccatca ctccactttg gtagatatgt tagccaaccg ggtttgagcg agtttcttga     180
atggactcat taagggtagg atcaattctg atgtccacaa ttggtcccta tttgccagat     240
gtaggcccag agaattcggt atcttgcaga tttgcgatgc tatcccggtt tccagtaaac     300
tattaggttc ggctcggtca caccagacag acacgactga cccatgcgct gccaggaatc     360
ctgataggcc tagcagtccc gcgtgcacat atcggcttgg tagaaaagga tagccgtgaa     420
tgtataatct ttcagatgac ggttaaatgc gtttctgtat ggtgagaagc tgtgtagatg     480
ggagatgagc tgtaaatggc ttcgcagtgg caacctctag gctgctgcag gccgaaatac     540
tgcatggcgt gattttcgtc gtgaatcttg ttcatataca ggtgtaaaac acacgtaagg     600
aaaatcttgt tatagcaggg ttgaaaacag ttgctagaat tggcagtgac tgttgcggtt     660
gcaagggttt attttgcacc cttgaagtac actgcgcttg gtcaaaggca aatcacccca     720
tcaagtaata aatatatatc tctgttatca agtcggctcc tctagtagtg cagcctcagt     780
acagacaaca gggactaaca gcactcttgc tgttgagctt gagcgcacct caccttctc      840 tccggcctct ttcgtatttg gcatttcaat ggcctgttat gggacttctg agcctgcttg     900
attgagtgat atggtagtgc gagcgcaaaa aaggtgattt tcaaacacca tgatgcaaag     960
```

```
tcagaggtaa gtgcgagagg gagatcagga ggaggagagc tttatataag gccgcgtagg   1020
cggcagagac ggcaagacat ctggtgaagt accagcattc agtgaatttt ataacagtat   1080
tatttgtcat cacgactctg cattgccttt aataagctcg gcgtaatttg gtagggaccc   1140
taggtttgga tagccccagg ggggcttggt gtcggttgtg gagcttgctg cccgagattc   1200
attttacacc tagtcaggga tccggcgggt tttataccct ccctggaggc ggaatgtacc   1260
tttgttatca ctgaaaattc cggccatttt gttctatttt actggctatg ggtttgcca   1320 ctatcgctca catcctcgca aggcacctcc cgatactgca gtcaaacgtg ggagttgccg   1380
atagaaacta caagatcaaa tctcgttccc tgggttggac ggtcacattc ggtgaaagag   1440
gtttatcttc gctccaacca gcctttcatg tcggcgctc agtgcataag atccaagcaa   1500
ttttaagcac tgtactccac tagtcacact gttttagcag tgcatgcttc tgaatcagga   1560
ctaaactccg atttttctca gtgaatactg ctaaagacaa ttatgatcct acagactatc   1620
tctgtgaaaa agcgcagtta acttctcgtc aatcatgaag ccattttgag cctttctccg   1680
tcaatcattc accCctactg ttgactatat cagccctaag ggaataaaac atttgccgta   1740
gaggtgaact ataactcaat caatgactga aagcttaacg tatctcacaa ttcatctcac   1800
cgtgaagagt catttacatt tacgatccag ccaggccgcg ctgacatcag caggcgtgag   1860
agcgcatcca tgcttgctcg gacataagcc gaatccattg catgatgcga ccttcccgaa   1920
agagtatggg tgtccgaact gaccatgtca gtggcccccat atggctctca actacacgaa   1980
cacagacctt tatcagtccc ggtccccaca acttaaatcc ggagatgcgg gggtgcagga   2040
atggaacacg gatacatgtg tggaatgtag gaccaaacaa attggctgtc gtggacattc   2100
gactcgactt gaccCctcaa tgcgctggcc ggaggactga gccatagggt ataagaacac   2160
cgtgatcact catgcctcgt tatcgctttt ctatcattat gtctcgatat caggaagaca   2220
tagcatgacc gtgaacacga tgaagggaat gctcccgacg cttagttggt tggcactggg   2280
catggccagc ctggcaacct gcaccaaccc agtagcccag acaaagaacg gaagttatta   2340
tggtgtctac atgcctcagt ataatgagga ttattttctt ggaattccat ttgctaagcc   2400
cccgttggca cacttgcgtt gggccaaccc cgagagtctt aatgagtctt ggtcgggatt   2460
gcgccctgct accggctatg cgatggtaag tagcctgaac agactgctaa cgaccatgt   2520 acttactaac agcgcgtgtg ataggaatgt ataggttacg gcagtgatca aaaggttat   2580 ctgcaggtga ggatttgacg ccactttctt tacgctgttc tctactaacc agcaaaatag   2640
agcgaggact gtctctacct aaacgtggtc cgtcccgctg aatacgacaa tgccagtctt   2700
ccagtccttg tatggattca tggtatgtag tgaaatctac ctcaacgaca agttactccc   2760
gacgctgaat gaacaaaaca ggcggtggct tcgcacaagg cggcactccc gaccttcgat   2820
acaatcttac atttattgtt gaacactcgg tcaatatcgg ccagccaatt atcgcagtga   2880
gcgttgccta tcgtctcggt ccttgggggtt tcttcaatgg ggtcgagctc gccaatgagg   2940
gatcgttaaa tctcgggctg aaggaccagc gcttggccct gcattgggtg aaagagaaca   3000
ttgcaggttt cggtggtggg tttccataaa gctattaaac gtacacagtc caaaattact   3060
aatgacagtc actcctatac aggcgaccct agtaaagtcg tgatttacgg acaaagtgcc   3120
ggctccgaaa gcgtgggata ccaaatccgc gcgtacaacg gccgagatga cgggctcttc   3180
cgcggaggca tgatggagtc cggcgcggtg ttacctggca gtgccttgaa cctcacctgg   3240
acatatgagc cttggttcca gcaaatagca gacgaggcag gatgttccca gaccaccgc   3300 aaactggact gtctacgccg cacgcccttc acagtcctaa acaacattct gaacaccacc   3360
```

-continued

```
gccaacgaca cgacgcctta caactggagg cccacagtgg acggtgactt cgtagcgcga   3420
tatcccagcg agcaactcga cacaggagac ttcgtcaaag taccaatcat aatcggctac   3480
accacggacg aaggaacaac agagtgccca gaaccagtga acaccaccgc gaattaaaa    3540 gaatacctca gctgtacgta cctccttccc ttcctcccct atccccccat ccccatccca   3600
ataacaccaa cccagcaaca caacctacg gctgggccct cgactcacag gtagtatcct    3660
cgctcctgga cctctacccc aacaccacct ccttcggcat cccatcatcc gaagaactcg   3720
gcggcaacgt caccttccca cagccctacg gcgccgcatt ccgccagacg gcagcatact   3780
acggcgacgc ccagttcata gccgcgacgc gctacacctg tgagctatgg gcggcacata   3840
acctgacagc atattgctac cgattcaaca ccaagacaga cgattacaac agggaagaag   3900
gcgtggcgca tttctcggac gtgatcttca tcttcaacaa ccttaatggt tatgggttca   3960
gtccgaaccc gttcaccaat gctccagaga gctatactga gcttagctac ctcatgtccg   4020
gctcgtggat cagcttcact aatagtctgg atcctaataa gtggactggt cgcggaagga   4080
acgctacgaa gacggagaat tggcccgtgt atgatctgga gaatcccttg agtatgatct   4140
gggatgcgaa tgtcacttcg tatgcggcgc cggatacttg gcgtaaggag ggtattgcgt   4200
tgattaatgc taatcggagg gcgtatcaga ggtgaatgtg gtgtagcttg cagccgttgc   4260
ctacttgttc gactttcaaa ctcaaaactt tctattgaga gagaaaattg tgcgaggaaa   4320
gtactaccgc gggcagaaca ctctgcgcac aggtccatat ctacaaactc actgaacaga   4380
gtctatagca gattaggtag attgtcaagc ttcatacag acataacccc accacaatat    4440
cgtggtaaga tagcacattt ctttaaagaa gaaaaaaaaa gatgaataca tataatcggc   4500
tacgtcaata attcaaaaca gaatatgtca gctgtgcaca catccgacca ttacactagt   4560
aaagtgagcg gcggc                                                    4575
```

<210> SEQ ID NO 32
<211> LENGTH: 1695
<212> TYPE: DNA
<213> ORGANISM: Aspergillus niger
<220> FEATURE:
<221> NAME/KEY: CDS
<222> LOCATION: (1)..(1695)

<400> SEQUENCE: 32

```
atg aag gga atg ctc ccg acg ctt agt tgg ttg gca ctg ggc atg gcc    48
Met Lys Gly Met Leu Pro Thr Leu Ser Trp Leu Ala Leu Gly Met Ala
 1               5                  10                  15 agc ctg gca acc tgc acc aac cca gta gcc cag aca aag aac gga agt    96
Ser Leu Ala Thr Cys Thr Asn Pro Val Ala Gln Thr Lys Asn Gly Ser
             20                  25                  30 tat tat ggt gtc tac atg cct cag tat aat gag gat tat ttt ctt gga   144
Tyr Tyr Gly Val Tyr Met Pro Gln Tyr Asn Glu Asp Tyr Phe Leu Gly
         35                  40                  45 att cca ttt gct aag ccc ccg ttg gca cac ttg cgt tgg gcc aac ccc   192
Ile Pro Phe Ala Lys Pro Pro Leu Ala His Leu Arg Trp Ala Asn Pro
     50                  55                  60 gag agt ctt aat gag tct tgg tcg gga ttg cgc cct gct acc ggc tat   240
Glu Ser Leu Asn Glu Ser Trp Ser Gly Leu Arg Pro Ala Thr Gly Tyr
 65                  70                  75                  80 gcg atg gaa tgt ata ggt tac ggc agt gat caa aaa ggt tat ctg cag   288
Ala Met Glu Cys Ile Gly Tyr Gly Ser Asp Gln Lys Gly Tyr Leu Gln
                 85                  90                  95 agc gag gac tgt ctc tac cta aac gtg gtc cgt ccc gct gaa tac gac   336
Ser Glu Asp Cys Leu Tyr Leu Asn Val Val Arg Pro Ala Glu Tyr Asp
            100                 105                 110
```

```
aat gcc agt ctt cca gtc ctt gta tgg att cat ggc ggt ggc ttc gca      384
Asn Ala Ser Leu Pro Val Leu Val Trp Ile His Gly Gly Gly Phe Ala
        115                 120                 125 caa ggc ggc act ccc gac ctt cga tac aat ctt aca ttt att gtt gaa      432
Gln Gly Gly Thr Pro Asp Leu Arg Tyr Asn Leu Thr Phe Ile Val Glu
130                 135                 140 cac tcg gtc aat atc ggc cag cca att atc gca gtg agc gtt gcc tat      480
His Ser Val Asn Ile Gly Gln Pro Ile Ile Ala Val Ser Val Ala Tyr
145                 150                 155                 160 cgt ctc ggt cct tgg ggt ttc ttc aat ggg gtc gag ctc gcc aat gag      528
Arg Leu Gly Pro Trp Gly Phe Phe Asn Gly Val Glu Leu Ala Asn Glu
                165                 170                 175 gga tcg tta aat ctc ggg ctg aag gac cag cgc ttg gcc ctg cat tgg      576
Gly Ser Leu Asn Leu Gly Leu Lys Asp Gln Arg Leu Ala Leu His Trp
            180                 185                 190 gtg aaa gag aac att gca ggt ttc ggt ggc gac cct agt aaa gtc gtg      624
Val Lys Glu Asn Ile Ala Gly Phe Gly Gly Asp Pro Ser Lys Val Val
        195                 200                 205 att tac gga caa agt gcc ggc tcc gaa agc gtg gga tac caa atc cgc      672
Ile Tyr Gly Gln Ser Ala Gly Ser Glu Ser Val Gly Tyr Gln Ile Arg
    210                 215                 220 gcg tac aac ggc cga gat gac ggg ctc ttc cgc gga ggc atg atg gag      720
Ala Tyr Asn Gly Arg Asp Asp Gly Leu Phe Arg Gly Gly Met Met Glu
225                 230                 235                 240 tcc ggc gcg gtg tta cct ggc agt gcc ttg aac ctc acc tgg aca tat      768
Ser Gly Ala Val Leu Pro Gly Ser Ala Leu Asn Leu Thr Trp Thr Tyr
                245                 250                 255 gag cct tgg ttc cag caa ata gca gac gag gca gga tgt tcc cag acc      816
Glu Pro Trp Phe Gln Gln Ile Ala Asp Glu Ala Gly Cys Ser Gln Thr
            260                 265                 270 acc cgc aaa ctg gac tgt cta cgc cgc acg ccc ttc aca gtc cta aac      864
Thr Arg Lys Leu Asp Cys Leu Arg Arg Thr Pro Phe Thr Val Leu Asn
        275                 280                 285 aac att ctg aac acc acc gcc aac gac acg acg cct tac aac tgg agg      912
Asn Ile Leu Asn Thr Thr Ala Asn Asp Thr Thr Pro Tyr Asn Trp Arg
    290                 295                 300 ccc aca gtg gac ggt gac ttc gta gcg cga tat ccc agc gag caa ctc      960
Pro Thr Val Asp Gly Asp Phe Val Ala Arg Tyr Pro Ser Glu Gln Leu
305                 310                 315                 320 gac aca gga gac ttc gtc aaa gta cca atc ata atc ggc tac acc acg     1008
Asp Thr Gly Asp Phe Val Lys Val Pro Ile Ile Ile Gly Tyr Thr Thr
                325                 330                 335 gac gaa gga aca aca gag tgc cca gaa cca gtg aac acc acc gcc gaa     1056
Asp Glu Gly Thr Thr Glu Cys Pro Glu Pro Val Asn Thr Thr Ala Glu
            340                 345                 350 tta aaa gaa tac ctc agc tca aca aca acc tac ggc tgg gcc ctc gac     1104
Leu Lys Glu Tyr Leu Ser Ser Thr Thr Thr Tyr Gly Trp Ala Leu Asp
        355                 360                 365 tca cag gta gta tcc tcg ctc ctg gac ctc tac ccc aac acc acc tcc     1152
Ser Gln Val Val Ser Ser Leu Leu Asp Leu Tyr Pro Asn Thr Thr Ser
    370                 375                 380 ttc ggc atc cca tca tcc gaa gaa ctc ggc ggc aac gtc acc ttc cca     1200
Phe Gly Ile Pro Ser Ser Glu Glu Leu Gly Gly Asn Val Thr Phe Pro
385                 390                 395                 400 cag ccc tac ggc gcc gca ttc cgc cag acg gca tac tac ggc gac         1248
Gln Pro Tyr Gly Ala Ala Phe Arg Gln Thr Ala Tyr Tyr Gly Asp
                405                 410                 415 gcc cag ttc ata gcc gcg acg cgc tac acc tgt gag cta tgg gcg gca     1296
Ala Gln Phe Ile Ala Ala Thr Arg Tyr Thr Cys Glu Leu Trp Ala Ala
            420                 425                 430
```

```
cat aac ctg aca gca tat tgc tac cga ttc aac acc aag aca gac gat     1344
His Asn Leu Thr Ala Tyr Cys Tyr Arg Phe Asn Thr Lys Thr Asp Asp
        435                 440                 445 tac aac agg gaa gaa ggc gtg gcg cat ttc tcg gac gtg atc ttc atc     1392
Tyr Asn Arg Glu Glu Gly Val Ala His Phe Ser Asp Val Ile Phe Ile
450                 455                 460 ttc aac aac ctt aat ggt tat ggg ttc agt ccg aac ccg ttc acc aat     1440
Phe Asn Asn Leu Asn Gly Tyr Gly Phe Ser Pro Asn Pro Phe Thr Asn
465                 470                 475                 480 gct cca gag agc tat act gag ctt agc tac ctc atg tcc ggc tcg tgg     1488
Ala Pro Glu Ser Tyr Thr Glu Leu Ser Tyr Leu Met Ser Gly Ser Trp
                485                 490                 495 atc agc ttc act aat agt ctg gat cct aat aag tgg act ggt cgc gga     1536
Ile Ser Phe Thr Asn Ser Leu Asp Pro Asn Lys Trp Thr Gly Arg Gly
            500                 505                 510 agg aac gct acg aag acg gag aat tgg ccc gtg tat gat ctg gag aat     1584
Arg Asn Ala Thr Lys Thr Glu Asn Trp Pro Val Tyr Asp Leu Glu Asn
        515                 520                 525 ccc ttg agt atg atc tgg gat gcg aat gtc act tcg tat gcg gcg ccg     1632
Pro Leu Ser Met Ile Trp Asp Ala Asn Val Thr Ser Tyr Ala Ala Pro
530                 535                 540 gat act tgg cgt aag gag ggt att gcg ttg att aat gct aat cgg agg     1680
Asp Thr Trp Arg Lys Glu Gly Ile Ala Leu Ile Asn Ala Asn Arg Arg
545                 550                 555                 560 gcg tat cag agg tga                                                  1695
Ala Tyr Gln Arg <210> SEQ ID NO 33
<211> LENGTH: 564
<212> TYPE: PRT
<213> ORGANISM: Aspergillus niger

<400> SEQUENCE: 33

Met Lys Gly Met Leu Pro Thr Leu Ser Trp Leu Ala Leu Gly Met Ala
1               5                   10                  15

Ser Leu Ala Thr Cys Thr Asn Pro Val Ala Gln Thr Lys Asn Gly Ser
            20                  25                  30

Tyr Tyr Gly Val Tyr Met Pro Gln Tyr Asn Glu Asp Tyr Phe Leu Gly
        35                  40                  45

Ile Pro Phe Ala Lys Pro Leu Ala His Leu Arg Trp Ala Asn Pro
    50                  55                  60

Glu Ser Leu Asn Glu Ser Trp Ser Gly Leu Arg Pro Ala Thr Gly Tyr
65                  70                  75                  80

Ala Met Glu Cys Ile Gly Tyr Gly Ser Asp Gln Lys Gly Tyr Leu Gln
                85                  90                  95

Ser Glu Asp Cys Leu Tyr Leu Asn Val Val Arg Pro Ala Glu Tyr Asp
            100                 105                 110

Asn Ala Ser Leu Pro Val Leu Val Trp Ile His Gly Gly Phe Ala
        115                 120                 125

Gln Gly Gly Thr Pro Asp Leu Arg Tyr Asn Leu Thr Phe Ile Val Glu
    130                 135                 140

His Ser Val Asn Ile Gly Gln Pro Ile Ile Ala Val Ser Val Ala Tyr
145                 150                 155                 160

Arg Leu Gly Pro Trp Gly Phe Phe Asn Gly Val Glu Leu Ala Asn Glu
                165                 170                 175

Gly Ser Leu Asn Leu Gly Leu Lys Asp Gln Arg Leu Ala Leu His Trp
            180                 185                 190
```

Val Lys Glu Asn Ile Ala Gly Phe Gly Gly Asp Pro Ser Lys Val Val
            195                 200                 205

Ile Tyr Gly Gln Ser Ala Gly Ser Glu Ser Val Gly Tyr Gln Ile Arg
        210                 215                 220

Ala Tyr Asn Gly Arg Asp Asp Gly Leu Phe Arg Gly Gly Met Met Glu
225                 230                 235                 240

Ser Gly Ala Val Leu Pro Gly Ser Ala Leu Asn Leu Thr Trp Thr Tyr
                245                 250                 255

Glu Pro Trp Phe Gln Gln Ile Ala Asp Glu Ala Gly Cys Ser Gln Thr
            260                 265                 270

Thr Arg Lys Leu Asp Cys Leu Arg Thr Pro Phe Thr Val Leu Asn
        275                 280                 285

Asn Ile Leu Asn Thr Thr Ala Asn Asp Thr Thr Pro Tyr Asn Trp Arg
290                 295                 300

Pro Thr Val Asp Gly Asp Phe Val Ala Arg Tyr Pro Ser Glu Gln Leu
305                 310                 315                 320

Asp Thr Gly Asp Phe Val Lys Val Pro Ile Ile Gly Tyr Thr Thr
            325                 330                 335

Asp Glu Gly Thr Thr Glu Cys Pro Glu Pro Val Asn Thr Thr Ala Glu
            340                 345                 350

Leu Lys Glu Tyr Leu Ser Ser Thr Thr Thr Tyr Gly Trp Ala Leu Asp
        355                 360                 365

Ser Gln Val Val Ser Ser Leu Leu Asp Leu Tyr Pro Asn Thr Thr Ser
370                 375                 380

Phe Gly Ile Pro Ser Ser Glu Glu Leu Gly Gly Asn Val Thr Phe Pro
385                 390                 395                 400

Gln Pro Tyr Gly Ala Ala Phe Arg Gln Thr Ala Ala Tyr Tyr Gly Asp
            405                 410                 415

Ala Gln Phe Ile Ala Ala Thr Arg Tyr Thr Cys Glu Leu Trp Ala Ala
                420                 425                 430

His Asn Leu Thr Ala Tyr Cys Tyr Arg Phe Asn Thr Lys Thr Asp Asp
        435                 440                 445

Tyr Asn Arg Glu Glu Gly Val Ala His Phe Ser Asp Val Ile Phe Ile
450                 455                 460

Phe Asn Asn Leu Asn Gly Tyr Gly Phe Ser Pro Asn Pro Phe Thr Asn
465                 470                 475                 480

Ala Pro Glu Ser Tyr Thr Glu Leu Ser Tyr Leu Met Ser Gly Ser Trp
            485                 490                 495

Ile Ser Phe Thr Asn Ser Leu Asp Pro Asn Lys Trp Thr Gly Arg Gly
                500                 505                 510

Arg Asn Ala Thr Lys Thr Glu Asn Trp Pro Val Tyr Asp Leu Glu Asn
        515                 520                 525

Pro Leu Ser Met Ile Trp Asp Ala Asn Val Thr Ser Tyr Ala Ala Pro
530                 535                 540

Asp Thr Trp Arg Lys Glu Gly Ile Ala Leu Ile Asn Ala Asn Arg Arg
545                 550                 555                 560

Ala Tyr Gln Arg

<210> SEQ ID NO 34
<211> LENGTH: 2371
<212> TYPE: DNA
<213> ORGANISM: Aspergillus niger

<400> SEQUENCE: 34
gccctgacat ggacggtgtc agatagagac cgttggaagg ctgaaccaca gggcacacgg      60

```
cacgttgagg accctgcatg ccggtgtatc cggataatgg cagataatcc cggctaattg      120
ggggcgacgg cagctacggc tcacaaattg tgatggaata gacacggcat gatgtttcaa      180
tgaagctcca aactttacag tgctaggctg taaacgtgat tataatcacg atgtaattga      240
ttatcatcta caactcaacc cccgcaccaa gaaatgaatc ctctcgtcgg aagaaaaaga      300
cggcattcca gaagaacttt ttcctagata acaaacagta atcagtccat ccgtccctga      360 cgatccccc atcgaacctc ggtaagacgc tcgacccaaa aaccagaccg acaagctttt       420
caacctccct aaacgaaaca acggctgtgt tgatcgtgaa cgtggttgcc tataccaata      480
cgagaaccat ataggataga aattgagttt accgtggaaa agccaccgc tacagtttaa       540 ttaaccaacc cacccacatg cccaaggcac ctgtaacagg gactactgtc cagagagtgg      600
atagtggcta gtgggcagac gtcggatgaa ctccggaaga ccctaactga tacgtagaac      660
catcgtgaac cctggtttgt ccctagttcg gggcgctatt cccagcgtag aaaagcggcc      720
gatcctctga aacagttttc ccccgggta tacttgctag ttagtcacta tcatacaaaa       780
gtagtgtagt ggacaagacc agggtctact actattagtt agttctgttt catcccgact      840
caattttgcg tcccaagacc ctgggttgtc cgggcctgtc ttgcccaaca cgagatgtat      900
ggagtaagta tggagggaga ctaacctcgg aatattcttg tctctttta gtactatcta       960 gcccttagtg agactatagc agtagtgaac cagagagaga gagagatgtc tatataagta     1020
cagtcgtaga tccctaaaca tgaccagctt cagactcaga ctcgagcagc cagtgcagtc     1080
cagtccactc tttcattctc acccttctt tactatctta caataatttc tattcaataa      1140
gtctgcagtg cagcacccac acacattcat tctctgagag ataaaaaata acaaaatggc     1200
ccccctcaaa tccctcctcc tcggcgcctc cctggccacc ctcgcccttt ccaccccact     1260
ggcaaccgac gccgaaaacc tctacgcacg tcaattcggc acgggctcta cagccaacga     1320
actcgagcag ggaagctgca aggatgtgac tctcatcttt gcgaggggt caactgagct      1380 tgggaatatg gtatgcttgt tgcctgcctt tacccgtact atactatccc agaacatacc     1440
aagcacaaca tcacaaaaca tgtggagcca ggagctaatc agtggtggtg atgatatgat     1500
gtagggcacc gtaatcggcc cccctctctg cgacaacctg aaatccaaac tcggatccga     1560
caaagtcgcc tgccagggtg tcggcggcca atacagcgcc ggactcgtgc agaatgccct     1620
gccccagaac accgatccgg ggagtatctc cgccgcgaag cagatgttcg aggaggcgaa     1680
ttcgaagtgt cccaatacta agattgttgc gggtggttat aggtatatat ccctttcccc     1740
tttaccttcc cccatatcaa tgctagaggc aaaggaatat catgctaatg tagatgttgg     1800
ggaaacagtc aaggaagcgc tgtgattgac aacgccgtgc aagaactcag caccaccgtg     1860
aaagaccaag tgaagggtgt cgtgctcttc gggttcacga gaaacgtgca ggatcacggg     1920
cagatcccta attaccctaa ggatgacgtg aaggtttatt gtgccgtggg cgatctggtc     1980
tgtgatgata cgttggttgt tacggcgatg catctgacgt atggcatgga tgcgggtgat     2040
gcggcgagct ttttggccga gaaggtgcag tcttccagta gttcgactac tagctccagc     2100
tcggatgccg cgagtagttc atctgctgcg gggacgtcgt cgtcggggtt gtcgggactg     2160
tcttcttttt ttggaggtct ctaaatagaa ttagatgaga tgagtggtcc gggtgggggt     2220
ttaggggatt gttgttcgtt tctcttggat gatttagttt ccgttattta cttagctggg     2280
ataagatata tggtacatag tatagatgtg ttgtgatgtt attctggcta ttttgtacac     2340
tttgacatga tctgcgatat gggagcgtct a                                    2371
```

<210> SEQ ID NO 35
<211> LENGTH: 789
<212> TYPE: DNA
<213> ORGANISM: Aspergillus niger
<220> FEATURE:
<221> NAME/KEY: CDS
<222> LOCATION: (1)..(789)

<400> SEQUENCE: 35

| | | | | | | | | | | | | | | | | |
|---|---|---|---|---|---|---|---|---|---|---|---|---|---|---|---|---|
| atg | gcc | ccc | ctc | aaa | tcc | ctc | ctc | ctc | ggc | gcc | tcc | ctg | gcc | acc | ctc | 48 |
| Met | Ala | Pro | Leu | Lys | Ser | Leu | Leu | Leu | Gly | Ala | Ser | Leu | Ala | Thr | Leu | |
| 1 | | | | 5 | | | | | 10 | | | | | 15 | | |
| gcc | ctt | tcc | acc | cca | ctg | gca | acc | gac | gcc | gaa | aac | ctc | tac | gca | cgt | 96 |
| Ala | Leu | Ser | Thr | Pro | Leu | Ala | Thr | Asp | Ala | Glu | Asn | Leu | Tyr | Ala | Arg | |
| | | | 20 | | | | | 25 | | | | | 30 | | | |
| caa | ttc | ggc | acg | ggc | tct | aca | gcc | aac | gaa | ctc | gag | cag | gga | agc | tgc | 144 |
| Gln | Phe | Gly | Thr | Gly | Ser | Thr | Ala | Asn | Glu | Leu | Glu | Gln | Gly | Ser | Cys | |
| | | 35 | | | | | 40 | | | | | 45 | | | | |
| aag | gat | gtg | act | ctc | atc | ttt | gcg | agg | ggg | tca | act | gag | ctt | ggg | aat | 192 |
| Lys | Asp | Val | Thr | Leu | Ile | Phe | Ala | Arg | Gly | Ser | Thr | Glu | Leu | Gly | Asn | |
| | 50 | | | | | 55 | | | | | 60 | | | | | |
| atg | ggc | acc | gta | atc | ggc | ccc | cct | ctc | tgc | gac | aac | ctg | aaa | tcc | aaa | 240 |
| Met | Gly | Thr | Val | Ile | Gly | Pro | Pro | Leu | Cys | Asp | Asn | Leu | Lys | Ser | Lys | |
| 65 | | | | | 70 | | | | | 75 | | | | | 80 | |
| ctc | gga | tcc | gac | aaa | gtc | gcc | tgc | cag | ggt | gtc | ggc | ggc | caa | tac | agc | 288 |
| Leu | Gly | Ser | Asp | Lys | Val | Ala | Cys | Gln | Gly | Val | Gly | Gly | Gln | Tyr | Ser | |
| | | | | 85 | | | | | 90 | | | | | 95 | | |
| gcc | gga | ctc | gtg | cag | aat | gcc | ctg | ccc | cag | aac | acc | gat | ccg | ggg | agt | 336 |
| Ala | Gly | Leu | Val | Gln | Asn | Ala | Leu | Pro | Gln | Asn | Thr | Asp | Pro | Gly | Ser | |
| | | | 100 | | | | | 105 | | | | | 110 | | | |
| atc | tcc | gcc | gcg | aag | cag | atg | ttc | gag | gag | gcg | aat | tcg | aag | tgt | ccc | 384 |
| Ile | Ser | Ala | Ala | Lys | Gln | Met | Phe | Glu | Glu | Ala | Asn | Ser | Lys | Cys | Pro | |
| | | 115 | | | | | 120 | | | | | 125 | | | | |
| aat | act | aag | att | gtt | gcg | ggt | ggt | tat | agt | caa | gga | agc | gct | gtg | att | 432 |
| Asn | Thr | Lys | Ile | Val | Ala | Gly | Gly | Tyr | Ser | Gln | Gly | Ser | Ala | Val | Ile | |
| | 130 | | | | | 135 | | | | | 140 | | | | | |
| gac | aac | gcc | gtg | caa | gaa | ctc | agc | acc | acc | gtg | aaa | gac | caa | gtg | aag | 480 |
| Asp | Asn | Ala | Val | Gln | Glu | Leu | Ser | Thr | Thr | Val | Lys | Asp | Gln | Val | Lys | |
| 145 | | | | | 150 | | | | | 155 | | | | | 160 | |
| ggt | gtc | gtg | ctc | ttc | ggg | ttc | acg | aga | aac | gtg | cag | gat | cac | ggg | cag | 528 |
| Gly | Val | Val | Leu | Phe | Gly | Phe | Thr | Arg | Asn | Val | Gln | Asp | His | Gly | Gln | |
| | | | | 165 | | | | | 170 | | | | | 175 | | |
| atc | cct | aat | tac | cct | aag | gat | gac | gtg | aag | gtt | tat | tgt | gcc | gtg | ggc | 576 |
| Ile | Pro | Asn | Tyr | Pro | Lys | Asp | Asp | Val | Lys | Val | Tyr | Cys | Ala | Val | Gly | |
| | | | 180 | | | | | 185 | | | | | 190 | | | |
| gat | ctg | gtc | tgt | gat | gat | acg | ttg | gtt | gtt | acg | gcg | atg | cat | ctg | acg | 624 |
| Asp | Leu | Val | Cys | Asp | Asp | Thr | Leu | Val | Val | Thr | Ala | Met | His | Leu | Thr | |
| | | 195 | | | | | 200 | | | | | 205 | | | | |
| tat | ggc | atg | gat | gcg | ggt | gat | gcg | gcg | agc | ttt | ttg | gcc | gag | aag | gtg | 672 |
| Tyr | Gly | Met | Asp | Ala | Gly | Asp | Ala | Ala | Ser | Phe | Leu | Ala | Glu | Lys | Val | |
| | 210 | | | | | 215 | | | | | 220 | | | | | |
| cag | tct | tcc | agt | agt | tcg | act | act | agc | tcc | agc | tcg | gat | gcc | gcg | agt | 720 |
| Gln | Ser | Ser | Ser | Ser | Ser | Thr | Thr | Ser | Ser | Ser | Ser | Asp | Ala | Ala | Ser | |
| 225 | | | | | 230 | | | | | 235 | | | | | 240 | |
| agt | tca | tct | gct | gcg | ggg | acg | tcg | tcg | ggg | ttg | tcg | gga | ctg | tct | | 768 |
| Ser | Ser | Ser | Ala | Ala | Gly | Thr | Ser | Ser | Gly | Leu | Ser | Gly | Leu | Ser | | |
| | | | | 245 | | | | | 250 | | | | | 255 | | |
| tct | ttt | ttt | gga | ggt | ctc | taa | | | | | | | | | | 789 |
| Ser | Phe | Phe | Gly | Gly | Leu | | | | | | | | | | | |
| | | | 260 | | | | | | | | | | | | | |

<210> SEQ ID NO 36

```
<211> LENGTH: 262
<212> TYPE: PRT
<213> ORGANISM: Aspergillus niger

<400> SEQUENCE: 36

Met Ala Pro Leu Lys Ser Leu Leu Gly Ala Ser Leu Ala Thr Leu
1               5                   10                  15

Ala Leu Ser Thr Pro Leu Ala Thr Asp Ala Glu Asn Leu Tyr Ala Arg
            20                  25                  30

Gln Phe Gly Thr Gly Ser Thr Ala Asn Glu Leu Glu Gln Gly Ser Cys
                35                  40                  45

Lys Asp Val Thr Leu Ile Phe Ala Arg Gly Ser Thr Glu Leu Gly Asn
50                  55                  60

Met Gly Thr Val Ile Gly Pro Pro Leu Cys Asp Asn Leu Lys Ser Lys
65                  70                  75                  80

Leu Gly Ser Asp Lys Val Ala Cys Gln Gly Val Gly Gly Tyr Ser
                85                  90                  95

Ala Gly Leu Val Gln Asn Ala Leu Pro Gln Asn Thr Asp Pro Gly Ser
                100                 105                 110

Ile Ser Ala Ala Lys Gln Met Phe Glu Glu Ala Asn Ser Lys Cys Pro
            115                 120                 125

Asn Thr Lys Ile Val Ala Gly Gly Tyr Ser Gln Gly Ser Ala Val Ile
130                 135                 140

Asp Asn Ala Val Gln Glu Leu Ser Thr Thr Val Lys Asp Gln Val Lys
145                 150                 155                 160

Gly Val Val Leu Phe Gly Phe Thr Arg Asn Val Gln Asp His Gly Gln
                165                 170                 175

Ile Pro Asn Tyr Pro Lys Asp Asp Val Lys Val Tyr Cys Ala Val Gly
                180                 185                 190

Asp Leu Val Cys Asp Asp Thr Leu Val Val Thr Ala Met His Leu Thr
            195                 200                 205

Tyr Gly Met Asp Ala Gly Asp Ala Ala Ser Phe Leu Ala Glu Lys Val
        210                 215                 220

Gln Ser Ser Ser Ser Ser Thr Thr Ser Ser Ser Ser Asp Ala Ala Ser
225                 230                 235                 240

Ser Ser Ser Ala Ala Gly Thr Ser Ser Ser Gly Leu Ser Gly Leu Ser
                245                 250                 255

Ser Phe Phe Gly Gly Leu
            260

<210> SEQ ID NO 37
<211> LENGTH: 2981
<212> TYPE: DNA
<213> ORGANISM: Aspergillus niger

<400> SEQUENCE: 37
tcctcatccc atgctctccc ggcagaaccc cggagacaac ccacactaat gcacccaaag       60
caaaatgaca tggattgaat tatccggggt gcatccatct tgttccccca cacattggac      120
cctttcctta taatggctgc cccggcaaac ccccaattgc tgtttaggcc agcgcagata      180
gcaaatctct cgtctgatta acgatgctaa agctcgctgt tgctcttttt tcgttacttg      240
ccgtgggcaa tgcagcgcca accaaagtgg cccgttccac ggccagtcct acggccaagg      300
ttcgcaacgg tacatatgtc ggagtgacaa atgcgcatta ccagcaagat ttcttttttgg     360 gaatgccgta tgcccagcag cctttaggtg acttgcgctt cacggtgcct cagtccctga      420
acgaaagctg gagtggcgag cgcgacgcga aggaatattc caatatctgt gtaggatacg      480
```

```
gtgtgagtgc gcaaatcttc ttcgagagcc aggccctact agctgcatcc tggcactatg    540
aatataatct aatgggtaga tctgttagac cgactcgatt tggtacccac agtccgaagc    600
ttgtctaacc ttgaatgtca tccgcgattc ttctgcaaat gagaactcga agctccccgt    660
gggcgtctgg atacatggag gtggcttctt tgagggatct agtgctgacc agcgctacaa    720
catgtccgcg attgttgcca actcctataa gatcggtatg tcgacgtatg cggttgtaga    780
attagactga ctcggcttgc tcgcattgta ggaaagccgt tcattgctgt cagcttaaac    840
tatcgccttt cggcatgggg cttcttgagt tccagtcaag tctggggcac tggcaatacc    900
aatctaggta tcagggatca aaggttagca ctccattgga tcaaggagaa tatcgcggca    960
ttcggaggag acccagataa gatcactatc tgggcgaat ctgccggagc gatgtccgtg    1020
ggttatcacc ttgcagcata cggcggtagg gacgatggac tcttccgtgg aggaattatg    1080
gagtcaggag ggactattgc agctagtcca gccaactata ccgggtacca agcgcactat    1140
gatgagctcg cgggtcaagt cggttgctcc gacgtagtag attcgttgca gtgcctgcgc    1200
gaagttccgt tcgagaaatt gaacgctgct ctcaacacca ccagtggtaa ctcggatttc    1260
aatttcgggc ccgtcattga tggagatata atcagggact ggggcagcct ccagctagac    1320
aagcatgaat tcgtcaaagt ccctattctt gcaggtacca ataccgacga agggacagcc    1380
tttgggccca caggtatcaa cacgacagag gagttctatg catatctcac aggtatgtgt    1440
gataatgagt taacatcctg aaagaacccc agagcagcaa acgggctaa tctcactggc    1500 agatggcgaa tctggattcc agctacccc cacgatcgcc caggaaatcc tgcagctcta    1560
ccctgatgat ccagcactgg gcatccccga atttctcggt gacactagag tcccgtccaa    1620
aggctaccaa tggcggcgca cctgtgcata cgcaggggac tatgtaatgc atgccaaccg    1680
tcgccgacaa tgtgaggcgt ggacagagac ctcgacgacg gcgtactgtt atcgattcaa    1740
tatgcgtgcg gccgatgtcc ccatcctgtc tggcgccacc cattttgaag aagttgcttt    1800
tgtattcaac aacattgcag gactcgggta ccattacgga aagccgttcg cagggatgcc    1860
cgagtcctac gtacagctaa gcaacttgat gaccagcatg tgggcatcct tcatccacga    1920
tttagaccct aattcgggca tcaaggactc agctgtacag tggcaaccgt acgggaagga    1980
tcagccggtt gatctagtgt ttgatgcgaa tgtcacgagc tacagctaca tggagccaga    2040
cacgtggcgg aaggagggga tcgactatat caattccgtg gccaacgcgt actggcgata    2100
agcttcatgc tatcgaaaac acatgtgatg agcgtgagag ttttttgcctt ccgcttgatg    2160 ttgcctgcga gaggaaaagg ttaaggcaaa caaggatggt aggggtgcg agcgcatcta    2220 agtcggccac ggtagttgat tgatggttcc ctcgttagaa gcaaatacag atgccatact    2280
tcctgcaaca aacccagaac ttgttgtaat caagttttt caaacggatg gtagatcggt    2340
tccgatttgt aaaagcaag atcctagcgt tacgagggaa ccaagacacc cacacagagg    2400
agcattacga attccaaatt accaaagcct gtataacaaa aaccagcaga gaccgcctaa    2460
ttagtcaact acagcattgg ttcaatgtac ctgcaaggac ctttacacgc gtggtcaccc    2520
atgtaccaag ccaagccaac ggccaagaca cggaaataac caagaggaaa ccactccctc    2580
caagaatcaa gaacccaggg ggtcaagaga atctggaagc gataaagggg tcttcttttt    2640
tttctttgct tacctagaga gggaggagtc ggcgttcatc gtcaatcagt agagtgttct    2700
ccgccctgag tggtgtagtc tatatccgga ccatcgggga catgattatc atacgatcca    2760
taaccaagtc cccgattgta ctacggctac caaaactaga atgatgaaaa tattggagta    2820
cgaaaggaac taaaccaata ctaagaaaaa aaaaaagag taaagaaaaa agagtaaaaa    2880
```

```
accaagctcg gaaagtaaaa atttcccctg gtcttgttgt cattccccta cctattgaga    2940
accgggttca ccaatgacag cggatccccg atttgacatc g                       2981
```

<210> SEQ ID NO 38
<211> LENGTH: 1686
<212> TYPE: DNA
<213> ORGANISM: Aspergillus niger
<220> FEATURE:
<221> NAME/KEY: CDS
<222> LOCATION: (1)..(1686)

<400> SEQUENCE: 38

```
atg cta aag ctc gct gtt gct ctt ttt tcg tta ctt gcc gtg ggc aat      48
Met Leu Lys Leu Ala Val Ala Leu Phe Ser Leu Leu Ala Val Gly Asn
1               5                   10                  15 gca gcg cca acc aaa gtg gcc cgt tcc acg gcc agt cct acg gcc aag      96
Ala Ala Pro Thr Lys Val Ala Arg Ser Thr Ala Ser Pro Thr Ala Lys
                20                  25                  30 gtt cgc aac ggt aca tat gtc gga gtg aca aat gcg cat tac cag caa     144
Val Arg Asn Gly Thr Tyr Val Gly Val Thr Asn Ala His Tyr Gln Gln
            35                  40                  45 gat ttc ttt ttg gga atg ccg tat gcc cag cag cct tta ggt gac ttg     192
Asp Phe Phe Leu Gly Met Pro Tyr Ala Gln Gln Pro Leu Gly Asp Leu
        50                  55                  60 cgc ttc acg gtg cct cag tcc ctg aac gaa agc tgg agt ggc gag cgc     240
Arg Phe Thr Val Pro Gln Ser Leu Asn Glu Ser Trp Ser Gly Glu Arg
65                  70                  75                  80 gac gcg aag gaa tat tcc aat atc tgt gta gga tac ggt acc gac tcg     288
Asp Ala Lys Glu Tyr Ser Asn Ile Cys Val Gly Tyr Gly Thr Asp Ser
                85                  90                  95 att tgg tac cca cag tcc gaa gct tgt cta acc ttg aat gtc atc cgc     336
Ile Trp Tyr Pro Gln Ser Glu Ala Cys Leu Thr Leu Asn Val Ile Arg
            100                 105                 110 gat tct tct gca aat gag aac tcg aag ctc ccc gtg ggc gtc tgg ata     384
Asp Ser Ser Ala Asn Glu Asn Ser Lys Leu Pro Val Gly Val Trp Ile
        115                 120                 125 cat gga ggt ggc ttc ttt gag gga tct agt gct gac cag cgc tac aac     432
His Gly Gly Gly Phe Phe Glu Gly Ser Ser Ala Asp Gln Arg Tyr Asn
    130                 135                 140 atg tcc gcg att gtt gcc aac tcc tat aag atc gga aag ccg ttc att     480
Met Ser Ala Ile Val Ala Asn Ser Tyr Lys Ile Gly Lys Pro Phe Ile
145                 150                 155                 160 gct gtc agc tta aac tat cgc ctt tcg gca tgg ggc ttc ttg agt tcc     528
Ala Val Ser Leu Asn Tyr Arg Leu Ser Ala Trp Gly Phe Leu Ser Ser
                165                 170                 175 agt caa gtc tgg ggc act ggc aat acc aat cta ggt atc agg gat caa     576
Ser Gln Val Trp Gly Thr Gly Asn Thr Asn Leu Gly Ile Arg Asp Gln
            180                 185                 190 agg tta gca ctc cat tgg atc aag gag aat atc gcg gca ttc gga gga     624
Arg Leu Ala Leu His Trp Ile Lys Glu Asn Ile Ala Ala Phe Gly Gly
        195                 200                 205 gac cca gat aag atc act atc tgg ggc gaa tct gcc gga gcg atg tcc     672
Asp Pro Asp Lys Ile Thr Ile Trp Gly Glu Ser Ala Gly Ala Met Ser
    210                 215                 220 gtg ggt tat cac ctt gca gca tac ggc ggt agg gac gat gga ctc ttc     720
Val Gly Tyr His Leu Ala Ala Tyr Gly Gly Arg Asp Asp Gly Leu Phe
225                 230                 235                 240 cgt gga gga att atg gag tca gga ggg act att gca gct agt cca gcc     768
Arg Gly Gly Ile Met Glu Ser Gly Gly Thr Ile Ala Ala Ser Pro Ala
                245                 250                 255
```

```
aac tat acc ggg tac caa gcg cac tat gat gag ctc gcg ggt caa gtc        816
Asn Tyr Thr Gly Tyr Gln Ala His Tyr Asp Glu Leu Ala Gly Gln Val
            260                 265                 270 ggt tgc tcc gac gta gta gat tcg ttg cag tgc ctg cgc gaa gtt ccg        864
Gly Cys Ser Asp Val Val Asp Ser Leu Gln Cys Leu Arg Glu Val Pro
        275                 280                 285 ttc gag aaa ttg aac gct gct ctc aac acc acc agt ggt aac tcg gat        912
Phe Glu Lys Leu Asn Ala Ala Leu Asn Thr Thr Ser Gly Asn Ser Asp
    290                 295                 300 ttc aat ttc ggg ccc gtc att gat gga gat ata atc agg gac tgg ggc        960
Phe Asn Phe Gly Pro Val Ile Asp Gly Asp Ile Ile Arg Asp Trp Gly
305                 310                 315                 320 agc ctc cag cta gac aag cat gaa ttc gtc aaa gtc cct att ctt gca       1008
Ser Leu Gln Leu Asp Lys His Glu Phe Val Lys Val Pro Ile Leu Ala
                325                 330                 335 ggt acc aat acc gac gaa ggg aca gcc ttt ggg ccc aca ggt atc aac       1056
Gly Thr Asn Thr Asp Glu Gly Thr Ala Phe Gly Pro Thr Gly Ile Asn
            340                 345                 350 acg aca gag gag ttc tat gca tat ctc aca gat ggc gaa tct gga ttc       1104
Thr Thr Glu Glu Phe Tyr Ala Tyr Leu Thr Asp Gly Glu Ser Gly Phe
        355                 360                 365 cag cta ccc ccc acg atc gcc cag gaa atc ctg cag ctc tac cct gat       1152
Gln Leu Pro Pro Thr Ile Ala Gln Glu Ile Leu Gln Leu Tyr Pro Asp
    370                 375                 380 gat cca gca ctg ggc atc ccc gaa ttt ctc ggt gac act aga gtc ccg       1200
Asp Pro Ala Leu Gly Ile Pro Glu Phe Leu Gly Asp Thr Arg Val Pro
385                 390                 395                 400 tcc aaa ggc tac caa tgg cgg cgc acc tgt gca tac gca ggg gac tat       1248
Ser Lys Gly Tyr Gln Trp Arg Arg Thr Cys Ala Tyr Ala Gly Asp Tyr
                405                 410                 415 gta atg cat gcc aac cgt cgc cga caa tgt gag gcg tgg aca gag acc       1296
Val Met His Ala Asn Arg Arg Arg Gln Cys Glu Ala Trp Thr Glu Thr
            420                 425                 430 tcg acg acg gcg tac tgt tat cga ttc aat atg cgt gcg gcc gat gtc       1344
Ser Thr Thr Ala Tyr Cys Tyr Arg Phe Asn Met Arg Ala Ala Asp Val
        435                 440                 445 ccc atc ctg tct ggc gcc acc cat ttt gaa gaa gtt gct ttt gta ttc       1392
Pro Ile Leu Ser Gly Ala Thr His Phe Glu Glu Val Ala Phe Val Phe
    450                 455                 460 aac aac att gca gga ctc ggg tac cat tac gga aag ccg ttc gca ggg       1440
Asn Asn Ile Ala Gly Leu Gly Tyr His Tyr Gly Lys Pro Phe Ala Gly
465                 470                 475                 480 atg ccc gag tcc tac gta cag cta agc aac ttg atg acc agc atg tgg       1488
Met Pro Glu Ser Tyr Val Gln Leu Ser Asn Leu Met Thr Ser Met Trp
                485                 490                 495 gca tcc ttc atc cac gat tta gac cct aat tcg ggc atc aag gac tca       1536
Ala Ser Phe Ile His Asp Leu Asp Pro Asn Ser Gly Ile Lys Asp Ser
            500                 505                 510 gct gta cag tgg caa ccg tac ggg aag gat cag ccg gtt gat cta gtg       1584
Ala Val Gln Trp Gln Pro Tyr Gly Lys Asp Gln Pro Val Asp Leu Val
        515                 520                 525 ttt gat gcg aat gtc acg agc tac agc tac atg gag cca gac acg tgg       1632
Phe Asp Ala Asn Val Thr Ser Tyr Ser Tyr Met Glu Pro Asp Thr Trp
    530                 535                 540 cgg aag gag ggg atc gac tat atc aat tcc gtg gcc aac gcg tac tgg       1680
Arg Lys Glu Gly Ile Asp Tyr Ile Asn Ser Val Ala Asn Ala Tyr Trp
545                 550                 555                 560 cga taa                                                                1686
Arg
```

<210> SEQ ID NO 39
<211> LENGTH: 561
<212> TYPE: PRT
<213> ORGANISM: Aspergillus niger

<400> SEQUENCE: 39

```
Met Leu Lys Leu Ala Val Ala Leu Phe Ser Leu Leu Ala Val Gly Asn
1               5                   10                  15

Ala Ala Pro Thr Lys Val Ala Arg Ser Thr Ala Ser Pro Thr Ala Lys
            20                  25                  30

Val Arg Asn Gly Thr Tyr Val Gly Val Thr Asn Ala His Tyr Gln Gln
        35                  40                  45

Asp Phe Phe Leu Gly Met Pro Tyr Ala Gln Gln Pro Leu Gly Asp Leu
    50                  55                  60

Arg Phe Thr Val Pro Gln Ser Leu Asn Glu Ser Trp Ser Gly Glu Arg
65                  70                  75                  80

Asp Ala Lys Glu Tyr Ser Asn Ile Cys Val Gly Tyr Gly Thr Asp Ser
                85                  90                  95

Ile Trp Tyr Pro Gln Ser Glu Ala Cys Leu Thr Leu Asn Val Ile Arg
            100                 105                 110

Asp Ser Ser Ala Asn Glu Asn Ser Lys Leu Pro Val Gly Val Trp Ile
        115                 120                 125

His Gly Gly Gly Phe Phe Glu Gly Ser Ser Ala Asp Gln Arg Tyr Asn
    130                 135                 140

Met Ser Ala Ile Val Ala Asn Ser Tyr Lys Ile Gly Lys Pro Phe Ile
145                 150                 155                 160

Ala Val Ser Leu Asn Tyr Arg Leu Ser Ala Trp Gly Phe Leu Ser Ser
                165                 170                 175

Ser Gln Val Trp Gly Thr Gly Asn Thr Asn Leu Gly Ile Arg Asp Gln
            180                 185                 190

Arg Leu Ala Leu His Trp Ile Lys Glu Asn Ile Ala Ala Phe Gly Gly
        195                 200                 205

Asp Pro Asp Lys Ile Thr Ile Trp Gly Glu Ser Ala Gly Ala Met Ser
    210                 215                 220

Val Gly Tyr His Leu Ala Ala Tyr Gly Gly Arg Asp Asp Gly Leu Phe
225                 230                 235                 240

Arg Gly Gly Ile Met Glu Ser Gly Gly Thr Ile Ala Ala Ser Pro Ala
                245                 250                 255

Asn Tyr Thr Gly Tyr Gln Ala His Tyr Asp Glu Leu Ala Gly Gln Val
            260                 265                 270

Gly Cys Ser Asp Val Val Asp Ser Leu Gln Cys Leu Arg Glu Val Pro
        275                 280                 285

Phe Glu Lys Leu Asn Ala Ala Leu Asn Thr Thr Ser Gly Asn Ser Asp
    290                 295                 300

Phe Asn Phe Gly Pro Val Ile Asp Gly Asp Ile Ile Arg Asp Trp Gly
305                 310                 315                 320

Ser Leu Gln Leu Asp Lys His Glu Phe Val Lys Val Pro Ile Leu Ala
                325                 330                 335

Gly Thr Asn Thr Asp Glu Gly Thr Ala Phe Gly Pro Thr Gly Ile Asn
            340                 345                 350

Thr Thr Glu Glu Phe Tyr Ala Tyr Leu Thr Asp Gly Glu Ser Gly Phe
        355                 360                 365

Gln Leu Pro Pro Thr Ile Ala Gln Glu Ile Leu Gln Leu Tyr Pro Asp
    370                 375                 380

Asp Pro Ala Leu Gly Ile Pro Glu Phe Leu Gly Asp Thr Arg Val Pro
```

-continued

```
385                 390                 395                 400
Ser Lys Gly Tyr Gln Trp Arg Arg Thr Cys Ala Tyr Ala Gly Asp Tyr
            405                 410                 415

Val Met His Ala Asn Arg Arg Gln Cys Glu Ala Trp Thr Glu Thr
            420                 425                 430

Ser Thr Thr Ala Tyr Cys Tyr Arg Phe Asn Met Arg Ala Ala Asp Val
        435                 440                 445

Pro Ile Leu Ser Gly Ala Thr His Phe Glu Glu Val Ala Phe Val Phe
        450                 455                 460

Asn Asn Ile Ala Gly Leu Gly Tyr His Tyr Gly Lys Pro Phe Ala Gly
465                 470                 475                 480

Met Pro Glu Ser Tyr Val Gln Leu Ser Asn Leu Met Thr Ser Met Trp
            485                 490                 495

Ala Ser Phe Ile His Asp Leu Asp Pro Asn Ser Gly Ile Lys Asp Ser
            500                 505                 510

Ala Val Gln Trp Gln Pro Tyr Gly Lys Asp Gln Pro Val Asp Leu Val
            515                 520                 525

Phe Asp Ala Asn Val Thr Ser Tyr Ser Tyr Met Glu Pro Asp Thr Trp
        530                 535                 540

Arg Lys Glu Gly Ile Asp Tyr Ile Asn Ser Val Ala Asn Ala Tyr Trp
545                 550                 555                 560

Arg
```

LIPASES AND USES THEREOF

This application is a divisional of application Ser. No. 10/524,983, filed Jun. 7, 2006, (issued as U.S. Pat. No. 7,550, 280); which is a U.S. national stage under 35 U.S.C. 371 of Int'l application No. PCT/EP2003/009145, filed Aug. 15,2003; the entire contents of which are incorporated by reference.

FIELD OF THE INVENTION

The invention relates to newly identified polynucleotide sequence comprising a gene that encodes a novel lipolytic enzyme from *Aspergillus niger*. The invention features the full length nucleotide sequence of the novel gene, the cDNA sequence comprising the full length coding sequence of the novel lipolytic enzyme as well as the amino acid sequence of the full-length lipolytic enzyme and functional equivalents thereof. The invention also relates to methods of using these enzymes in industrial processes and methods of diagnosing fungal infections. Also included in the invention are cells transformed with a polynucleotide according to the invention and cells wherein a lipolytic enzyme according to the invention is genetically modified to enhance its activity and/or level of expression.

BACKGROUND OF THE INVENTION

Baked products such as bread are prepared from a dough which is usually made from the basic ingredients (wheat) flour, water and optionally salt. Depending on the baked products, other ingredients added may be sugars, flavours etceteras. For leavened products, primarily baker's yeast is used next to chemical leavening systems such as a combination of an acid (generating compound) and bicarbonate.

In order to improve the handling properties of the dough and/or the final properties of the baked products there is a continuous effort to develop processing aids with improving properties. Processing aids are defined herein as compounds that improve the handling properties of the dough and/or the final properties of the baked products. Dough properties that may be improved comprise machineability, gas retaining capability, reduced stickiness, elasticity, extensibility, moldability etcetera. Properties of the baked products that may be improved comprise loaf volume, crust crispiness, crumb texture and softness, flavour relative staleness and shelf life. These dough and/or baked product improving processing aids can be divided into two groups: chemical additives and enzymes (also referred to as baking enzymes).

Yeast, enzymes and chemical additives are generally added separately to the dough. Yeast may be added as a liquid suspension, in a compressed form or as active dry (ADY) or instant dry yeast (IDY). The difference between these yeast formulations is the water- and yeast dry matter content. Liquid yeast has a yeast dry matter content of less than 25% (w/v). Cream yeast is a particular form of liquid yeast and has a dry matter content between 17 and 23% (w/v). Compressed yeast has a yeast dry matter content between 25-35% (w/v) while the dry yeast formulations have a yeast dry matter content between 92-98% (w/v).

Enzymes may be added in a dry, e.g. granulated form or in liquid form. The chemical additives are in most cases added in powder form. Also, processing aid compositions which are tailored to specific baking applications, may be composed of a dedicated mixture of chemical additives and enzyme.

The preparation of a dough from the ingredients and processing aids described above is well known in the art and comprises mixing of said ingredients and processing aids and one or more moulding and fermentation steps.

The preparation of baked products from such doughs is also well known in the art and may comprise molding and shaping and further fermentation of the dough followed by baking at required temperatures and baking times.

Chemical additives with improving properties comprise oxidising agents such as ascorbic acid, bromate and azodicarbonate, reducing agents such as L-cysteine and glutathione, emulsifiers acting as dough conditioners such as diacetyl tartaric esters of monoldiglycerides (DATEM), sodium stearoyl lactylate (SSL) or calcium stearoyl lactylate (CSL), or acting as crumb softeners such as glycerol monostearate (GMS) etceteras, fatty materials such as triglycerides (fat) or lecithin and others.

As a result of a consumer-driven need to replace the chemical additives by more natural products, several baking enzymes have been developed with dough and/or baked product improving properties and which are used in all possible combinations depending on the specific baking application conditions. Suitable enzymes include starch degrading enzymes, arabinoxylan- and other hemicellulose degrading enzymes, cellulose degrading enzymes, oxidizing enzymes, fatty material splitting enzymes, protein degrading, modifying or crosslinking-enzymes.

Starch degrading enzymes are for instance endo-acting enzymes such as alpha-amylase, maltogenic amylase, pullulanase or other debranching enzymes and exo-acting enzymes that cleave off glucose (amyloglucosidase), maltose (beta-amylase), maltotriose, maltotetraose and higher oligosaccharides.

Arabinoxylan- and other hemicellulose degrading enzymes are for instance xylanases, pentosanases, hemicellulase, arabinofuranosidase, glucanase and others.

Cellulose degrading enzymes are for instance cellulase, cellobiohydrolase and beta-glucosidase.

Oxidizing enzymes are for instance glucose oxidase, hexose oxidase, pyranose oxidase, sulfhydryl oxidase, lipoxygenase, laccase, polyphenol oxidases and others.

Fatty material splitting enzymes are for instance lipolytic enzymes such as triacylglycerol lipases, phospholipases (such as $A_1$, $A_2$, B, C and D) and galactolipases.

Protein degrading, modifying or crosslinking enzymes are for instance endo-acting proteases (serine proteases, metalloproteases, aspartyl proteases, thiol proteases), exo-acting peptidases that cleave off one amino acid, or dipeptide, tripeptide etceteras from the N-terminal (aminopeptidases) or C-terminal (carboxypeptidases) ends of the polypeptide chain, asparagines or glutamine deamidating enzymes such as deamidase and peptidoglutaminase or crosslinking enzymes such as transglutaminase.

Baking enzymes may conveniently be produced in microorganisms. Microbial baking enzymes are available from a variety of sources; *Bacillus* spec. are a common source of bacterial enzymes, whereas fungal enzymes are commonly produced in *Aspergillus* spec.

Baking enzymes may be used in a manifold of baked goods. The term "baked goods" is herein defined as to comprise bread products such as tin bread, loaves of bread, French bread as well as rolls, cakes, pies, muffins, yeast raised and cake doughnuts and the like.

In the above processes, it is advantageous to use baking enzymes that are obtained by recombinant DNA techniques. Such recombinant enzymes have a number of advantages over their traditionally purified counterparts. Recombinant enzymes may be produced at a low cost price, high yield, free from contaminating agents like bacteria or viruses but also free from bacterial toxins or contaminating other enzyme activities.

OBJECT OF THE INVENTION

It is an object of the invention to provide novel polynucleotides encoding novel lipolytic enzymes with improved properties. A further object is to provide naturally and recombinantly produced lipolytic enzymes as well as recombinant strains producing these. Also fusion polypeptides are part of the invention as well as methods of making and using the polynucleotides and polypeptides according to the invention.

It is also an object of the invention to provide novel lipolytic enzymes, which solve at least one of the above-mentioned problems or to provide novel lipolytic enzymes, which have one or more improved properties if used in dough and/or baked products, selected from the group of increased strength of the dough, increased elasticity of the dough, increased stability of the dough, reduced stickiness of the dough, improved extensibility of the dough, improved machineability of the dough, increased volume of the baked product, improved crumb structure of the baked product, improved softness of the baked product, improved flavour of the baked product, improved anti-staling of the baked product, improved colour of the baked product, improved crust of the baked product or which have a broad substrate specificity.

SUMMARY OF THE INVENTION

The invention provides for novel polynucleotides encoding novel lipolytic enzymes. More in particular, the invention provides for polynucleotides having a nucleotide sequence that hybridises preferably under highly stringent conditions to a sequence selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38. Consequently, the invention provides nucleic acids that are more than 40% such as about 60%, preferably 65%, more preferably 70%, even more preferably 75%, 80%, 85%, 90%, 95%, 96%, 97%, 98% or 99% homologous to the sequences selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38.

In a more preferred embodiment the invention provides for such an isolated polynucleotide obtainable from a filamentous fungus, in particular *Aspergillus niger* is preferred.

In one embodiment, the invention provides for an isolated polynucleotide comprising a nucleic acid sequence encoding a polypeptide with an amino acid sequence selected from the group consisting of SEQ ID NO: 3, 6, 9, 12, 15, 18, 21, 24, 27, 30, 33, 36 and 39 or functional equivalents thereof.

In a further preferred embodiment, the invention provides an isolated polynucleotide encoding at least one functional domain of a polypeptide selected from the group consisting of SEQ ID NO: 3, 6, 9, 12, 15, 18, 21, 24, 27, 30, 33, 36 and 39 or functional equivalents thereof.

In a preferred embodiment the invention provides a lipolytic enzyme gene selected from the group consisting of SEQ ID NO: 1, 4, 7, 10, 13, 16, 19, 22, 25, 28, 31, 34 and 37. In another aspect the invention provides a polynucleotide, preferably a cDNA encoding an *Aspergillus niger* lipolytic enzyme whose amino acid sequence is selected from the group consisting of SEQ ID NO: 3, 6, 9, 12, 15, 18, 21, 24, 27, 30, 33, 36 and 39 or variants or fragments of that polypeptide. In a preferred embodiment the cDNA has a sequence selected from the group consisting of SEQ ID NO: 2, 5, 8, 11, 14, 17, 20, 23, 26, 29, 32, 35 and 38 or functional equivalents thereof.

In an even further preferred embodiment, the invention provides for a polynucleotide comprising the coding sequence of the polynucleotides according to the invention, preferred is the polynucleotide sequence selected from the group consisting of SEQ ID NO: 2, 5, 8, 11, 14, 17, 20, 23, 26, 29, 32, 35 and 38.

The invention also relates to vectors comprising a polynucleotide sequence according to the invention and primers, probes and fragments that may be used to amplify or detect the DNA according to the invention.

In a further preferred embodiment, a vector is provided wherein the polynucleotide sequence according to the invention is functionally linked with regulatory sequences suitable for expression of the encoded amino acid sequence in a suitable host cell, such as *Aspergillus niger* or *Aspergillus oryzae*. The invention also provides methods for preparing polynucleotides and vectors according to the invention.

The invention also relates to recombinantly produced host cells that contain heterologous or homologous polynucleotides according to the invention.

In another embodiment, the invention provides recombinant host cells wherein the expression of a lipolytic enzyme according to the invention is significantly increased or wherein the activity of the lipolytic enzyme is increased.

In another embodiment the invention provides for a recombinantly produced host cell that contains heterologous or homologous polynucleotide according to the invention and wherein the cell is capable of producing a functional lipolytic enzyme according to the invention, preferably a cell capable of over-expressing the lipolytic enzyme according to the invention, for example an *Aspergillus* strain comprising an increased copy number of a gene or cDNA according to the invention.

In yet another aspect of the invention, a purified polypeptide is provided. The polypeptides according to the invention include the polypeptides encoded by the polynucleotides according to the invention. Especially preferred is a polypeptide selected from the group consisting of SEQ ID NO: 3, 6, 9, 12, 15, 18, 21, 24, 27, 30, 33, 36 and 39 or functional equivalents thereof.

Accordingly, in one aspect the present invention provides a lipolytic enzyme composition containing as an active ingredient an enzyme selected from the group consisting of SEQ ID NO: 3, 6, 9, 12, 15, 18, 21, 24, 27, 30, 33, 36 and 39 or functional equivalents thereof.

In another aspect, the invention provides a method of making baked goods wherein there is incorporated into the dough used for making the baked goods one or more enzymes selected from the group consisting of SEQ ID NO: 3, 6, 9, 12, 15, 18, 21, 24, 27, 30, 33, 36 and 39 or functional equivalents thereof.

Fusion proteins comprising a polypeptide according to the invention are also within the scope of the invention. The invention also provides methods of making the polypeptides according to the invention.

The invention also relates to the use of the lipolytic enzyme according to the invention in any industrial process as described herein.

DETAILED DESCRIPTION OF THE INVENTION

A lipolytic enzyme is defined herein as an enzyme exhibiting at least one and preferably two or three or four or more of the following lipolytic activities: triacylglycerol lipase, phospholipase A₁, phospholipase A₂, phospholipase B, phospholipase C, phospholipase D, lysophospholipase and galactolipase.

Polynucleotides

The present invention provides polynucleotides encoding lipolytic enzymes having an amino acid sequence selected from the group consisting of SEQ ID NO: 3, 6, 9, 12, 15, 18, 21, 24, 27, 30, 33, 36 and 39 or functional equivalents thereof. The sequences of the seven genes encoding the lipolytic enzymes NBE028, NBE029, NBE030, NBE031, NBE032, NBE033, NBE034, NBE036, NBE038, NBE039, NBE043, NBE045 and NBE042 respectively were determined by sequencing genomic clones obtained from *Aspergillus niger*. The invention provides polynucleotide sequences comprising the genes encoding the lipolytic enzymes NBE028, NBE029, NBE030, NBE031, NBE032, NBE033, NBE034, NBE036, NBE038, NBE039, NBE043, NBE045 and NBE042 as well as their complete cDNA sequences and their coding sequences (Table 1). Accordingly, the invention relates to isolated polynucleotides comprising the nucleotide sequences selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38 or functional equivalents thereof.

TABLE 1

| lipolytic enzyme | Sequence (SEQ ID NO) | | |
|---|---|---|---|
| NBE xxx | genomic | cDNA | amino acid |
| NBE028 | 1 | 2 | 3 |
| NBB029 | 4 | 5 | 6 |
| NBE030 | 7 | 8 | 9 |
| NBE031 | 10 | 11 | 12 |
| NBE032 | 13 | 14 | 15 |
| NBE033 | 16 | 17 | 18 |
| NBE034 | 19 | 20 | 21 |
| NBE036 | 22 | 23 | 24 |
| NBE038 | 25 | 26 | 27 |
| NBE039 | 28 | 29 | 30 |
| NBE043 | 31 | 32 | 33 |
| NBE045 | 34 | 35 | 36 |
| NBE042 | 37 | 38 | 39 |

More in particular, the invention relates to an isolated polynucleotide hybridisable under stringent conditions, preferably under highly stringent conditions, to a polynucleotide selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38. Advantageously, such polynucleotides may be obtained from filamentous fungi, in particular from *Aspergillus niger*. More specifically, the invention relates to an is isolated polynucleotide having a nucleotide sequence selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38.

The invention also relates to an isolated polynucleotide encoding at least one functional domain of a polypeptide having an amino acid sequences selected from the group consisting of SEQ ID NO: 3, 6, 9, 12, 15, 18, 21, 24, 27, 30, 33, 36 and 39 or functional equivalents thereof.

As used herein, the terms "gene" and "recombinant gene" refer to nucleic acid molecules which may be isolated from chromosomal DNA, which include an open reading frame encoding a protein, e.g. an *Aspergillus niger* lipolytic enzyme. A gene may include coding sequences, non-coding sequences, introns and regulatory sequences. Moreover, a gene refers to an isolated nucleic acid molecule as defined herein.

A nucleic acid molecule of the present invention, such as a nucleic acid molecule having the nucleotide sequence selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38 or a functional equivalent thereof, can be isolated using standard molecular biology techniques and the sequence information provided herein. For example, using all or portion of the nucleic acid sequence selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38 as a hybridization probe, nucleic acid molecules according to the invention can be isolated using standard hybridization and cloning techniques (e.g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989).

Moreover, a nucleic acid molecule encompassing all or a portion of the nucleic acid sequence selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38 can be isolated by the polymerase chain reaction (PCR) using synthetic oligonucleotide primers designed based upon the sequence information contained in the nucleic acid sequence selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to or hybridisable to nucleotide sequences according to the invention can be prepared by standard synthetic techniques, e.g., using an automated DNA synthesizer.

In one preferred embodiment, an isolated nucleic acid molecule of the invention comprises the nucleotide sequence shown in SEQ ID NO: 2. The sequence of SEQ ID NO: 2 corresponds to the coding region of the *Aspergillus niger* gene provided in SEQ ID NO: 1. This cDNA comprises the sequence encoding the *Aspergillus niger* NBE028 polypeptide as shown in SEQ ID NO: 3.

In a second preferred embodiment, an isolated nucleic acid molecule of the invention comprises the nucleotide sequence shown in SEQ ID NO: 5. The sequence of SEQ ID NO: 5 corresponds to the coding region of the *Aspergillus niger* gene provided in SEQ ID NO: 4. This cDNA comprises the sequence encoding the *Aspergillus niger* NBE029 polypeptide as shown in SEQ ID NO: 6.

In a third preferred embodiment, an isolated nucleic acid molecule of the invention comprises the nucleotide sequence shown in SEQ ID NO: 8. The sequence of SEQ ID NO: 8 corresponds to the coding region of the *Aspergillus niger* gene provided in SEQ ID NO: 7. This cDNA comprises the sequence encoding the *Aspergillus niger* NBE030 polypeptide as shown in SEQ ID NO: 9.

In a fourth preferred embodiment, an isolated nucleic acid molecule of the invention comprises the nucleotide sequence shown in SEQ ID NO: 11. The sequence of SEQ ID NO: 11 corresponds to the coding region of the *Aspergillus niger* gene provided in SEQ ID NO: 10. This cDNA comprises the sequence encoding the *Aspergillus niger* NBE031 polypeptide as shown in SEQ ID NO: 12.

In a fifth preferred embodiment, an isolated nucleic acid molecule of the invention comprises the nucleotide sequence shown in SEQ ID NO: 14. The sequence of SEQ ID NO: 14 corresponds to the coding region of the *Aspergillus niger* gene provided in SEQ ID NO: 13. This cDNA comprises the sequence encoding the *Aspergillus niger* NBE032 polypeptide as shown in SEQ ID NO: 15.

In a sixth preferred embodiment, an isolated nucleic acid molecule of the invention comprises the nucleotide sequence shown in SEQ ID NO: 17. The sequence of SEQ ID NO: 17 corresponds to the coding region of the *Aspergillus niger* gene provided in SEQ ID NO: 16. This cDNA comprises the sequence encoding the *Aspergillus niger* NBE033 polypeptide as shown in SEQ ID NO: 18.

In a seventh preferred embodiment, an isolated nucleic acid molecule of the invention comprises the nucleotide sequence shown in SEQ ID NO: 20. The sequence of SEQ ID NO: 20 corresponds to the coding region of the *Aspergillus niger* gene-provided in SEQ ID NO: 19. This cDNA comprises the sequence encoding the *Aspergillus niger* NBE034 polypeptide as shown in SEQ ID NO: 21.

In a eight preferred embodiment, an isolated nucleic acid molecule of the invention comprises the nucleotide sequence shown in SEQ ID NO: 23. The sequence of SEQ ID NO: 23 corresponds to the coding region of the *Aspergillus niger* gene provided in SEQ ID NO: 22. This cDNA comprises the sequence encoding the *Aspergillus niger* NBE034 polypeptide as shown in SEQ ID NO: 24.

In a ninth preferred embodiment, an isolated nucleic acid molecule of the invention comprises the nucleotide sequence shown in SEQ ID NO: 26. The sequence of SEQ ID NO: 26 corresponds to the coding region of the *Aspergillus niger* gene provided in SEQ ID NO: 25. This cDNA comprises the sequence encoding the *Aspergillus niger* NBE034 polypeptide as shown in SEQ ID NO: 27.

In a tenth preferred embodiment, an isolated nucleic acid molecule of the invention comprises the nucleotide sequence shown in SEQ ID NO: 29. The sequence of SEQ ID NO: 29 corresponds to the coding region of the *Aspergillus niger* gene provided in SEQ ID NO: 28. This cDNA comprises the sequence encoding the *Aspergillus niger* NBE034 polypeptide as shown in SEQ ID NO: 30.

In a eleventh preferred embodiment, an isolated nucleic acid molecule of the invention comprises the nucleotide sequence shown in SEQ ID NO: 32. The sequence of SEQ ID NO: 32 corresponds to the coding region of the *Aspergillus niger* gene provided in SEQ ID NO: 31. This cDNA comprises the sequence encoding the *Aspergillus niger* NBE034 polypeptide as shown in SEQ ID NO: 33.

In a twelfth preferred embodiment, an isolated nucleic acid molecule of the invention comprises the nucleotide sequence shown in SEQ ID NO: 35. The sequence of SEQ ID NO: 35 corresponds to the coding region of the *Aspergillus niger* gene provided in SEQ ID NO: 34 This cDNA comprises the sequence encoding the *Aspergillus niger* NBE034 polypeptide as shown in SEQ ID NO: 36.

In a thirteenth preferred embodiment, an isolated nucleic acid molecule of the invention comprises the nucleotide sequence shown in SEQ ID NO: 38. The sequence of SEQ ID NO: 38 corresponds to the coding region of the *Aspergillus niger* gene provided in SEQ ID NO: 37. This cDNA comprises the sequence encoding the *Aspergillus niger* NBE034 polypeptide as shown in SEQ ID NO: 39.

In another preferred embodiment, an isolated nucleic acid molecule of the invention comprises a nucleic acid molecule which is a complement of the nucleotide sequence selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38 or a functional equivalent of these nucleotide sequences. A nucleic acid molecule, which is complementary to another nucleotide sequence, is one that is sufficiently complementary to the other nucleotide sequence such that it can hybridize to the other nucleotide sequence thereby forming a stable duplex.

One aspect of the invention pertains to isolated nucleic acid molecules that encode a polypeptide of the invention or a functional equivalent thereof such as a biologically active fragment or domain, as well as nucleic acid molecules sufficient for use as hybridisation probes to identify nucleic acid molecules encoding a polypeptide of the invention and fragments of such nucleic acid molecules suitable for use as PCR primers for the amplification or mutation of nucleic acid molecules. An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a nucleic acid molecule according to the invention. Also included within the scope of the invention are the complement strands of the nucleic acid molecules described herein.

Sequencing Errors

The sequence information as provided herein should not be so narrowly construed as to require inclusion of erroneously identified bases. The specific sequences disclosed herein can be readily used to isolate the complete gene from filamentous fungi, in particular *Aspergillus niger* which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

Nucleic Acid Fragments, Probes and Primers

A nucleic acid molecule according to the invention may comprise only a portion or a fragment of the nucleic acid sequence selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38, for example a fragment which can be used as a probe or primer or a fragment encoding a portion of protein according to the invention. The nucleotide sequence determined from the cloning of the lipolytic enzyme gene and cDNA allows for the generation of probes and primers designed for use in identifying and/or cloning other lipolytic enzyme family members, as well as lipolytic enzyme homologues from other species. The probe/primer typically comprises substantially purified oligonucleotide which typically comprises a region of nucleotide sequence that hybridizes preferably under highly stringent conditions to at least about 12 or 15, preferably about 18 or 20, preferably about 22 or 25, more preferably about 30, 35, 40, 45, 50, 55, 60, 65, or 75 or more consecutive nucleotides of a nucleotide sequence selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38 or of a functional equivalent thereof.

Probes based on the nucleotide sequences provided herein can be used to detect transcripts or genomic sequences encoding the same or homologous proteins for instance in other organisms. In preferred embodiments, the probe further comprises a label group attached thereto, e.g., the label group can be a radioisotope, a fluorescent compound, an enzyme, or an enzyme cofactor. Such probes can also be used as part of a diagnostic test kit for identifying cells that express a lipolytic enzyme protein.

Identity & homology

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

The skilled person will be aware of the fact that several different computer programmes are available to determine the homology between two sequences. For instance, a comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-453(1970)) algorithm which has been incorporated into the GAP program in the GCG software package (available at www dot gcg dot com), using either a Blossom 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at www dot gcg dot com), using a NWSgapdna.CMP matrix and a gap weight of 40, 50, 60, 70, or 80 and a length weight of 1, 2, 3, 4, 5, or 6. In another embodiment, the percent identity two amino acid or nucleotide sequence is determined using the algorithm of E. Meyers and W. Miller (CABIOS, 4:11-17(1989) which has been incorporated into the ALIGN program (version 2.0) (available at: vega dot iqh dot cnrs dot fr slash bin slash aliqn-quess dot cqi) using a PAM120 weight residue table, a gap length penalty of 12 and a gap penalty of 4.

The nucleic acid and protein sequences of the present invention can further be used as a "query sequence"to perform a search against public databases to, for example, identify other family members or related sequences. Such searches can be performed using the BLASTN and BLASTX programs (version 2.0) of Altschul, et al. (1990) J. Mol. Biol. 215:403-10. BLAST nucleotide searches can be performed with the BLASTN program, score =100, word length =12 to obtain nucleotide sequences homologous to PLP03 nucleic acid molecules of the invention. BLAST protein searches can be performed with the BLASTX program, score =50, word length =3 to obtain amino acid sequences homologous to PLP03 protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., BLASTX and BLASTN) can be used. See www dot ncbi dot nlm dot nih dot gov.

Hybridisation

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, more preferably at least 95% homologous to each other typically remain hybridized to each other.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., preferably at 60° C. and even more preferably at 65° C.

Highly stringent conditions include, for example, hybridizing at 68° C. in 5×SSC/5× Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

Obtaining Full Length DNA from Other Organisms

In a typical approach, cDNA libraries constructed from other organisms, e.g. filamentous fungi, in particular from the species *Aspergillus* can be screened.

For example, *Aspergillus* strains can be screened for homologous polynucleotides by Northern blot analysis. Upon detection of transcripts homologous to polynucleotides according to the invention, cDNA libraries can be constructed from RNA isolated from the appropriate strain, utilizing standard techniques well known to those of skill in the art. Alternatively, a total genomic DNA library can be screened using a probe hybridisable to a polynucleotide according to the invention.

Homologous gene sequences can be isolated, for example, by performing PCR using two degenerate oligonucleotide primer pools designed on the basis of nucleotide sequences as taught herein.

The template for the reaction can be cDNA obtained by reverse transcription of mRNA prepared from strains known or suspected to express a polynucleotide according to the invention. The PCR product can be subcloned and sequenced to ensure that the amplified sequences represent the sequences of a new PLP03 nucleic acid sequence, or a functional equivalent thereof.

The PCR fragment can then be used to isolate a full length cDNA clone by a variety of known methods. For example, the amplified fragment can be labeled and used to screen a bacteriophage or cosmid cDNA library. Alternatively, the labeled fragment can be used to screen a genomic library.

PCR technology can also be used to isolate full-length cDNA sequences from other organisms. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis.

The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Vectors

Another aspect of the invention pertains to vectors, preferably expression vectors, containing a nucleic acid encoding a protein according to the invention or a functional equivalent thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses; adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel; *Gene Expression Technology: Methods in Enzymology* 185, Academic Press, San Diego, Calif. (1990). Regulatory sequences include those which direct constitutive or inducible expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. lipolytic enzymes, mutant lipolytic enzymes, fragments thereof, variants or functional equivalents thereof, fusion proteins, etc.).

The recombinant expression vectors of the invention can be designed for expression of lipolytic enzymes in prokaryotic or eukaryotic cells. For example, a protein according to the invention can be expressed in bacterial cells such as *E. coli* and *Bacillus* species, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. The skilled person will know other suitable promoters. In a specific embodiment, promoters are preferred that are capable of directing a high expression level of lipolytic enzymes in filamentous fungi. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-percipitation, DEAE-dextran-mediated transfection, transduction, infection, lipofection, cationic lipidmediated transfection or electroporation. Suitable methods for transforming or transfecting host cells can be found in Sambrook, et al. (*Molecular Cloning: A Laboratory Manual, 2nd, ed. Cold Spring Harbor Laboratory*, Cold Spring Harbor Laboratory Press, Cold Spring Harbor, N.Y., 1989), Davis et al., *Basic Methods in Molecular Biology* (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those that confer resistance to drugs, such as G418, hygromycin and methatrexate. A nucleic acid encoding a selectable marker is preferably introduced into a host cell on the same vector as that encoding a protein according to the invention or can be introduced on a separate vector. Cells stably transfected with the introduced nucleic acid can be identified by drug selection (e.g. cells that have incorporated the selectable marker gene will survive, while the other cells die).

Expression of proteins in prokaryotes is often carried out in *E. coli* with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety after purification of the fusion protein. Such enzymes, and their cognate recognition sequences, include Factor Xa, thrombin and enterokinase.

As indicated, the expression vectors will preferably contain selectable markers. Such markers include dihydrofolate reductase or neomycin resistance for eukarotic cell culture and tetracyline or ampicilling resistance for culturing in *E. coli* and other bacteria. Representative examples of appropriate host include bacterial cells, such as *E. coli, Streptomyces* and *Salmonella typhimurium*; fungal cells, such as yeast; insect cells such as *Drosophila* S2 and *Spodoptera* Sf9; animal cells such as CHO, COS and Bowes melanoma; and plant cells. Appropriate culture mediums and conditions for the above-described host cells are known in the art.

Among vectors preferred for use in bacteria are pQE70, pQE60 and PQE-9, available from Qiagen; pBS vectors, Phagescript vectors, Bluescript vectors, pNH8A, pNH16A, pNH18A, pNH46A, available from Stratagene; and ptrc99a, pKK223-3, pKK233-3, pDR540, pRIT5 available from Pharmacia. Among preferred eukaryotic vectors are PWLNEO, pSV2CAT, pOG44, pZT1 and pSG available from Stratagene; and pSVK3, pBPV, pMSG and pSVL available from Pharmacia. Other suitable vectors will be readily apparent to the skilled artisan.

Known bacterial promoters for use in the present invention include *E. coli* lad and lacZ promoters, the T3 and T7 promoters, the gpt promoter, the lambda PR, PL promoters and the trp promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Inserting an enhancer sequence into the vector may increase transcription of the DNA encoding the polypeptides of the present invention by higher eukaryotes. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signal may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification.

Polypeptides According to the Invention

The invention provides an isolated polypeptide having the amino acid sequence selected from the group consisting of SEQ ID NO: 3, 6, 9, 12, 15, 18, 21, 24, 27, 30, 33, 36 and 39, an amino acid sequence obtainable by expressing the polynucleotide selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38 in an appropriate host. Also, a peptide or polypeptide comprising a functional equivalent of the above polypeptides is comprised within the present invention. The above polypeptides are collectively comprised in the term "polypeptides according to the invention"

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (*Molecular Cloning: A Laboratory Manual, 2nd, ed. Cold Spring Harbor Laboratory*, Cold Spring Harbor Laboratory Press, Cold Spring Harbor, N.Y., 1989)

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The lipolytic enzyme according to the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

A lipolytic enzyme according to the invention may be advantageously used in baking processes. The amount of enzyme to be added to the dough is determined empirically. It may depend on the quality of the flour used, the degree of improvement which is required, the kind of bread or baked goods, the method of preparing the dough, the proportion of other ingredients etcetera.

Protein Fragments

The invention also features biologically active fragments of the polypeptides according to the invention.

Biologically active fragments of a polypeptide of the invention include polypeptides comprising amino acid sequences sufficiently identical to or derived from the amino acid sequence of the lipolytic enzyme (e.g., the amino acid sequence selected from the group consisting of SEQ ID NO: 3, 6, 9, 12, 15, 18, 21, 24, 27, 30, 33, 36 and 39), which include fewer amino acids than the full length protein, and exhibit at least one biological activity of the corresponding full-length protein. Typically, biologically active fragments comprise a domain or motif with at least one activity of the corresponding full length protein.

A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

The invention also features nucleic acid fragments which encode the above biologically active fragments of the lipolytic enzyme protein.

Fusion Proteins

The proteins of the present invention or functional equivalents thereof, e.g., biologically active portions thereof, can be operatively linked to a non-lipolytic enzyme polypeptide (e.g., heterologous amino acid sequences) to form fusion proteins. As used herein, a lipolytic enzyme "chimeric protein" or "fusion protein" comprises a lipolytic enzyme polypeptide operatively linked to a non-lipolytic enzyme polypeptide. A "lipolytic enzyme polypeptide" refers to a polypeptide having an amino acid sequence selected from the group consisting of SEQ ID NO: 3, 6, 9, 12, 15, 18, 21, 24, 27, 30, 33, 36 and 39, whereas a "non-lipolytic enzyme polypeptide" refers to a polypeptide having an amino acid sequence corresponding to a protein which is not substantially homologous to the lipolytic enzyme, e.g., a protein which is different from the lipolytic enzyme and which is derived from the same or a different organism. Within a lipolytic enzyme fusion protein the lipolytic enzyme polypeptide can correspond to all or a portion of a lipolytic enzyme protein. In a preferred embodiment, a lipolytic enzyme fusion protein comprises at least one biologically active fragment of a lipolytic enzyme protein. In another preferred embodiment, a lipolytic enzyme fusion protein comprises at least two biologically active portions of a lipolytic enzyme protein. Within the fusion protein, the term "operatively linked" is intended to indicate that the lipolytic enzyme polypeptide and the non-lipolytic enzyme polypeptide are fused in-frame to each other. The non-lipolytic enzyme polypeptide can be fused to the N-terminus or C-terminus of the lipolytic enzyme polypeptide.

For example, in one embodiment, the fusion protein is a GST-lipolytic enzyme fusion protein in which the lipolytic enzyme sequence is fused to the C-terminus of the GST sequence. Such fusion proteins can facilitate the purification of recombinant lipolytic enzyme(s). In another embodiment, the fusion protein is a lipolytic enzyme protein containing a heterologous signal sequence at its N-terminus. In certain host cells (e.g., mammalian and Yeast host cells), expression and/or secretion of lipolytic enzyme can be increased through use of a hetereologous signal sequence.

In another example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokarytic heterologous signal sequences include the phoA secretory signal (Sambrook et al., supra) and the protein A secretory signal (Pharmacia Biotech; Piscataway, N.J.).

A signal sequence can be used to facilitate secretion and isolation of a protein or polypeptide of the invention. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain. Thus, for instance, the sequence encoding the polypeptide may be fused to a marker sequence, such as a sequence encoding a peptide, which facilitates purification of the fused polypeptide. In certain preferred embodiments of this aspect of the invention, the marker sequence is a hexahistidine peptide, such as the tag provided in a pQE vector (Qiagen, Inc.), among others, many of which are commercially available. As described in Gentz et al, *Proc. Natl. Acad. Sci. USA* 86:821-824 (1989), for instance, hexa-histidine provides for convenient purificaton of the fusion protein. The HA tag is another peptide useful for purification which corresponds to an epitope derived of influenza hemaglutinin protein, which has been described by Wilson et al., *Cell* 37:767 (1984), for instance.

Preferably, a chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g, a GST polypeptide). A lipolytic enzyme-encoding nucleic acid can be cloned into such an expression vector such that the fusion moiety is linked in-frame to the lipolytic enzyme protein.

Functional Equivalents

The terms "functional equivalents" and "functional variants" are used interchangeably herein. Functional equivalents of lipolytic enzyme encoding DNA are isolated DNA fragments that encode a polypeptide that exhibits a particular function of the *Aspergillus niger* lipolytic enzyme as defined herein. A functional equivalent of a lipolytic enzyme polypeptide according to the invention is a polypeptide that exhibits at least one function of an *Aspergillus niger* lipolytic enzyme as defined herein. Functional equivalents therefore also encompass biologically active fragments.

Functional protein or polypeptide equivalents may contain only conservative substitutions of one or more amino acids in the amino acid sequences selected from the group consisting of SEQ ID NO: 3, 6, 9, 12, 15, 18, 21, 24, 27, 30, 33, 36 and 39 or substitutions, insertions or deletions of non-essential amino acids. Accordingly, a non-essential amino acid is a residue that can be altered in the amino acid sequences selected from the group consisting of SEQ ID NO: 3, 6, 9, 12, 15, 18, 21, 24, 27, 30, 33, 36 and 39 without substantially altering the biological function. For example, amino acid residues that are conserved among the lipolytic enzyme proteins of the present invention, are predicted to be particularly unamenable to alteration. Furthermore, amino acids conserved among the lipolytic enzyme proteins according to the present invention and other lipolytic enzymes are not likely to be amenable to alteration.

The term "conservative substitution" is intended to mean that a substitution in which the amino acid residue is replaced with an amino acid residue having a similar side chain. These families are known in the art and include amino acids with basic side chains (e.g. lysine, arginine and hystidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine tryptophan, histidine).

Functional nucleic acid equivalents may typically contain silent mutations or mutations that do not alter the biological function of encoded polypeptide. Accordingly, the invention provides nucleic acid molecules encoding lipolytic enzyme proteins that contain changes in amino acid residues that are not essential for a particular biological activity. Such lipolytic enzyme proteins differ in amino acid sequence selected from the group consisting of SEQ ID NO: 3, 6, 9, 12, 15, 18, 21, 24, 27, 30, 33, 36 and 39 yet retain at least one biological activity. In one embodiment the isolated nucleic acid molecule comprises a nucleotide sequence encoding a protein, wherein the protein comprises a substantially homologous amino acid sequence of at least about 60%, 65%, 70%, 75%, 80%, 85%, 90%, 95%, 96%, 97%, 98%, 99% or more homologous to the amino acid sequence selected from the group consisting of SEQ ID NO: 3, 6, 9, 12, 15, 18, 21, 24, 27, 30, 33, 36 and 39.

For example, guidance concerning how to make phenotypically silent amino acid substitutions is provided in Bowie, J. U. et al., Science 247:1306-1310 (1990) wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As the authors state, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, supra, and the references cited therein.

An isolated nucleic acid molecule encoding a protein homologous to the protein selected from the group consisting of SEQ ID NO: 3, 6, 9, 12, 15, 18, 21, 24, 27, 30, 33, 36 and 39 can be created by introducing one or more nucleotide substitutions, additions or deletions into the corresponding coding nucleotide sequences (Table 1) such that one or more amino acid substitutions, deletions or insertions are introduced into the encoded protein. Such mutations may be introduced by standard techniques, such as site-directed mutagenesis and PCR-mediated mutagenesis.

The term "functional equivalents" also encompasses orthologues of the *Aspergillus niger* lipolytic enzymes provided herein. Orthologues of the *Aspergillus niger* lipolytic enzymes are proteins that can be isolated from other strains or species and possess a similar or identical biological activity. Such orthologues can readily be identified as comprising an amino acid sequence that is substantially homologous to the amino acid sequences selected from the group consisting of SEQ ID NO: 3, 6, 9, 12, 15, 18, 21, 24, 27, 30, 33, 36 and 39.

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 60%, preferably 65%, more preferably 70%, even more preferably 75%, 80%, 85%, 90%, 95%, 96%, 97%, 98% or 99% identity or more are defined herein as sufficiently identical.

Also, nucleic acids encoding other lipolytic enzyme family members, which thus have a nucleotide sequence that differs from a nucleotide sequence selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38, are within the scope of the invention. Moreover, nucleic acids encoding lipolytic enzyme proteins from different species which thus have a nucleotide sequence which differs from a nucleotide sequence selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38 are within the scope of the invention.

Nucleic acid molecules corresponding to variants (e.g. natural allelic variants) and homologues of the polynucleotides of the invention can be isolated based on their homology to the nucleic acids disclosed herein using the cDNAs disclosed herein or a suitable fragment thereof, as a hybridisation probe according to standard hybridisation techniques preferably under highly stringent hybridisation conditions.

In addition to naturally occurring allelic variants of the *Aspergillus niger* sequences provided herein, the skilled person will recognise that changes can be introduced by mutation into the nucleotide sequences selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38 thereby leading to changes in the amino acid sequence of the lipolytic enzyme protein without substantially altering the function of the protein.

In another aspect of the invention, improved lipolytic enzymes are provided. Improved lipolytic enzymes are proteins wherein at least one biological activity is improved. Such proteins may be obtained by randomly introducing mutations along all or part of the lipolytic enzyme coding sequence, such as by saturation mutagenesis, and the resulting mutants can be expressed recombinantly and screened for biological activity. For instance, the art provides for standard assays for measuring the enzymatic activity of lipolytic enzymes and thus improved proteins may easily be selected.

In a preferred embodiment the lipolytic enzyme has an amino acid sequence selected from the group consisting of SEQ ID NO: 3, 6, 9, 12, 15, 18, 21, 24, 27, 30, 33, 36 and 39. In another embodiment, the lipolytic enzyme is substantially homologous to the amino acid sequence selected from the group consisting of SEQ ID NO: 3, 6, 9, 12, 15, 18, 21, 24, 27, 30, 33, 36 and 39 and retains at least one biological activity of a polypeptide selected from the group consisting of SEQ ID NO: 3, 6, 9, 12, 15, 18, 21, 24, 27, 30, 33, 36 and 39, yet differs in amino acid sequence due to natural variation or mutagenesis as described above.

In a further preferred embodiment, the lipolytic enzyme has an amino acid sequence encoded by an isolated nucleic acid fragment capable of hybridising to a nucleic acid selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38, preferably under highly stringent hybridisation conditions.

Accordingly, the lipolytic enzyme is a protein which comprises an amino acid sequence at least about 60%, 65%, 70%, 75%, 80%, 85%, 90%, 95%, 96%, 97%, 98%, 99% or more homologous to the amino acid sequence selected from the group consisting of SEQ ID NO: 3, 6, 9, 12, 15, 18, 21, 24, 27, 30, 33, 36 and 39 and retains at least one functional activity of the polypeptide selected from the group consisting of SEQ ID NO: 3, 6, 9, 12, 15, 18, 21, 24, 27, 30, 33, 36 and 39.

In particular, the lipolytic enzyme is a protein which comprises an amino acid sequence at least about 50%, 55%, 60%, 65%, 70%, 75%, 80%, 85%, 90%, 95%, 96%, 97%, 98%, 99% or more homologous to the amino acid sequence shown in SEQ ID NO: 3 or the lipolytic enzyme is a protein which comprises an amino acid sequence at least about 55%, 60%, 65%, 70%, 75%, 80%, 85%, 90%, 95%, 96%, 97%, 98%, 99% or more homologous to the amino acid sequence shown in SEQ ID NO: 6, or the lipolytic enzyme is a protein which comprises an amino acid sequence at least about 75%, 80%, 85%, 90%, 95%, 96%, 97%, 98%, 99% or more homologous to the amino acid sequence shown in SEQ ID NO: 9, or the lipolytic enzyme is a protein which comprises an amino acid sequence at least about 40%, 45%, 50%, 55%, 60%, 65%, 70%, 75%, 80%, 85%, 90%, 95%, 96%, 97%, 98%, 99% or more homologous to the amino acid sequence shown in SEQ ID NO: 12 or the lipolytic enzyme is a protein which comprises an amino acid sequence at least about 40%, 45%, 50%, 55%, 60%, 65%, 70%, 75%, 80%, 85%, 90%, 95%, 96%, 97%, 98%, 99% or more homologous to the amino acid sequence shown in SEQ ID NO: 15, or the lipolytic enzyme is a protein which comprises an amino acid sequence at least about 40%, 45%, 50%, 55%, 60%, 65%, 70%, 75%, 80%, 85%, 90%, 95%, 96%, 97%, 98%, 99% or more homologous to the amino acid sequence shown in SEQ ID NO: 18 or the lipolytic enzyme is a protein which comprises an amino acid sequence at least about 40%, 45%, 50%, 55%, 60%, 65%, 70%, 75%, 80%, 85%, 90%, 95%, 96%, 97%, 98%, 99% or more homologous to the amino acid sequence shown in SEQ ID NO: 21, or the lipolytic enzyme is a protein which comprises an amino acid sequence at least about 40%, 45%, 50%, 55%, 60%, 65%, 70%, 75%, 80%, 85%, 90%, 95%, 96%, 97%, 98%, 99% or more homologous to the amino acid sequence shown in SEQ ID NO: 24 or the lipolytic enzyme is a protein which comprises an amino acid sequence at least about 40%, 45%, 50%, 55%, 60%, 65%, 70%, 75%, 80%, 85%, 90%, 95%, 96%, 97%, 98%, 99% or more homologous to the amino acid sequence shown in SEQ ID NO: 27, or the lipolytic enzyme is a protein which comprises an amino acid sequence at least about 40%, 45%, 50%, 55%, 60%, 65%, 70%, 75%, 80%, 85%, 90%, 95%, 96%, 97%, 98%, 99% or more homologous to the amino acid sequence shown in SEQ ID NO: 30 or the lipolytic enzyme is a protein which comprises an amino acid sequence at least about 40%, 45%, 50%, 55%, 60%, 65%, 70%, 75%, 80%, 85%, 90%, 95%, 96%, 97%, 98%, 99% or more homologous to the amino acid sequence shown in SEQ ID NO: 33, or the lipolytic enzyme is a protein which comprises an amino acid sequence at least about 40%, 45%, 50%, 55%, 60%, 65%, 70%, 75%, 80%, 85%, 90%, 95%, 96%, 97%, 98%, 99% or more homologous to the amino acid sequence shown in SEQ ID NO: 36 or the lipolytic enzyme is a protein which comprises an amino acid sequence at least about 40%, 45%, 50%, 55%, 60%, 65%, 70%, 75%, 80%, 85%, 90%, 95%, 96%, 97%, 98%, 99% or more homologous to the amino acid sequence shown in SEQ ID NO: 39.

Functional equivalents of a protein according to the invention can also be identified e.g. by screening combinatorial libraries of mutants, e.g. truncation mutants, of the protein of the invention for lipolytic enzyme activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods that can be used to produce libraries of potential variants of the polypeptides of the invention from a degenerate oligonucleotide sequence. Methods for synthesizing degenerate oligonubleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3):327-331).

It will be apparent for the person skilled in the art that DNA sequence polymorphisms that may lead to changes in the amino acid sequence of the lipolytic enzyme may exist within a given population. Such genetic polymorphisms may exist in cells from different populations or within a population due to natural allelic variation. Allelic variants may also include functional equivalents.

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides, can be used as hybridization probes or polymerase chain reaction (PCR) primers. Uses of the nucleic acid molecules of the present invention that do not encode a polypeptide having a lipolytic enzyme activity include, inter alia, (1) isolating the gene encoding the lipolytic enzyme protein, or allelic variants thereof from a cDNA library e.g. from other organisms than *Aspergillus niger*, (2) in situ hybridization (e.g. FISH) to metaphase chromosomal spreads to provide precise chromosomal location of the lipolytic enzyme gene as described in Verma et al., Human Chromosomes: a Manual of Basic Techniques, Pergamon Press, New York (1988); (3) Northern blot analysis for detecting expression of lipolytic enzyme mRNA in specific tissues and/or cells and 4) probes and primers that can be used as a diagnostic tool to analyse the presence of a nucleic acid hybridisable to the lipolytic enzyme probe in a given biological (e.g. tissue) sample.

Also encompassed by the invention is a method of obtaining a functional equivalent of a lipolytic enzyme-encoding gene or cDNA. Such a method entails obtaining a labelled probe that includes an isolated nucleic acid which encodes all or a portion of the sequence selected from the group consisting of SEQ ID NO: 3, 6, 9, 12, 15, 18, 21, 24, 27, 30, 33, 36 and 39 or a variant thereof; screening a nucleic acid fragment library with the labelled probe under conditions that allow hybridisation of the probe to nucleic acid fragments in the library, thereby forming nucleic acid duplexes, and preparing a full-length gene sequence from the nucleic acid fragments in any labelled duplex to obtain a gene related to the lipolytic enzyme gene.

In one embodiment, a nucleic acid of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence selected from the group consisting of SEQ ID NO: 1, 2, 4, 5, 7, 8, 10, 11, 13, 14, 16, 17, 19, 20, 22, 23, 25, 26, 28, 29, 31, 32, 34, 35, 37 and 38 or the complement thereof.

In another preferred embodiment a polypeptide of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to an amino acid sequence selected from the group consisting of SEQ ID NO: 3, 6, 9, 12, 15, 18, 21, 24, 27, 30, 33, 36 and 39.

Host Cells

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from filamentous fungi, in particular *Aspergillus niger*.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

Host cells also include, but are not limited to, mammalian cell lines such as CHO, VERO, BHK, HeLa, COS, MDCK, 293, 3T3, WI38, and choroid plexus cell lines.

If desired, the polypeptides according to the invention can be produced by a stably-transfected cell line. A number of vectors suitable for stable transfection of mammalian cells are available to the public, methods for constructing such cell lines are also publicly known, e.g., in Ausubel et al. (supra).

Antibodies

The invention further features antibodies, such as monoclonal or polyclonal antibodies, that specifically bind lipolytic enzyme proteins according to the invention.

As used herein, the term "antibody" (Ab) or "monoclonal antibody" (Mab) is meant to include intact molecules as well as antibody fragments (such as, for example, Fab and $F(ab')_2$ fragments) which are capable of specifically binding to lipolytic enzyme protein. Fab and $F(ab')_2$ fragments lack the Fc fragment of intact antibody, clear more rapidly from the circulation, and may have less non-specific tissue binding of an intact antibody (Wahl et al., *J. Nucl. Med.* 24:316-325 (1983)). Thus, these fragments are preferred.

The antibodies of the present invention may be prepared by any of a variety of methods. For example, cells expressing the lipolytic enzyme protein or an antigenic fragment thereof can be administered to an animal in order to induce the production of sera containing polyclonal antibodies. In a preferred method, a preparation of lipolytic enzyme protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or lipolytic enzyme protein binding fragments thereof). Such monoclonal antibodies can be prepared using hybridoma technology (Kohler et al., *Nature* 256:495 (1975); Kohler et al., *Eur. J. Immunol.* 6:511 (1976); Hammerling et al., In: *Monoclonal Antibodies and T-Cell Hybridomas*, Elsevier, N.Y., pp. 563-681 (1981)). In general, such procedures involve immunizing an animal (preferably a mouse) with a lipolytic enzyme protein antigen or, with a lipolytic enzyme protein expressing cell. The splenocytes of such mice are extracted and fused with a suitable myeloma cell line. Any suitable myeloma cell line may be employed in accordance with the present invention; however, it is preferably to employ the parent myeloma cell line ($SP_2O$), available from the American Type Culture Collection, Rockville, Md. After fusion, the resulting hybridoma cells are selectively maintained in HAT medium, and then cloned by limiting dilution as described by Wands et al. (*Gastro-enterology* 80:225-232 (1981)). The hybridoma cells obtained through such a selection are then assayed to identify clones which secrete antibodies capable of binding the lipolytic enzyme protein antigen. In general, the polypeptides can be coupled to a carrier protein, such as KLH, as described in Ausubel et al., supra, mixed with an adjuvant, and injected into a host mammal.

In particular, various host animals can be immunized by injection of a polypeptide of interest. Examples of suitable host animals include rabbits, mice, guinea pigs, and rats. Various adjuvants can be used to increase the immunological response, depending on the host species, including but not limited to Freund's (complete and incomplete), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum*. Polyclonal antibodies are heterogeneous populations of antibody molecules derived from the sera of the immunized animals.

Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies are tested for specific recognition of a protein according to the invention or functional equivalent thereof in an immunoassay, such as a Western blot or immunoprecipitation analysis using standard techniques, e.g., as described in Ausubel et al., supra. Antibodies that specifically bind to a protein according to the invention or functional equivalents thereof are useful in the invention. For example, such antibodies can be used in an immunoassay to detect a protein according to the invention in pathogenic or non-pathogenic strains of *Aspergillus* (e.g., in *Aspergillus* extracts).

Preferably, antibodies of the invention are produced using fragments of a protein according to the invention that appear likely to be antigenic, by criteria such as high frequency of charged residues. For example, such fragments may be generated by standard techniques of PCR, and then cloned into the pGEX expression vector (Ausubel et al., supra). Fusion proteins may then be expressed in *E. coli* and purified using a glutathione agarose affinity matrix as described in Ausubel, et al., supra. If desired, several (e.g., two or three) fusions can be generated for each protein, and each fusion can be injected into at least two rabbits. Antisera can be raised by injections in a series, typically including at least three booster injections. Typically, the antisera are checked for their ability to immunoprecipitate the protein according to the invention or functional equivalents thereof whereas unrelated proteins may serve as a control for the specificity of the immune reaction.

Alternatively, techniques described for the production of single chain antibodies (U.S. Pat. Nos. 4,946,778 and 4,704, 692) can be adapted to produce single chain antibodies against a protein according to the invention or functional equivalents thereof. Kits for generating and screening phage display libraries are commercially available e.g. from Pharmacia.

Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 20791; PCT Publication No. WO 92/20791; PCT Publication No.

WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246; 1275-1281; Griffiths et al. (1993) *EMBO J.* 12:725-734.

Polyclonal and monoclonal antibodies that specifically bind a protein according to the invention of functional equivalents thereof can be used, for example, to detect expression of a gene encoding a protein according to the invention or a functional equivalent thereof e.g. in another strain of *Aspergillus*. For example, a protein according to the invention can be readily detected in conventional immunoassays of *Aspergillus* cells or extracts. Examples of suitable assays include, without limitation, Western blotting, ELISAs, radio-immune assays, and the like.

By "specifically binds" is meant that an antibody recognizes and binds a particular antigen, e.g., a protein according to the invention, but does not substantially recognize and bind other unrelated molecules in a sample.

Antibodies can be purified, for example, by affinity chromatography methods in which the polypeptide antigen is immobilized on a resin.

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in cells or tissue as part of a clinical testing procedure, e.g., to, for example, determine the efficacy of a given treatment regimen or in the diagnosis of Aspergillosis.

Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive materials include $^{125}$I, $^{131}$I, $^{35}$S or $^{3}$H.

Preferred epitopes encompassed by the antigenic peptide are regions that are located on the surface of the protein, e.g., hydrophilic regions. Hydrophobicity plots of the proteins of the invention can be used to identify hydrophilic regions.

The antigenic peptide of a protein of the invention comprises at least 7 (preferably 10, 15, 20, or 30) contiguous amino acid residues of the amino acid sequense selected from the group consisting of SEQ ID NO: 3, 6, 9, 12, 15, 18, 21, 24, 27, 30, 33, 36 and 39 and encompasses an epitope of the protein such that an antibody raised against the peptide forms a specific immune complex with the protein.

Preferred epitopes encompassed by the antigenic peptide are regions of the protein according to the invention that are located on the surface of the protein, e.g., hydrophilic regions, hydrophobic regions, alpha regions, beta regions, coil regions, turn regions and flexible regions.

Immunoassays

Qualitative or quantitative determination of a polypeptide according to the present invention in a biological sample can occur using any art-known method. Antibody-based techniques provide special advantages for assaying specific polypeptide levels in a biological sample.

In these, the specific recognition is provided by the primary antibody (polyclonal or monoclonal) but the secondary detection system can utilize fluorescent, enzyme, or other conjugated secondary antibodies. As a result, an immunocomplex is obtained.

Accordingly, the invention provides a method for diagnosing whether a certain organism is infected with *Aspergillus* comprising the steps of:
   Isolating a biological sample from said organism suspected to be infected with *Aspergillus*,
   reacting said biological sample with an antibody according to the invention,
   determining whether immunecomplexes are formed.

Tissues can also be extracted, e.g., with urea and neutral detergent, for the liberation of protein for Western-blot or dot/slot assay. This technique can also be applied to body fluids.

Other antibody-based methods useful for detecting a protein according to the invention include immunoassays, such as the enzyme linked immunosorbent assay (ELISA) and the radioimmunoassay (RIA). For example, monoclonal antibodies against a protein according to the invention can be used both as an immunoabsorbent and as an enzyme-labeled probe to detect and quantify the protein according to the invention. The amount of protein present in the sample can be calculated by reference to the amount present in a standard preparation using a linear regression computer algorithm. In another ELISA assay, two distinct specific monoclonal antibodies can be used to detect a protein according to the invention in a biological fluid. In this assay, one of the antibodies is used as the immuno-absorbent and the other as the enzyme-labeled probe.

The above techniques may be conducted essentially as a "one-step" or "two-step" assay. The "one-step" assay involves contacting a protein according to the invention with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Activity of an oxidase label may be assayed by measuring the concentration of hydrogen peroxide formed by the enzyme-labelled antibody/substrate reaction.

Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Specific binding of a test compound to a protein according to the invention can be detected, for example, in vitro by reversibly or irreversibly immobilizing the protein according to the invention on a substrate, e.g., the surface of a well of a 96-well polystyrene microtitre plate. Methods for immobilizing polypeptides and other small molecules are well known in the art. For example, the microtitre plates can be coated with a protein according to the invention by adding the protein in a solution (typically, at a concentration of 0.05 to 1 mg/ml in a volume of 1-100 ul) to each well, and incubating the plates at room temperature to 37° C. for 0.1 to 36 hours. Proteins that are not bound to the plate can be removed by shaking the excess solution from the plate, and then washing the plate (once or repeatedly) with water or a buffer. Typically, the protein is contained in water or a buffer. The plate is then washed with a buffer that lacks the bound protein. To block the free protein-binding sites on the plates, the plates are blocked with a protein that is unrelated to the bound protein. For example, 300 ul of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate.

Binding of the test compound to the polypeptides according to the invention can be detected by any of a variety of artknown methods. For example, a specific antibody can be used in an immunoassay. If desired, the antibody can be labeled (e.g., fluorescently or with a radioisotope) and detected directly (see, e.g., West and McMahon, J. Cell Biol. 74:264, 1977). Alternatively, a second antibody can be used for detection (e.g., a labeled antibody that binds the Fc portion of an ant-AN97 antibody). In an alternative detection method, the protein according to the invention is labeled, and the label is detected (e.g., by labeling a protein according to the invention with a radioisotope, fluorophore, chromophore, or the like). In still another method, the protein according to the invention is produced as a fusion protein with a protein that can be detected optically, e.g., green fluorescent protein (which can be detected under UV light). In an alternative method, the protein according to the invention can be covalently attached to or fused with an enzyme having a detectable enzymatic activity, such as horse radish peroxidase, alkaline phosphatase, alpha-galactosidase, or glucose oxidase. Genes encoding all of these enzymes have been cloned and are readily available for use by those of skill in the art. If desired, the fusion protein can include an antigen, and such an antigen can be detected and measured with a polyclonal or monoclonal antibody using conventional methods. Suitable antigens include enzymes (e.g., horse radish peroxidase, alkaline phosphatase, and alpha-galactosidase) and non-enzymatic polypeptides (e.g., serum proteins, such as BSA and globulins, and milk proteins, such as caseins).

Epitopes, Antigens and Immunogens

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, H. M. et al., Proc. Natl. Acad. Sci. USA 81:3998-4002 (1984).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G. et al., Science 219:660-666 (1984). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope bearing peptides or polypeptides are useful to detect the mimicked protein, and antibodies to different peptides may be used for tracking the fate of various regions of a protein precursor which undergoes posttranslation processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson, I. A. et al., Cell 37:767-778 at 777 (1984). The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and Including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies.

Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HAI polypeptide which were prepared and characterized (by ELISA-type binding studies) in less than four weeks. Houghten, R. A., Proc. Natl. Acad. Sci. USA 82:5131-5135 (1985). This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods.

A completely manual procedure allows 500-1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., Proc. Natl. Acad. Sci. USA 82:910-914; and Bittle, F. J. et al., J. Gen. Virol. 66:2347-2354 (1985).

Generally, animals may be immunized with free peptide; however, anti-peptide antibody titer may be boosted by coupling of the peptide to a macromolecular carrier, such as keyhole limpet hemocyanin (KLH) or tetanus toxoid. For instance, peptides containing cysteine may be coupled to carrier using a linker such as maleimidobenzoyl-N-hydroxysuccinimide ester (MBS), while other peptides may be coupled to carrier using a more general linking agent such as glutaraldehyde.

Animals such as rabbits, rats and mice are immunized with either free or carrier coupled peptides, for instance, by intraperitoneal and/or intradermal injection of emulsions containing about 100 ug peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., 1984, supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1-C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Use of Lipolytic Enzymes in Industrial Processes

The invention also relates to the use of the lipolytic enzyme according to the invention in a selected number of industrial processes. Despite the long-term experience obtained with these processes, the lipolytic enzyme according to the invention features a number of significant advantages over the enzymes currently used. Depending on the specific application, these advantages can include aspects like lower production costs, higher specificity towards the substrate, less antigenic, less undesirable side activities, higher yields when produced in a suitable microorganism, more suitable pH and temperature ranges, better tastes of the final product as well as food grade and kosher aspects.

The present invention also relates to methods for preparing a dough or a baked product comprising incorporating into the dough an effective amount of a lipolytic enzyme of the present invention which improves one or more properties of the dough or the baked product obtained from the dough relative to a dough or a baked product in which the polypeptide is not incorporated.

The phrase "incorporating into the dough" is defined herein as adding the lipolytic enzyme according to the invention to the dough, any ingredient from which the dough is to be made, and/or any mixture of dough ingredients form which the dough is to be made. In other words, the lipolytic enzyme according to the invention may be added in any step of the dough preparation and may be added in one, two or more steps. The lipolytic enzyme according to the invention is added to the ingredients of a dough that is kneaded and baked to make the baked product using methods well known in the art. See, for example, U.S. Pat. No. 4,567,046, EP-A-426, 211, JP-A-60-78529, JP-A-62-111629, and JP-A-63-258528.

The term "effective amount" is defined herein as an amount of the lipolytic enzyme according to the invention that is sufficient for providing a measurable effect on at least one property of interest of the dough and/or baked product.

The term "improved property" is defined herein as any property of a dough and/or a product obtained from the dough, particularly a baked product, which is improved by the action of the lipolytic enzyme according to the invention relative to a dough or product in which the lipolytic enzyme according to the invention is not incorporated. The improved property may include, but is not limited to, increased strength of the dough, increased elasticity of the dough, increased stability of the dough, reduced stickiness of the dough, improved extensibility of the dough, improved flavour of the baked product, improved anti-staling of the baked product.

The improved property may be determined by comparison of a dough and/or a baked product prepared with and without addition of a polypeptide of the present invention in accordance with the methods of present invention are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to mechanical abuse thus better maintaining its shape and volume.

The term "reduced stickiness of the dough" is defined herein as the property of a dough that has less tendency to adhere to surfaces, e.g., in the dough production machinery, and is either evaluated empirically by the skilled test baker or measured by the use of a texture analyser (e.g., TAXT2) as known in the art.

The term "improved extensibility of the dough" is defined herein as the property of a dough that can be subjected to increased strain or stretching without rupture.

The term "improved machineability of the dough" is defined herein as the property of a dough that is generally less sticky and/or more firm and/or more elastic.

The term "increased volume of the baked product" is measured as the specific volume of a given loaf of bread (volume/weight) determined typically by the traditional rapeseed displacement method.

The term "improved crumb structure of the baked product" is defined herein as the property of a baked product with finer and/or thinner cell walls in the crumb and/or more uniform/homogenous distribution of cells in the crumb and is usually evaluated empirically by the skilled test baker.

The term "improved softness of the baked product" is the opposite of "firmness" and is defined herein as the property of a baked product that is more easily compressed and is evaluated either empirically by the skilled test baker or measured by the use of a texture analyzer (e.g., TAXT2) as known in the art.

The term "improved flavor of the baked product" is evaluated by a trained test panel.

The term "improved anti-staling of the baked product" is defined herein as the properties of a baked product that have a reduced rate of deterioration of quality parameters, e.g., softness and/or elasticity, during storage.

The term "dough" is defined herein as a mixture of flour and other ingredients firm enough to knead or roll. The dough may be fresh, frozen, pre-bared, or pre-baked. The preparation of frozen dough is described by Kulp and Lorenz in Frozen and Refrigerated Doughs and Batters.

The term "baked product" is defined herein as any product prepared from a dough, either of a soft or a crisp character. Examples of baked products, whether of a white, light or dark type, which may be advantageously produced by the present invention are bread (in particular white, whole-meal or rye bread), typically in the form of loaves or rolls, French baguette-type bread, pasta, pita bread, tortillas, tacos, cakes, pancakes, biscuits, cookies, pie crusts, steamed bread, and crisp bread, and the like.

Lipolytic enzyme of the present invention and/or additional enzymes to be used in the methods of the present invention may be in any form suitable for the use in question, e.g., in the form of a dry powder, agglomerated powder, or granulate, in particular a non-dusting granulate, liquid, in particular a stabilized liquid, or protected enzyme such described in WO01/11974 and WO02/26044. Granulates and agglomerated powders may be prepared by conventional methods, e.g., by spraying the lipolytic enzyme according to the invention onto a carrier in a fluid-bed granulator. The carrier may consist of particulate cores having a suitable particle size. The carrier may be soluble or insoluble, e.g., a salt (such as NaCl or sodium sulphate), sugar (such as sucrose or lactose), sugar alcohol (such as sorbitol), starch, rice, corn grits, or soy. The lipolytic enzyme according to the invention and/or additional enzymes may be contained in slow-release formulations. Methods for preparing slow-release formulations are well known in the art. Adding nutritionally acceptable stabilizers such as sugar, sugar alcohol, or another polyol, and/or lactic acid or another organic acid according to established methods may for instance, stabilize liquid enzyme preparations.

The lipolytic enzyme according to the invention may also be incorporated in yeast comprising compositions such as disclosed in EP-A-0619947, EP-A-0659344 and WO02/49441.

For inclusion in pre-mixes of flour it is advantageous that the polypeptide according to the invention is in the form of a dry product, e.g., a non-dusting granulate, whereas for inclusion together with a liquid it is advantageously in a liquid form.

One or more additional enzymes may also be incorporated into the dough. The additional enzyme may be of any origin, including mammalian and plant, and preferably of microbial (bacterial, yeast or fungal) origin and may be obtained by techniques conventionally used in the art.

In a preferred embodiment, the additional enzyme may be an amylase, such as an alpha-amylase (useful for providing sugars fermentable by yeast and retarding staling) or beta-amylase, cyclodextrin glucanotransferase, peptidase, in particular, an exopeptidase (useful in flavour enhancement), transglutaminase, lipase (useful for the modification of lipids present in the dough or dough constituents so as to soften the dough), phospholipase, cellulase, hemicellulase, in particular a pentosanase such as xylanase (useful for the partial hydrolysis of pentosans which increases the extensibility of the dough), protease (useful for gluten weakening in particular when using hard wheat flour), protein disulfide isomerase, e.g., a protein disulfide isomerase as disclosed in WO 95/00636, glycosyltransferase, peroxidase (useful for improving the dough consistency), laccase, or oxidase, e.g., an glucose oxidase, hexose oxidase, aldose oxidase, pyranose oxidase, lipoxygenase or L-amino acid oxidase (useful in improving dough consistency).

When one or more additional enzyme activities are to be added in accordance with the methods of the present invention, these activities may be added separately or together with the polypeptide according to the invention, optionally as constituent(s) of the bread-improving and/or dough-improving composition. The other enzyme activities may be any of the enzymes described above and may be dosed in accordance with established baking practices.

The present invention also relates to methods for preparing a baked product comprising baking a dough obtained by a method of the present invention to produce a baked product. The baking of the dough to produce a baked product may be performed using methods well known in the art.

The present invention also relates to doughs and baked products, respectively, produced by the methods of the present invention.

The present invention further relates to a pre-mix, e.g., in the form of a flour composition, for dough and/or baked products made from dough, in which the pre-mix comprises a polypeptide of the present invention. The term "pre-mix" is defined herein to be understood in its conventional meaning, i.e., as a mix of baking agents, generally including flour, which may be used not only in industrial bread-baking plants/facilities, but also in retail bakeries. The pre-mix may be prepared by mixing the polypeptide or a bread-improving and/or dough-improving composition of the invention comprising the polypeptide with a suitable carrier such as flour, starch, a sugar, or a salt. The pre-mix may contain other dough-improving and/or bread-improving additives, e.g., any of the additives, including enzymes, mentioned above.

The present invention further relates to baking additives in the form of a granulate or agglomerated powder, which comprise a polypeptide of the present invention. The baking additive preferably has a narrow particle size distribution with more than 95% (by weight) of the particles in the range from 25 to 500 µm.

In dough and bread making the present invention may be used in combination with the processing aids defined hereinbefore such as the chemical processing aids like oxidants (e.g. ascorbic acid), reducing agents (e.g. L-cysteine), oxidoreductases (e.g. glucose oxidase) and/or other enzymes such as polysaccharide modifying enzymes (e.g. α-amylase, hemicellulase, branching enzymes, etc.) and/or protein modifying enzymes (endoprotease, exoprotease, branching enzymes, etc.).

EXAMPLE 1

Fermentation of *Aspergillus niger*

Lipolytic enzymes encoded by the nucleotide sequence as provided herein were obtained by constructing expression plasmids containing the DNA sequences, transforming an *A. niger* strain with this plasmid and growing the *Aspergillus niger* strains in the following way.

Fresh spores ($10^6$-$10^7$) of *A. niger* strains were inoculated in 20 ml, CSL-medium (100 ml flask, baffle) and grown for 20-24 hours at 34° C. and 170 rpm. After inoculation of 5-10 ml CS L pre-culture in 100 ml CSM medium (500 ml flask, baffle) the strains were fermented at 34° C. and 170 rpm for 3-5 days.

Cell-free supernatants were obtained by centrifugation in 50 ml Greiner tubes (30 minutes, 5000 rpm). The supernatants were pre-filtered over a GF/A Whatman Glass microfiber filter (150 mm/E) to remove the larger particles, adjusted to pH 5 with 4 N KOH (if necessary) and sterile filtrated over a 0.2 µm (bottle-top) filter with suction to remove the fungal material. The supernatants were stored at 4° C. (or −20° C.).

The CSL medium consisted of (in amount per litre): 100 g Corn Steep Solids (Roquette), 1 g $NaH_2PO4*H_2O$, 0.5 g $MgSO_4*7H_2O$, 10 g glucose*$H_2O$ and 0.25 g Basildon (antifoam). The ingredients were dissolved in demi-water and the pH was adjusted to pH 5.8 with NaOH or $H_2SO_4$; 100 ml flasks with baffle and foam ball were filled with 20 ml fermentation broth and sterilized for 20 minutes at 120° C. after which 200 µl of a solution containing 5000 IU/ml penicillin and 5 mg/ml Streptomycin was added to each flask after cooling to room temperature.

The CSM medium consisted of (in amount per litre): 150 g maltose*H2O, 60 g Soytone (pepton), 1 g $NaH_2PO4*H_2O$, 15 g $MgSO_4*7H_2O$, 0.08 g Tween 80, 0.02 g Basildon (antifoam), 20 g MES, 1 g L-arginine. The ingredients were dissolved in demi-water and the pH was adjusted to pH 6.2 with NaOH or $H_2SO_4$; 500 ml flasks with baffle and foam ball were filled with 100 ml fermentation broth and sterilized for 20 minutes at 120° C. after which 1 ml of a solution containing 5000 IU/ml penicillin and 5 mg/ml Streptomycin was added to each flask after cooling to room temperature.

EXAMPLE 2

Purification of the Lipolytic Enzymes of the Invention

Step 1—Preparation of Ultrafiltrates

The supernatants of the cultures, as obtained in Example 1, were ultrafiltrated to remove the low molecular contaminations that could interfere with the enzymatic activity determinations and the baking tests. Ultrafiltration of 30 ml supernatant was performed in a Millipore Labscale TFF system equipped with a filter with a 10 kDa cut-off.

Depending on their colour, the samples were washed 3-5 times with 40 ml volumes of cold 100 mM phosphate buffer pH 6.0 including 0.5 mM $CaCl_2$. The final volume of the enzyme solution was 30 ml and is further referred to as "ultrafiltrate".

Step 2—Determination of the Lipolytic Enzymes Concentration by A280 and HPSEC.

The concentration of the lipolytic enzymes in the ultrafiltrate was calculated from the extinction at 280 nm (A280) attributable to the lipolytic enzymes and the calculated molecular extinction coefficient of the lipolytic enzymes. Measurement of the A280 was performed in an Uvikon XL Secomam spectrophotometer (Beun de Ronde, Abcoude, The Netherlands).

The molecular extinction coefficient of an enzyme can be calculated from the number of tyrosine, tryptophan and cysteine residues per enzyme molecule (S. C. Gill and P. H. von Hippel, Anal. Biochem. 182, 319-326 (1989)). The molecular extinction coefficient of these amino acids are 1280, 5690 and 120 $M^{-1}.cm^{-1}$ respectively. The number of tyrosine, tryptophan and cysteine residues in the lipolytic enzymes of the invention can be deduced from the protein sequences selected from the group consisting of SEQ ID NO: 3, 6, 9, 12, 15, 18, 21, 24, 27, 30, 33, 36 and 39. The calculated extinction coefficients of the lipolytic enzymes of the invention are summarized in Table 2.

TABLE 2

| Lipolytic enzyme | SEQ ID NO: | # amino acids | | | M.W. (Da) | Calculated extinction coefficient at 280 nm | |
|---|---|---|---|---|---|---|---|
| | | Trp | Tyr | Cys | | $M^{-1} \cdot cm^{-1}$ | $(1 mg/ml)^{-1} \cdot cm^{-1}$ |
| NBE028 | 3 | 13 | 26 | 6 | 64141 | 107970 | 1.7 |
| NBE029 | 6 | 14 | 27 | 6 | 63250 | 114940 | 1.8 |
| NBE030 | 9 | 17 | 26 | 6 | 59952 | 130730 | 2.2 |
| NBE031 | 12 | 9 | 27 | 4 | 61173 | 86250 | 1.4 |
| NBE032 | 15 | 3 | 13 | 6 | 29683 | 34430 | 1.2 |

TABLE 2-continued

| Lipolytic enzyme | SEQ ID NO: | # amino acids Trp | # amino acids Tyr | # amino acids Cys | Calculated M.W. (Da) | Calculated extinction coefficient at 280 nm $M^{-1} \cdot cm^{-1}$ | Calculated extinction coefficient at 280 nm $(1\,mg/ml)^{-1} \cdot cm^{-1}$ |
|---|---|---|---|---|---|---|---|
| NBE033 | 18 | 7 | 24 | 2 | 44890 | 70790 | 1.6 |
| NBE034 | 21 | 11 | 19 | 7 | 53796 | 87750 | 1.6 |
| NBE036 | 24 | 10 | 23 | 7 | 64945 | 87180 | 1.3 |
| NBE038 | 27 | 13 | 29 | 4 | 55161 | 111570 | 2.2 |
| NBE039 | 30 | 11 | 26 | 6 | 59298 | 96590 | 1.6 |
| NBE043 | 33 | 16 | 35 | 8 | 62564 | 136800 | 2.2 |
| NBE045 | 36 | 0 | 6 | 6 | 26688 | 8400 | 0.31 |
| NBE042 | 39 | 14 | 30 | 7 | 61593 | 118900 | 1.9 |

The extinction of the ultrafiltrate at 280 nm (A280) that is attributable to the lipolytic enzymes depends on the purity of the enzyme sample. This purity was determined using HPSEC (High Performance Size Exclusion Chromatography) with a TSK SW-XL column (300*7.8 mm; MW range 10-300 kDa). The elution buffer consisted of 25 mM sodium phosphate buffer pH 6.0 and was used at a flow of 1 ml/min. Samples of 5-100 ul were injected. The absorbance at 280 nm was measured.

The A280 in the ultrafiltrate attributable to the lipolytic enzyme of the invention was obtained from the ratio of the peak surface of the respective lipolytic enzyme peak in the chromatogram and the total surface of the peaks absorbing at 280 nm. The lipolytic enzyme concentration in the ultrafiltrate was then calculated by multiplying the A280 of the ultrafiltrate by the ratio described above and divided by the calculated extinction coefficient (1 mg/ml solution—Table 2 most right column) for each lipolytic enzyme.

EXAMPLE 3

Activity Measurements

The cell-free supernatants obtained in Example 1 were subjected to the lipase, phospholipase and galactolipase assays as summarized in Table 3.

TABLE 3

Lipolytic enzyme activities in the cell free supernants as prepared in Example 1.

| Lipolytic enzyme | Lipase | phospholipase A | lysophospholipase | galactolipase |
|---|---|---|---|---|
| NBE028 | + | + | + | 0 |
| NBE029 | + | + | + | 0 |
| NBE031 | +++ | + | + | + |
| NBE032 | ++ | + | + | 0 |
| NBE033 | + | ++ | + | + |
| NBE034 | 0 | + | 0 | 0 |
| NBE036 | 0 | + | + | 0 |
| NBE038 | 0 | + | 0 | 0 |
| NBE039 | + | 0 | 0 | 0 |
| NBE043 | + | 0 | 0 | 0 |

0 = not different from blanc; +/++/+++ = higher than blanc;

Lipase activity was determined spectrophotometrically by using 2,3-mercapto-1-propanol-tributyrate (TBDMP) as a substrate. Lipase hydrolyses the sulphide bond of TBDMP thereby liberating thio-butanoic acid which in a subsequent reaction with 4,4,-dithiodipyridine (DTDP) forms 4-thiopyridone. The latter is in a tautomeric equilibrium with 4-mercapthopyridine which absorbs at 334 nm. The reaction is carried out in 0.1 M acetate buffer pH 5.0 containing 0.2% Triton-X100, 0.65 mM TBDMP and 0.2 mM DTDP at 37° C. One lipase unit is defined as the amount of enzyme that liberates 1 micromole of 4 thio-butanoic acid per minute at the reaction conditions stated.

Phospholipase A was determined spectrophotometrically by using 1,2-dithiodioctanoyl-phosphatidylcholine as a substrate. Phospholipase A hydrolyses the sulphide bond at the 1 position (PLA1) or the 2 position (PLA2) thereby liberating 4 thio-octanoic acid which, in a subsequent reaction reacts with 4,4'-dithiopyridine to form 4 thiopyridone. The latter is in tautomeric equilibrium with 4mercaptopyridine that absorbs at 334 nm. The reaction is carried out in 0.1 M acetate buffer pH 4.0 containing 0.2% Triton-X100, 0.65 mM substrate and 0.2 mM DTDP at 37° C. One phospholipase A unit (PLA) is defined as the amount of enzyme that liberates 1 micromole of 4 thio-octanoic acid per minute at the reaction conditions stated.

Lysophospholipase activity was determined with $^{31}$P-NMR spectroscopy by using lysophosphatidyl-choline as a substrate. Lysophospholipase hydrolyses the ester bond thereby liberating the fatty acid from the glycerol moiety. The so-formed glycerolphosphocholine is quantified using NMR. The reaction is carried out in 50 mM acetic acid buffer pH 4.5 further containing 1 mg/ml lysophosphatidylcholine and 5 mM $CaCl_2$ for 30 minutes at 55° C.

One lysophospholipase unit (LPC) is defined as the amount of enzyme that forms 1 micromole of 4 glycerolphosphocholine per minute at the reaction conditions stated.

Galactolipase activity was determined with H-NMR spectroscopy by using digalactosyldiglyceride as a substrate, according to the method described by Hirayama and Matsuda (1972) Agric. Biol. Chem. 36, 1831. Galactolipase hydrolyses the ester bond between the fatty acids and the glycerol backbone thereby liberating one or both fatty acids. The reaction is carried out in 50 mM acetic acid buffer pH 4.5 further containing 4 mM $CaCl_2$, 0.2% Triton X-100 and 1 mg/ml digalactosyldiglyceride (Lipid Products) for 30 minutes at 30° C. One galactolipase unit is defined as the amount of enzyme that forms 1 micromole of fatty acid per minute at the reaction conditions stated.

The ultrafiltrates obtained in Example 2, were subjected to the FAU enzyme activity measurement. The activity of the fungal alpha-amylase was measured using Phadebas Amylase test tablets (Pharmacia). Phadebas tablets contain a water insoluble starch substrate and a blue dye, bound by cross-linking to the substrate. The substrate is hydrolysed by fungal amylase, releasing dyed soluble maltodextrines that go into solution. A calibration curve was prepared with a solution containing a reference fungal alpha amylase activity. From the reference and unknown samples appropriate dilutions were prepared in 50 mM malic acid buffer pH 5.5. Samples of 5 ml were incubated with 30° C. for 5 minutes, a Phadebas tablet was added and after 15 minutes the reaction was stopped by the addition of 1.0 ml 0.5 N sodium hydroxide. The mixtures were allowed to cool down to room temperature for 5 minutes after which 4.0 ml water was added, shaken by hand and after 15 minutes the samples were centrifuged at 4700 rpm for 10 minutes. The extinction of the top layers was measured at 620 nm. The OD 620 nm is a measure for fungal alpha amylase activity. One fungal amylase unit (FAU) is defined herein as the amount of enzyme that converts 1 gram of starch (100% dry matter) per hour into a product having a transmission at 620 nm after reaction with a iodine solution of known strength at the reaction conditions stated.

TABLE 4

FAU and protein in the ultrafiltrates as prepared in Example 2.

| lipolytic enzyme | Protein (mg/ml) from the 280 nm analysis | fungal amylase (FAU/ml) |
|---|---|---|
| NBE028 | 2.3 | 4.5 |
| NBE029 | 1.3 | 3.0 |
| NBE030 | 0.4 | 2.6 |
| NBE031 | 0.1 | 2.5 |
| NBE032 | 1.0 | 0.3 |
| NBE033 | ND | 0.3 |
| NBE034 | ND | 2.7 |
| NBE036 | ND | 3.4 |
| NBE038 | 2.0 | 3.7 |
| NBE039 | 2.2 | 0.6 |
| NBE043 | 0.1 | 0.2 |
| NBE045 | ND | 4.0 |
| NBE042 | 1.6 | 1.5 |

In addition to the activities mentioned in Table 4, minor activities of glucoamylase was also present, however in such low amounts that these enzymes did not interfere in the baking experiments described in example 4.

Example 4

Baking Experiments 1—Pup Loaves

Pup loaves were baked from 150 gram dough pieces obtained by mixing 200 g flour (Kolibri™/Ibis™ in a ratio of 80/20), 1.4 g dried baker's yeast (Fermipan®), 4 g salt, 3 g sugar, 10 mg ascorbic acid, 116 g water and 2 g fat. After mixing for 6 minutes and 15 seconds in a pin mixer, the dough was divided into pieces of 150 grams and proofed for 45 minutes at 30° C., punched, proofed for another 25 minutes, moulded and panned. Proofing took place at a relative humidity of 90-100%. After a final proof of 70 minutes at 30° C., the dough was baked for 20 minutes at 225° C.

The various effects (Tables 5 and 6) of the different lipolytic enzymes in the baking experiments were compared with a control containing the same amount of fungal amylase that was added otherwise by the dosage of the ultrafiltrate (for the fungal amylase activity in the ultrafiltrates see Table 4). This was necessary since the amounts of fungal amylase added with the lipolytic enzymes in particular affected the loaf volume, not the other parameters. The volume of the breads with the control amount of fungal amylase added was taken as 100%.

Loaf volume was determined by the Bread Volume Measurer BVM-3 (RI Cards Instruments AB, Viken, Sweden). The principle of this measurement is based on the reflection of ultrasound measured by a sensor around a rotating bread. A measurement time was taken of 45 seconds.

Dough stickiness and extensibility were evaluated by a qualified baker using the scale depicted in Table 5. The average of 2 loaves per object was measured.

After these tests the dough pieces were rounded and a first proof was performed for 45 minutes at 30° C. and hereafter the dough was punched, moulded, panned, proofed for 75 minutes at 30° C. The relative humidity during the proofs was set at 85%.

Subsequently the stability of the proofed dough was judged by the presence of bladders, torn side crust and irregular curved surfaces of the crust. The dough pieces were baked for 20 minutes at 225° C. Loaf volumes were determined by the BVM-3 method: in the table the average is presented of 2 breads that are baked from the same object.

The crumb structure was judged by a qualified baker using the scale depicted in Table 5. After storing the loaves for three days in polyethylene bags at room temperature crumb firmness was measured using a Stevens Texture Analyser. Two slices of 2 cm thickness from the centre of each loaf were analysed by the texture analyser using a probe of 1.5 inch diameter, a compression depth of 5 mm (25%) and a rate of compression of 0.5 mm/sec. In the table the average is shown of two measurements.

Crust colour was judged by a qualified baker according to the scale depicted in Table 5. As a reference the standard recipe for Dutch tin bread was used.

Crumb colour was judged by a qualified baker according to the scale depicted in Table 5. The colour of the crumb of the control breads was judged as normal (3). As a positive control the breads of 2 objects are used with the same composition as the control plus 0.5% soya flour. The proofing and baking procedure are the same as that of the control without soya flour. The latter is judged as "excellent".

The overhanging top of the bread was judged by the hanging of the top in relation to the baking tin, the lower the edges of the top the lower the judgement. The less hanging, the better the judgement, Staling of the bread was judged by feeling the firmness of the crumb of slices of the bread. Before slicing took place, the bread was stored in a plastic bag at room temperature for 4 days. The softer the crumb of the slices is, the better the judgement.

TABLE 5

| | effect | Score 1 | 2 | 3 | 4 | 5 |
|---|---|---|---|---|---|---|
| Dough | dough stickiness | too sticky | sticky | control bread | much better | excellent dry |
| | dough extensibility | Too short | Shorter than the control | control bread | good | too long |
| baked bread | crumb structure | poor | non-uniform | control bread | good | excellent |
| | crust colour | Nearly white | too light | control bread | excellent | too dark |
| | crumb colour | Far too yellow | too yellow | control bread | excellent | absolutely white |
| | staling | Far too firm | too firm | control bread | softer | excellent |

TABLE 6

Baking performance of the lipolytic enzymes of the invention

| Lipolytic enzyme | Volume (%) | Dough stickyness | Dough extensibility | Dough stability | Crumb structure | Crust colour | Crumb colour | Overhanging top | Staling |
|---|---|---|---|---|---|---|---|---|---|
| NBE028 | 100 | 3 | 3 | 4 | 2 | 3 | 3 | 3 | 4 |
| NBE029 | 104 | 3 | 3 | 4 | 3 | 4 | 4 | 4 | 3 |
| NBE030 | 107 | 3 | 2 | 4 | 4 | 4 | 4 | 3 | 3 |
| NBE031 | 102 | 3 | 2 | 4 | 5 | 4 | 4 | 4 | 4 |
| NBE032 | 98 | 3 | 3 | 4 | 2 | 3 | 3 | 3 | 3 |
| NBE033 | 105 | 3 | 2 | 4 | 2 | 4 | 3 | 3 | 3 |
| NBE034 | 104 | 3 | 3 | 4 | 4 | 4 | 4 | 4 | 3 |
| NBE036 | 100 | 3 | 3 | 4 | 3 | 4 | 4 | 4 | 3 |
| NBE038 | 109 | 3 | 3 | 4 | 5 | 4 | 4 | 3 | 3 |
| NBE039 | 109 | 3 | 3 | 4 | 4 | 3 | 4 | 3 | 3 |
| NBE043 | 106 | 3 | 3 | 4 | 3 | 4 | 4 | 3 | 3 |
| NBE045 | 110 | 3 | 3 | 4 | 4 | 3 | 4 | 4 | 4 |
| NBE042 | 110 | 3 | 4 | 4 | 4 | 3 | 4 | 3 | 3 |

EXAMPLE 5

Baking Experiments 2—Batard

The baking performance of lipolytic enzymes according to the invention was tested in the French type of bread called "batard". Preparation of batards in a standard baking process was done by mixing 3000 g of wheat flour at circa 20° C., 70 g compressed yeast, 60 g salt, 68 ppm ascorbic acid, 30 ppm Bakezyme® HS$_{2000}$ (fungal hemicellulase), 7 ppm Bakezyme® P500 (fungal α-amylase) and 1680 ml water (8-10° C.) in a spiral mixer (Diosna: 2 minutes in speed 1; 100 Wh input in speed 2). The dough temperature was 27° C. The machineability of the dough was analysed by hand by a baker. The dough was given a bulk proof of 15 minutes in a proofing cabinet at 32° C. and 90% RH. Afterwards the dough was divided into 6 pieces of 350 g, rounded and proofed for 15 minutes at 32° C. and 90% RH. At the end of this period the dough pieces were moulded and shaped and given a final proof of 90 minutes at 32° C. and 90% RH. The fully proofed doughs were cut in the length of the dough piece and baked in an oven at 240° C. for 30 minutes with initial steam addition. After cooling down to room temperature the volumes of the loaves were determined by the BVM-method (see example 4).

Break, shred and shape of the breads were analysed directly after cooling down to room temperature by a qualified baker using the score in Table 7. After 16 hours (overnight) storage in a closed box at room temperature the crumb quality was assessed a qualified baker. The value for the breads (Table 8) was derived from 1 object.

TABLE 7

| Effect | | Score | | | |
| --- | --- | --- | --- | --- | --- |
| | 1 | 2 | 3 | 4 | 5 |
| Break and shred | extremely weak and soft | weak and soft | control bread | thin and crispy crust firm break of the cut | crust too thin, too hard |
| Crumb structure | poor | not uniform | control bread | good | excellent |
| shape height | flat | medium | control bread | larger than (3) | Much larger than (3) |
| cut | cut closed | cut closed | control bread | completely opened | completely opened; teared |

TABLE 8

Baking performance of the lipolytic enzymes of the invention

| | | parameter | | |
|---|---|---|---|---|
| lipolytic enzyme | Dosage* | Loaf volume (%) | Break & Shred | Shape | Crumb structure |
| None | 0 | 100 | 3 | 3 | 3 |
| NBE028 | 0.75 | 3 | 4 | 4 | 4 |
| NBE030 | 3 | 103 | 4 | 4 | 3 |
| NBE031 | 2.5 | 95 | 4 | 4 | 3 |
| NBE036 | ND | 88 | 3 | 3 | 3 |
| NBE038 | 30 | 100 | 4 | 4 | 3 |
| NBE39 | 64 | 126 | 3 | 4 | 3 |
| NBE045 | ND | 89 | 4 | 4 | 3 |
| NBE042 | 12 | 98 | 3 | 4 | 4 |

*in ppm based on flour weight and enzyme weight determined by the A280 method

The invention claimed is:

1. An isolated lipolytic enzyme comprising the amino acid sequence of SEQ ID NO: 12.

2. The enzyme of claim 1 obtained from *Aspergillus niger*.

3. An isolated lipolytic enzyme obtainable by expressing a polynucleotide which is hybridisable to a nucleotide sequence selected from the group consisting of SEQ ID NOS: 10 and 11 under highly stringent conditions; wherein highly stringent conditions are hybridizing in 5x sodium chloride-sodium citrate (SSC), 5x Denhardt's solution, and 1.0% sodium dodecyl sulfate (SDS) at 68° C. and washing in 0.2x SSC and 0.1% SDS at room temperature.

4. A recombinant lipolytic enzyme comprising a functional domain of the lipolytic enzyme of claim 1.

5. A fusion protein comprising the lipolytic enzyme of claim 1.

6. A process for the production of dough comprising adding the lipolytic enzyme of claim 1 to dough ingredients.

7. A process for the production of a baked product from a dough comprising baking dough as prepared by the process according to claim 6.

8. A fusion protein comprising the lipolytic enzyme of claim 3.

9. A process for the production of dough comprising adding the lipolytic enzyme of claim 3 to dough ingredients.

10. A process for the production of a baked product from a dough comprising baking dough as prepared by the process according to claim 9.

11. An isolated lipolytic enzyme encoded by a polynucleotide which is at least 95% identical to a nucleotide sequence selected from the group consisting of SEQ ID NOS: 1011 which is obtained by expressing a vector comprising the nucleotide sequence in an appropriate host cell.

12. A fusion protein comprising the lipolytic enzyme of claim 11.

13. A process for the production of dough comprising adding the lipolytic enzyme of claim 9 to dough ingredients.

14. A process for the production of a baked product from a dough comprising baking dough as prepared by the process according to claim 13.

15. An isolated lipolytic enzyme comprising a polypeptide which is at least 95% identical to the amino acid sequence of SEQ ID NO: 12.

16. A fusion protein comprising the amino acid sequence of the lipolytic enzyme of claim 15.

17. A process for the production of dough comprising adding the lipolytic enzyme of claim 15 to dough ingredients.

18. A process for the production of a baked product from a dough comprising baking dough as prepared by the process according to claim 17.

* * * * *